(12) United States Patent
Robinson

(10) Patent No.: US 9,526,645 B2
(45) Date of Patent: Dec. 27, 2016

(54) SAFETY MECHANISM FOR AN IMPLANTABLE DEVICE DEPLOYMENT APPARATUS

(71) Applicant: Merit Medical Systems, Inc., South Jordan, UT (US)

(72) Inventor: Thomas Patrick Robinson, Addison, TX (US)

(73) Assignee: Merit Medical Systems, Inc., South Jordan, UT (US)

( * ) Notice: Subject to any disclaimer, the term of this patent is extended or adjusted under 35 U.S.C. 154(b) by 489 days.

(21) Appl. No.: 13/664,234

(22) Filed: Oct. 30, 2012

(65) Prior Publication Data

US 2013/0116771 A1    May 9, 2013

Related U.S. Application Data

(60) Provisional application No. 61/553,844, filed on Oct. 31, 2011, provisional application No. 61/596,473, filed on Feb. 8, 2012.

(51) Int. Cl.
*A61F 2/06* (2013.01)
*A61F 2/95* (2013.01)
(Continued)

(52) U.S. Cl.
CPC .............. *A61F 2/95* (2013.01); *A61F 2/2436* (2013.01); *A61F 2/962* (2013.01); *A61F 2/966* (2013.01);
(Continued)

(58) Field of Classification Search
CPC .......... A61F 2/95; A61F 2/966; A61F 2/2436; A61F 2/0095; A61F 2/01; A61F 2/02; A61F 2/07; A61F 2/2403; A61F 2/2406; A61F 2/2409; A61F 2/2418; A61F 2/2427; A61F 2/243; A61F 2/2433; A61F 2/2439; A61F 2/962; A61F 2002/011; A61F 2002/015; A61F 2002/9517; A61F 2002/9522; A61F 17/1205; A61F 17/3468; A61F 17/347; A61M 2025/0175
(Continued)

(56) References Cited

U.S. PATENT DOCUMENTS 5,201,757 A    4/1993    Heyn et al.
5,591,172 A    1/1997    Bachmann et al.
(Continued)

FOREIGN PATENT DOCUMENTS

DE    9209908    9/1992
DE    4323866    1/1994
(Continued)

OTHER PUBLICATIONS

Office Action dated Jan. 3, 2014 for U.S. Appl. No. 11/432,964.
(Continued)

*Primary Examiner* — Diane Yabut
*Assistant Examiner* — Martin T Ton
(74) *Attorney, Agent, or Firm* — Stoel Rives LLP

(57) ABSTRACT

Systems and methods are disclosed for delivering a stent to a lumen internal to a body of a patient and for sheathing a stent just prior to an insertion procedure. One embodiment comprises a delivery device having a partially sheathed configuration, a fully sheathed delivery configuration, and a deployed configuration. A panchor (combination pusher and anchor) is configured to engage and limit proximal and distal movement of the implantable device. An outer sheath surrounds a distal portion of an inner member and retains the implantable device near the distal end. The outer sheath is slidably moveable relative to the inner member to deploy the implantable device. Proximal movement of a trigger results (Continued)

in movement of the outer sheath to deploy the implantable device. A sheathing mechanism is configured to crimp and fully sheathe the implantable device prior to a deployment procedure.

13 Claims, 36 Drawing Sheets

(51) Int. Cl.
*A61F 2/966* (2013.01)
*A61F 2/24* (2006.01)
*A61F 2/962* (2013.01)
*A61F 2/00* (2006.01)

(52) U.S. Cl.
CPC ............ *A61F 2/0095* (2013.01); *A61F 2/2418* (2013.01); *A61F 2002/9522* (2013.01)

(58) Field of Classification Search
USPC ................................................ 623/1.11–1.12
See application file for complete search history.

(56) References Cited

U.S. PATENT DOCUMENTS

| | | | |
|---|---|---|---|
| 5,733,325 A | 3/1998 | Robinson et al. | |
| 5,759,186 A | 6/1998 | Buchmann et al. | |
| 5,824,041 A | 10/1998 | Lenker et al. | |
| 5,868,755 A | 2/1999 | Kanner et al. | |
| 5,916,147 A | 6/1999 | Boury | |
| 5,954,729 A | 9/1999 | Bachmann et al. | |
| 6,093,194 A | 7/2000 | Mikus et al. | |
| 6,143,021 A | 11/2000 | Staehle | |
| 6,146,415 A * | 11/2000 | Fitz ........................... A61F 2/95 606/171 |
| 6,162,231 A | 12/2000 | Mikus et al. | |
| 6,383,211 B1 | 5/2002 | Staehle | |
| 6,391,051 B2 | 5/2002 | Sullivan, III et al. | |
| 6,413,269 B1 | 7/2002 | Bui et al. | |
| 6,428,566 B1 | 8/2002 | Holt | |
| 6,514,261 B1 | 2/2003 | Randall et al. | |
| 6,629,981 B2 | 10/2003 | Bui et al. | |
| 6,669,719 B2 | 12/2003 | Wallace et al. | |
| 6,726,712 B1 | 4/2004 | Raeder-Devens et al. | |
| 6,776,791 B1 | 8/2004 | Stallings et al. | |
| 6,866,669 B2 | 3/2005 | Buzzard et al. | |
| 6,926,732 B2 | 8/2005 | Derus et al. | |
| 7,309,350 B2 | 12/2007 | Landreville et al. | |
| 7,393,357 B2 | 7/2008 | Stelter et al. | |
| 7,591,848 B2 | 9/2009 | Allen | |
| 7,731,654 B2 | 6/2010 | Mandiardi et al. | |
| 8,439,934 B2 | 5/2013 | Satasiya et al. | |
| 8,518,099 B2 * | 8/2013 | Chanduszko et al. ....... 623/1.11 |
| 8,535,366 B2 | 9/2013 | Mangiardi et al. | |
| 8,926,683 B2 * | 1/2015 | Gill et al. .................... 623/1.11 |
| 9,192,496 B2 | 11/2015 | Robinson | |
| 2001/0037141 A1* | 11/2001 | Yee ........................... A61F 2/95 623/1.11 |
| 2002/0151967 A1 | 10/2002 | Mikus et al. | |
| 2002/0183827 A1 | 12/2002 | Derus et al. | |
| 2002/0193749 A1* | 12/2002 | Olovson ............ A61M 5/3243 604/198 |
| 2003/0050686 A1 | 3/2003 | Raeder-Devens et al. | |
| 2003/0167060 A1 | 9/2003 | Buzzard et al. | |
| 2004/0030381 A1 | 2/2004 | Shu | |
| 2004/0193243 A1 | 9/2004 | Mangiardi et al. | |
| 2004/0267281 A1 | 12/2004 | Harari et al. | |
| 2005/0090887 A1 | 4/2005 | Pryor | |
| 2005/0125050 A1 | 6/2005 | Carter et al. | |
| 2005/0149160 A1 | 7/2005 | McFerran | |
| 2005/0278010 A1 | 12/2005 | Richardson | |
| 2006/0258972 A1* | 11/2006 | Mangiardi ................ A61F 2/95 604/15 |
| 2007/0043421 A1 | 2/2007 | Mangiardi et al. | |
| 2007/0100421 A1 | 5/2007 | Griffin | |
| 2007/0208350 A1 | 9/2007 | Gunderson | |
| 2007/0250150 A1 | 10/2007 | Pal et al. | |
| 2007/0270932 A1 | 11/2007 | Headley et al. | |
| 2008/0114443 A1 | 5/2008 | Mitchell et al. | |
| 2009/0099636 A1* | 4/2009 | Chanduszko ........... A61F 2/915 623/1.11 |
| 2009/0118740 A1 | 5/2009 | Mangiardi et al. | |
| 2009/0192518 A1 | 7/2009 | Golden et al. | |
| 2009/0292262 A1 | 11/2009 | Adams et al. | |
| 2010/0030256 A1 | 2/2010 | Dubrul et al. | |
| 2010/0049295 A1 | 2/2010 | Satasiya et al. | |
| 2010/0057185 A1 | 3/2010 | Melsheimer et al. | |
| 2010/0252470 A1 | 10/2010 | Ryan et al. | |
| 2011/0015616 A1* | 1/2011 | Straubinger et al. ......... 604/528 |
| 2011/0082464 A1 | 4/2011 | Douk et al. | |
| 2011/0190862 A1 | 8/2011 | Bashiri et al. | |
| 2011/0208296 A1 | 8/2011 | Duffy et al. | |
| 2011/0264191 A1 | 10/2011 | Rothstein | |
| 2011/0288482 A1* | 11/2011 | Farrell et al. ............ 604/164.04 |
| 2012/0310320 A1 | 12/2012 | Gill et al. | |
| 2013/0116770 A1 | 5/2013 | Robinson | |
| 2013/0116771 A1 | 5/2013 | Robinson | |
| 2013/0116772 A1 | 5/2013 | Robinson et al. | |
| 2013/0274870 A1 | 10/2013 | Lombardi et al. | |

FOREIGN PATENT DOCUMENTS

| | | |
|---|---|---|
| EP | 0364420 | 4/1990 |
| EP | 0872220 | 10/1998 |
| WO | WO96/31174 | 10/1996 |
| WO | WO00/78246 | 12/2000 |
| WO | WO02/087470 | 11/2002 |
| WO | WO03/090644 | 11/2003 |
| WO | WO2004/030571 | 4/2004 |
| WO | WO2005/070095 | 8/2005 |
| WO | WO2008/042266 | 4/2008 |
| WO | 2010130297 | 11/2010 |
| WO | PCT/US2012/062603 | 10/2012 |
| WO | 2013045262 | 4/2013 |
| WO | 2013066883 | 10/2013 |

OTHER PUBLICATIONS

Notice of Allowance dated Mar. 6, 2013 for U.S. Appl. No. 12/535,980.
International Search Report and Written Opinion dated Mar. 29, 2013 for PCT/US2012/062603.
Notice of Allowance dated Jun. 11, 2013 for U.S. Appl. No. 10/585,430.
Office Action dated Jul. 25, 2013 for U.S. Appl. No. 11/432,964.
Office Action dated May 5, 2014 for U.S. Appl. No. 13/313,929.
Notice of Allowance dated Oct. 21, 2014 for U.S. Appl. No. 13/313,929.
Office Action dated Jan. 22, 2013 for U.S. Appl. No. 10/585,430.
U.S. Appl. No. 13/313,929, filed Dec. 7, 2011, Gill et al.
U.S. Appl. No. 13/664,137, filed Oct. 30, 2012, Robinson.
U.S. Appl. No. 13/664,200, filed Oct. 30, 2012, Robinson.
U.S. Appl. No. 13/664,267, filed Oct. 30, 2012, Robinson.
PCT Notification of Transmittal of the International Search Report and Written Opinion dated Nov. 23, 2006 for PCT/US2006/018811.
The Supplementary European Search Report for EP Application No. 05705271.4, dated May 4, 2007.
International Search Report and Written Opinion dated Oct. 29, 2009 for PCT/US2009/052691.
Office Action dated Jul. 9, 2009 for U.S. Appl. No. 11/432,964.
Office Action dated Dec. 7, 2009 for U.S. Appl. No. 11/432,964.
International Search Report and Written Opinion dated Aug. 4, 2005 for PCT/US05/000515.
Office Action dated Dec. 8, 2009 for U.S. Appl. No. 10/585,430.
Office Action dated Nov. 9, 2010 for U.S. Appl. No. 10/585,430.
Office Action dated Jun. 7, 2011 for U.S. Appl. No. 10/585,430.
Office Action dated Aug. 13, 2012 for U.S. Appl. No. 10/585,430.
Restriction Requirement dated Mar. 6, 2012 for U.S. Appl. No. 12/535,980.

(56) References Cited

OTHER PUBLICATIONS

Office Action dated May 25, 2012 for U.S. Appl. No. 12/535,980.
Office Action dated Jan. 31, 2012 for U.S. Appl. No. 10/585,430.
Office Action dated Nov. 14, 2012 for U.S. Appl. No. 12/535,980.
International Publication and Search Report dated Feb. 25, 2012 for WO10021836.
International Publication and Search Report dated Aug. 4, 2005 for WO2005070095.
International Publication and Search Report dated Jun. 14, 2012 for WO2012078794.
European Search Report dated Feb. 3, 2015 for EP12846255.3.
International Preliminary Report dated May 15, 2014 for PCT/US2012/062603.
International Search Report and Written Opinion dated Sep. 28, 2005 for PCT/US2005/000515.
International Search Report and Written Opinion dated Nov. 23, 2006 for PCT/US2006/018811.
Notice of Allowance dated Jan. 14, 2015 for U.S. Appl. No. 11/432,964.
Office Action dated Mar. 24, 2015 for U.S. Appl. No. 13/664,267.
European Examination Report dated Feb. 18, 2015 for EP09791142.4.
Notice of Allowance dated Aug. 12, 2015 for U.S. Appl. No. 13/664,200.
Office Action dated Oct. 16, 2015 for U.S. Appl. No. 13/664,267.
Office Action dated Nov. 19, 2015 for U.S. Appl. No. 13/664,137.
Office Action dated Apr. 6, 2016 for U.S. Appl. No. 13/664,137.
Notice of Allowance dated Jun. 22, 2016 for U.S. Appl. No. 13/664,267.

\* cited by examiner

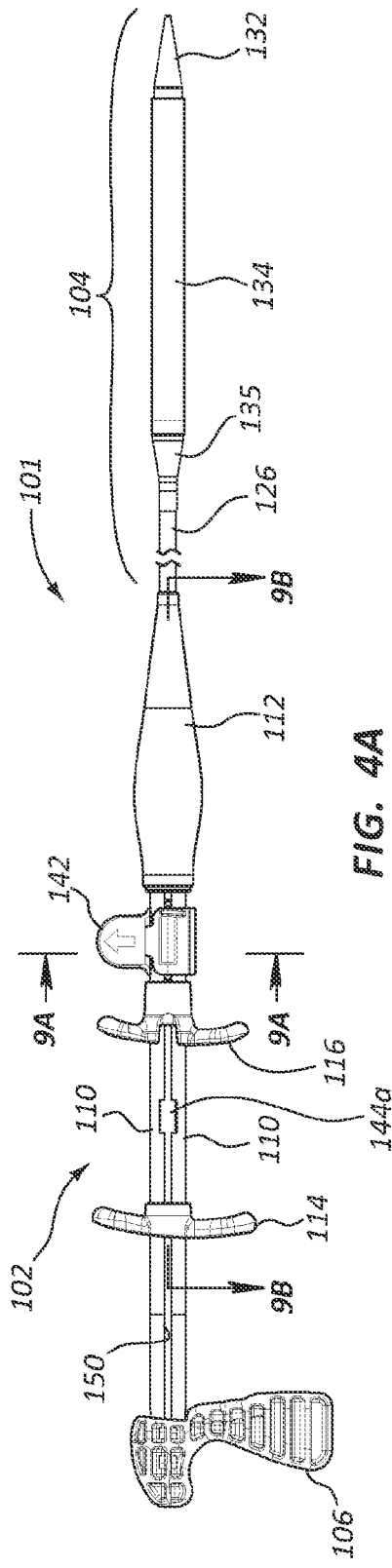
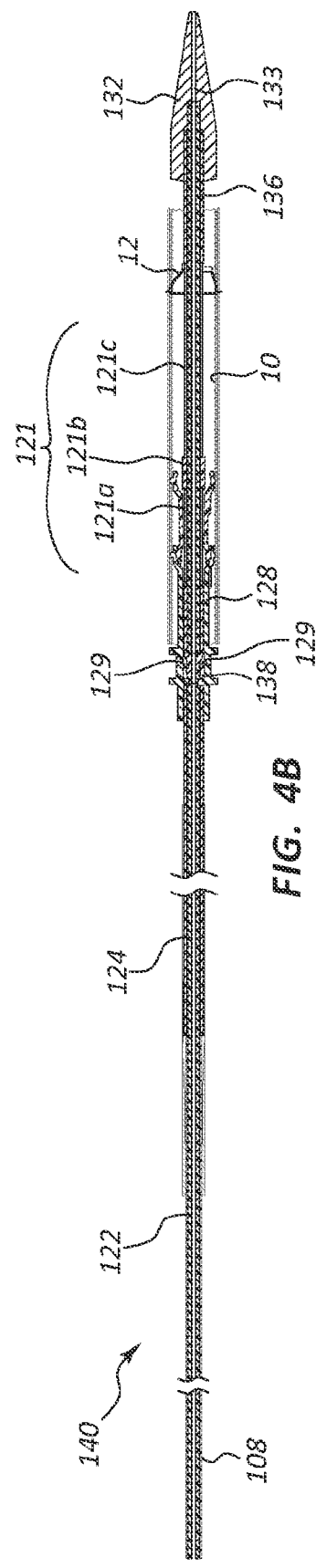
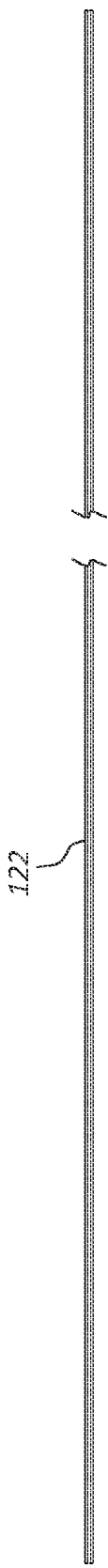
FIG. 4A
FIG. 4B
FIG. 4C

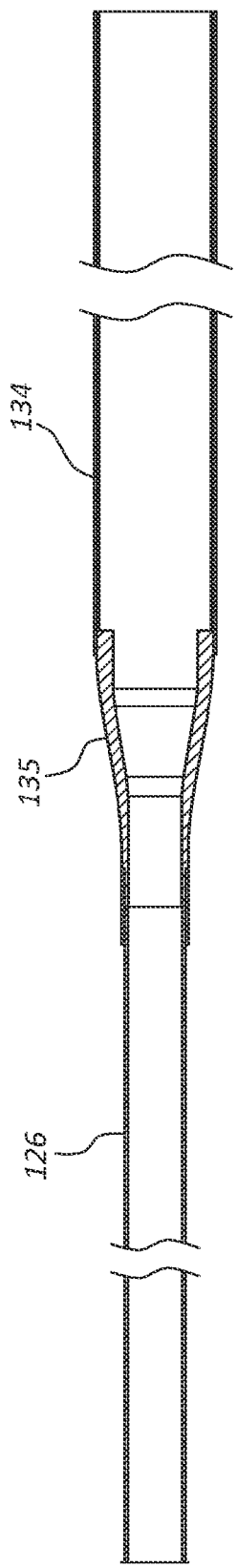
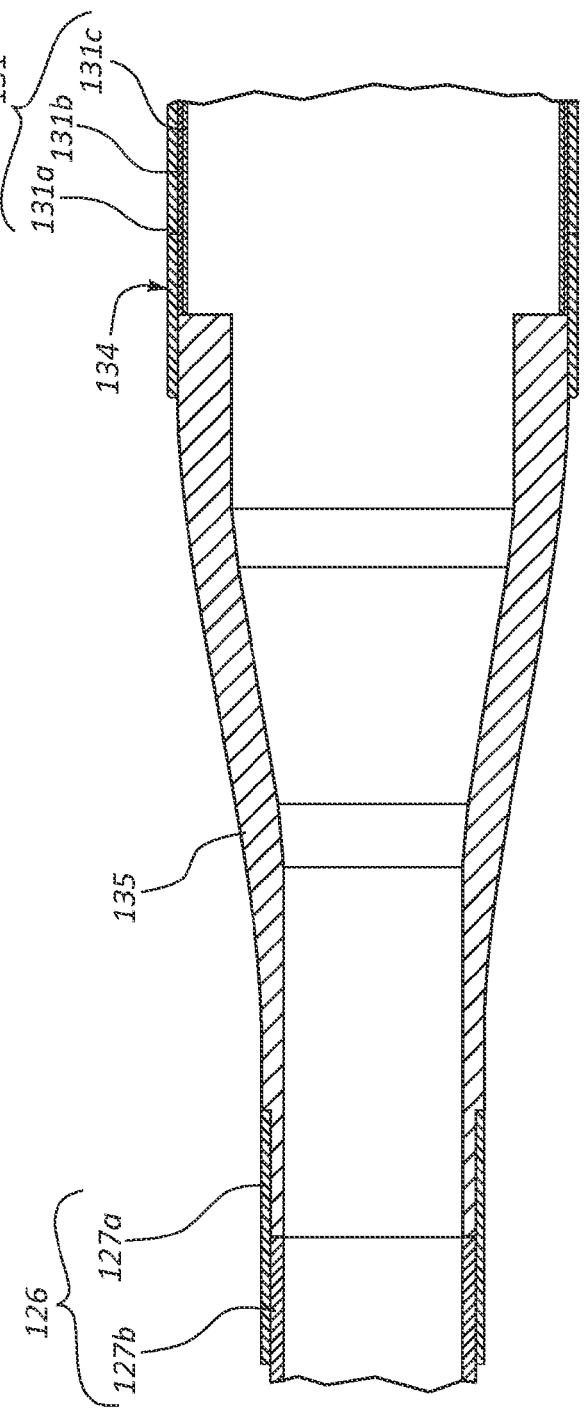
FIG. 4D1
FIG. 4D2

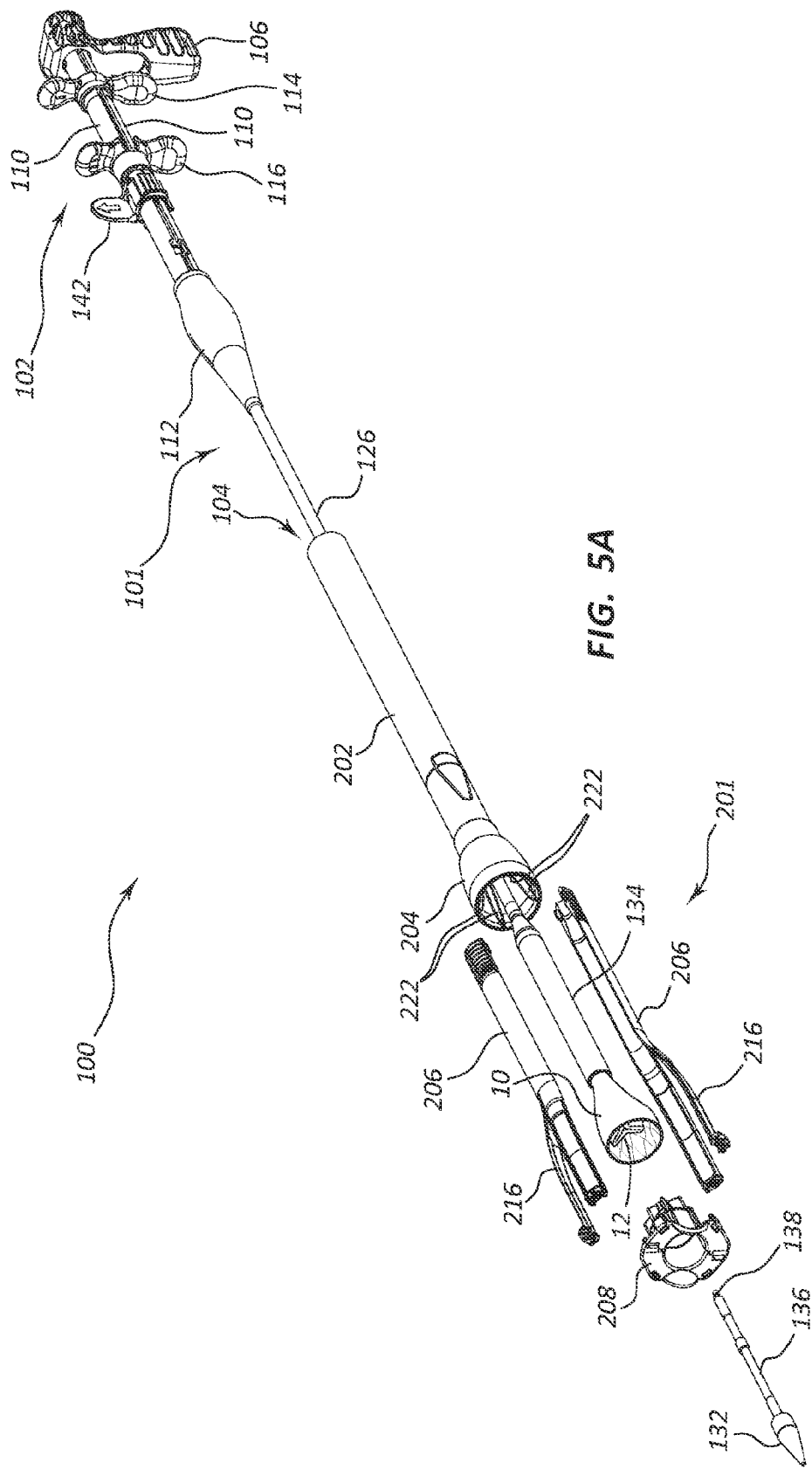

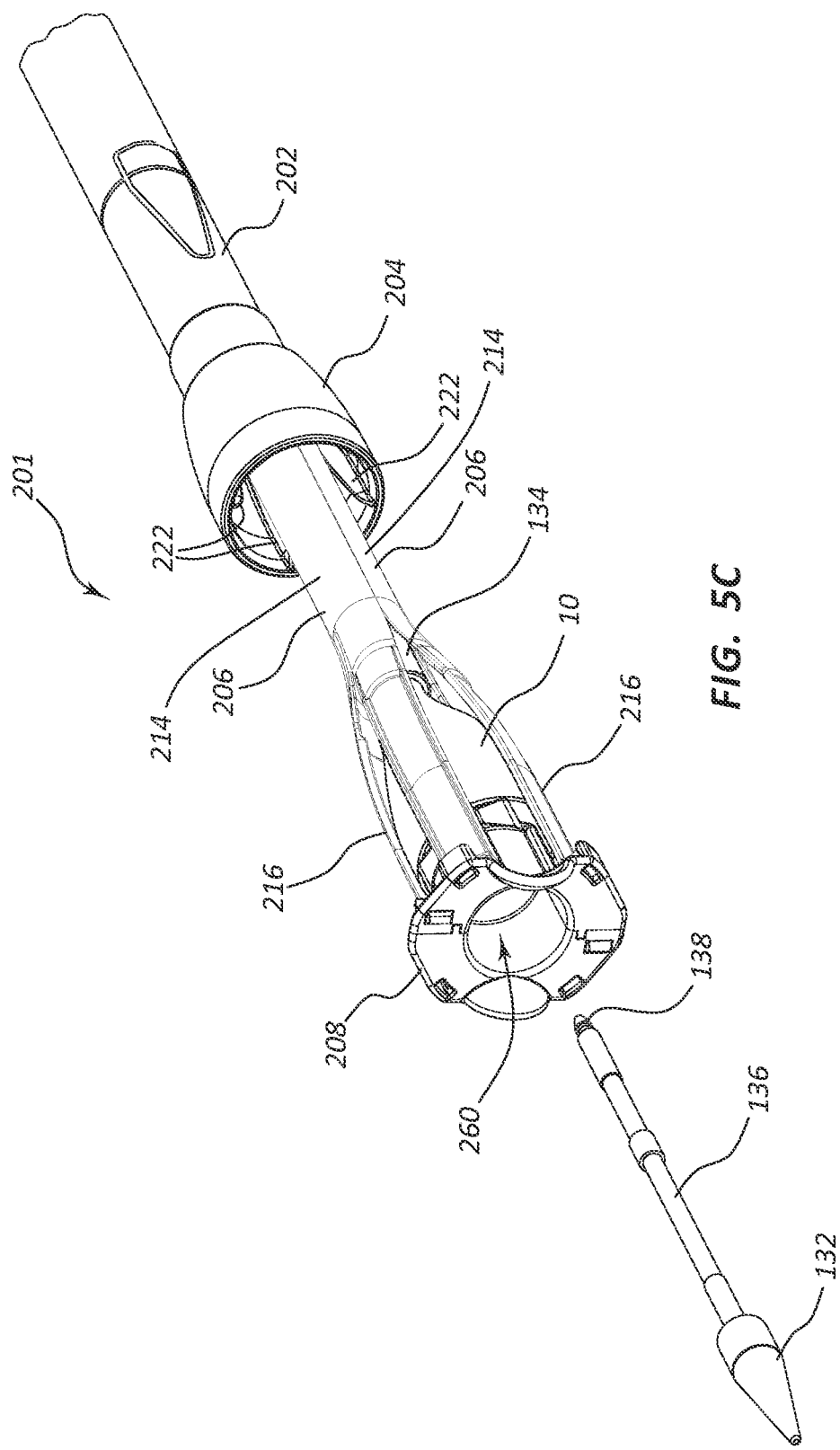

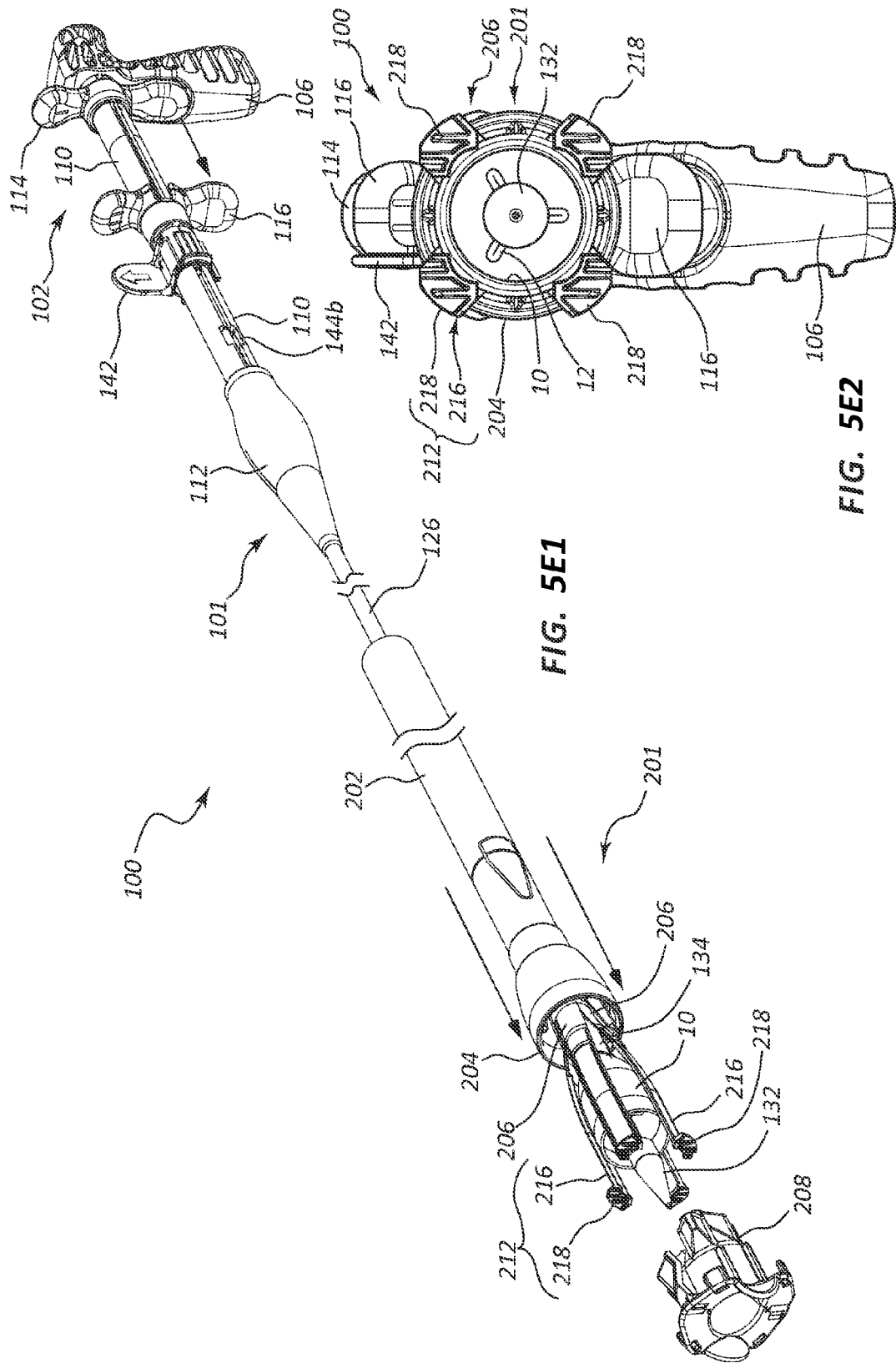
FIG. 5E1
FIG. 5E2

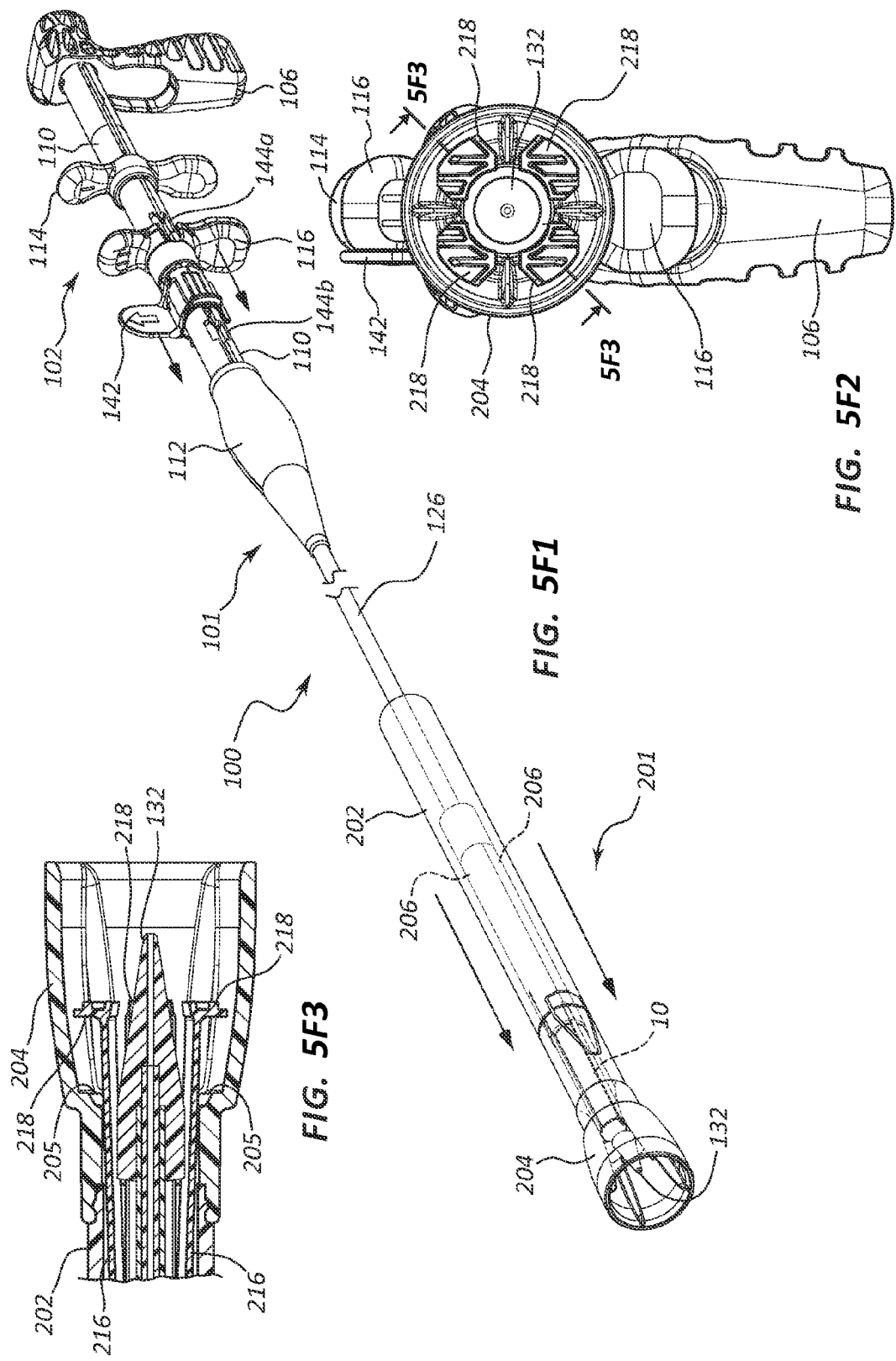

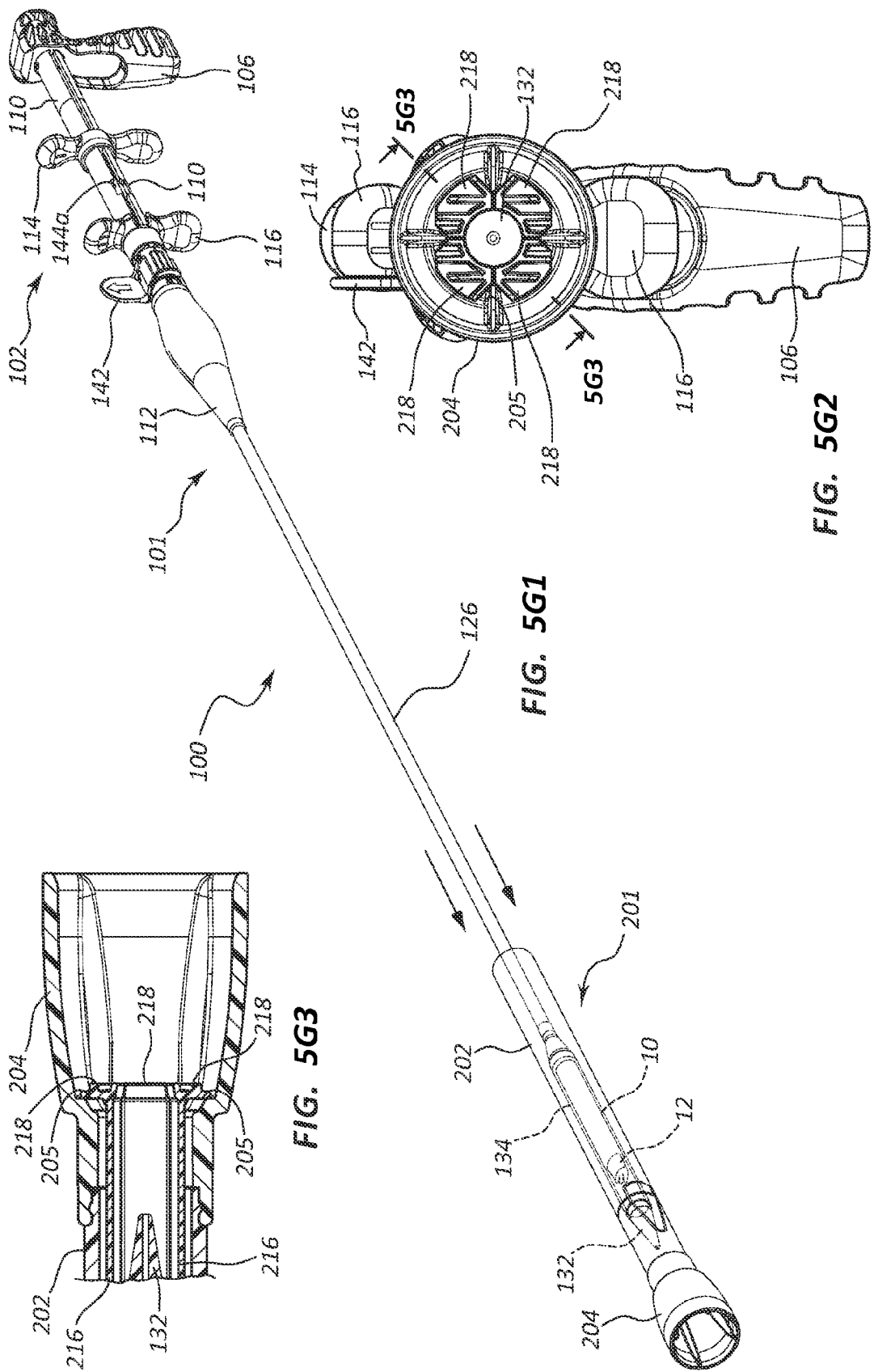

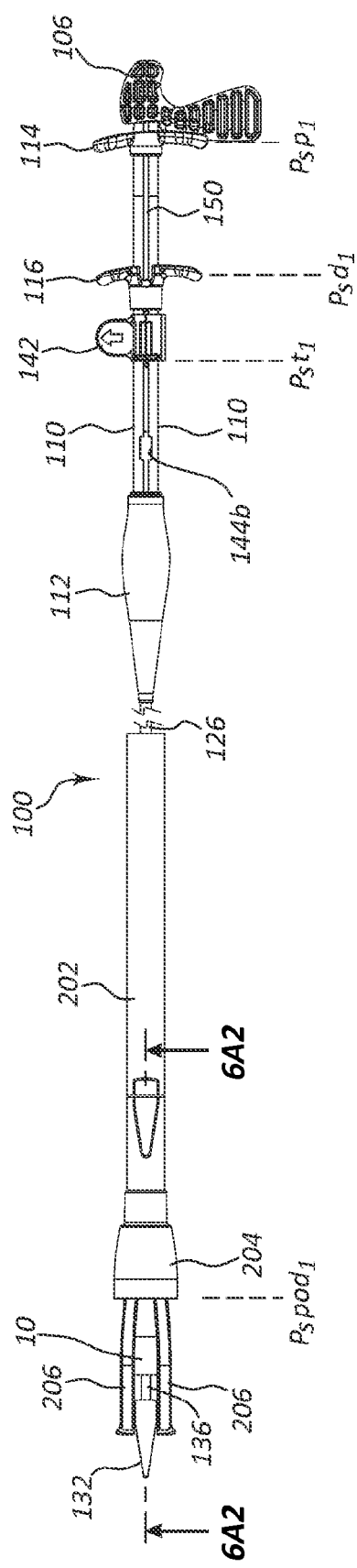
FIG. 6A1
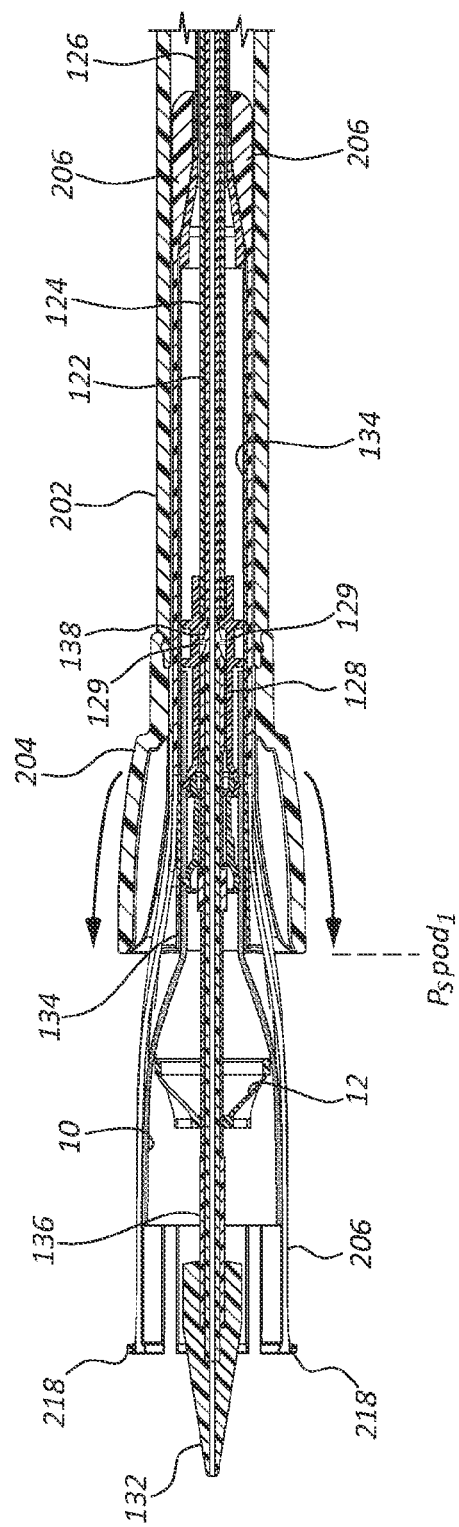
FIG. 6A2

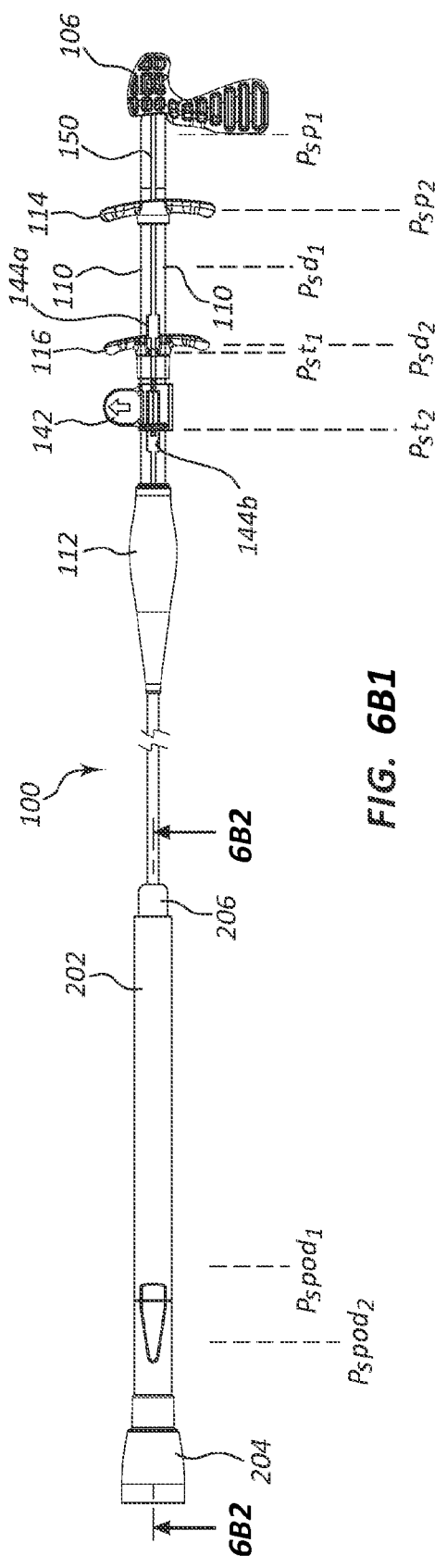
FIG. 6B1
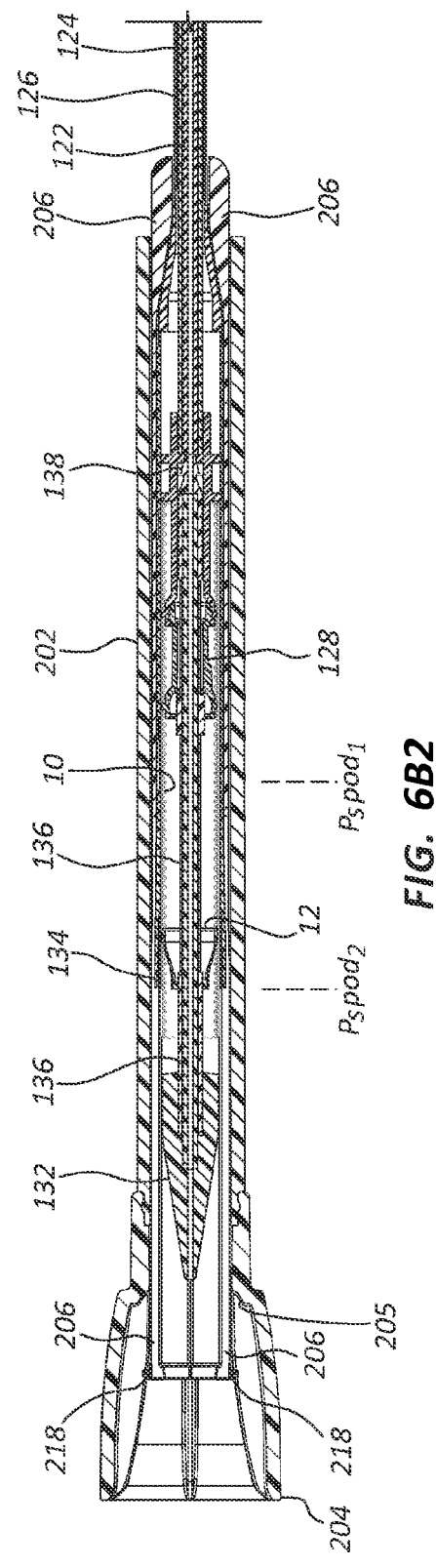
FIG. 6B2

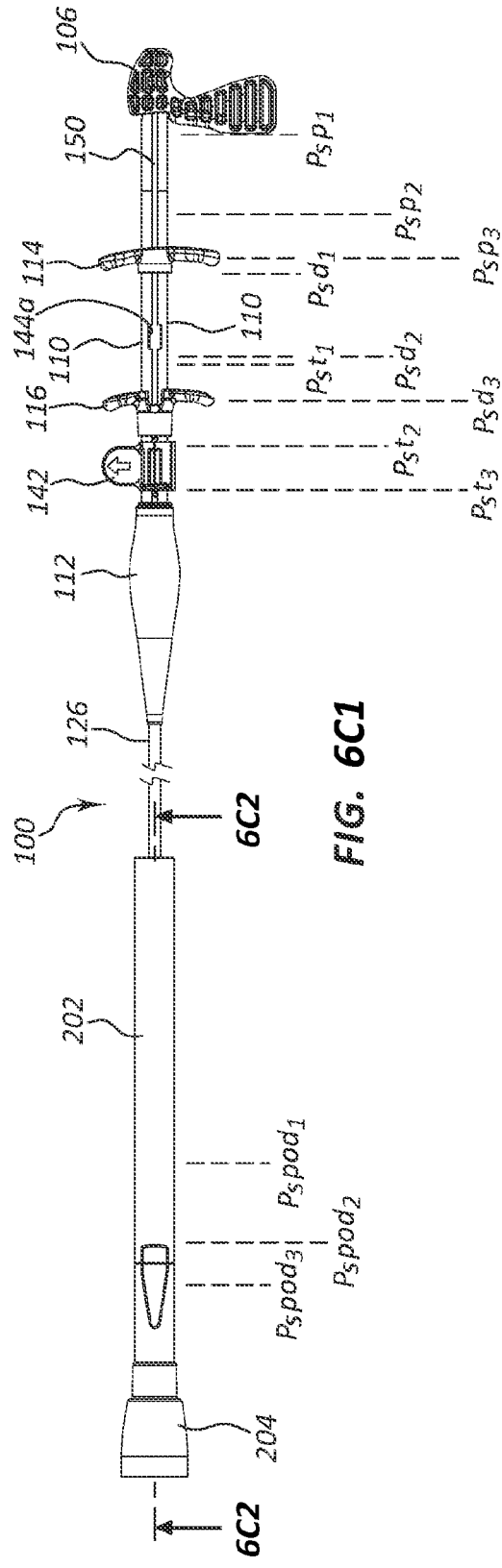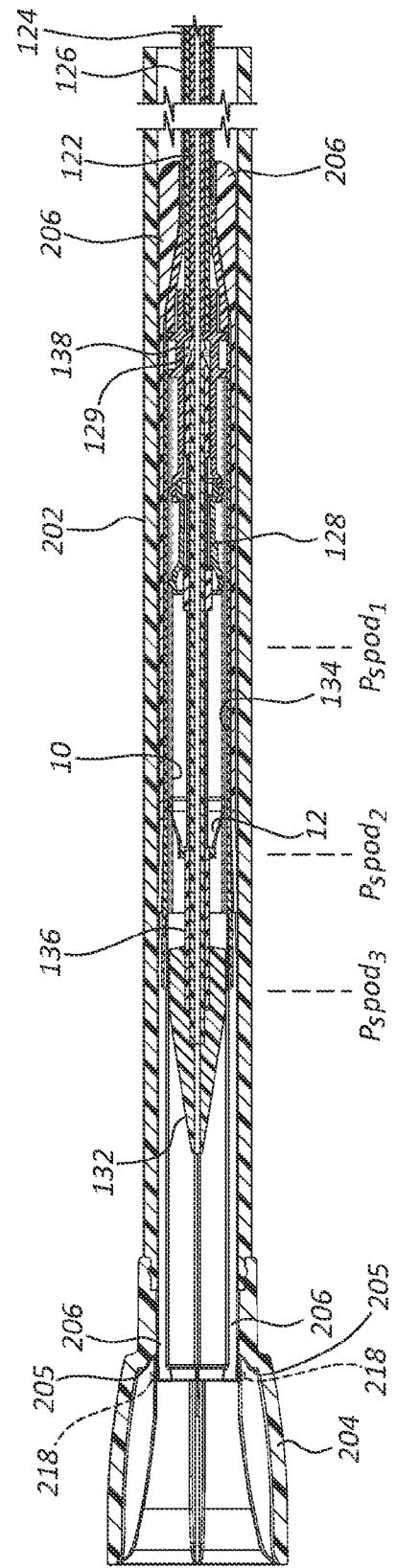

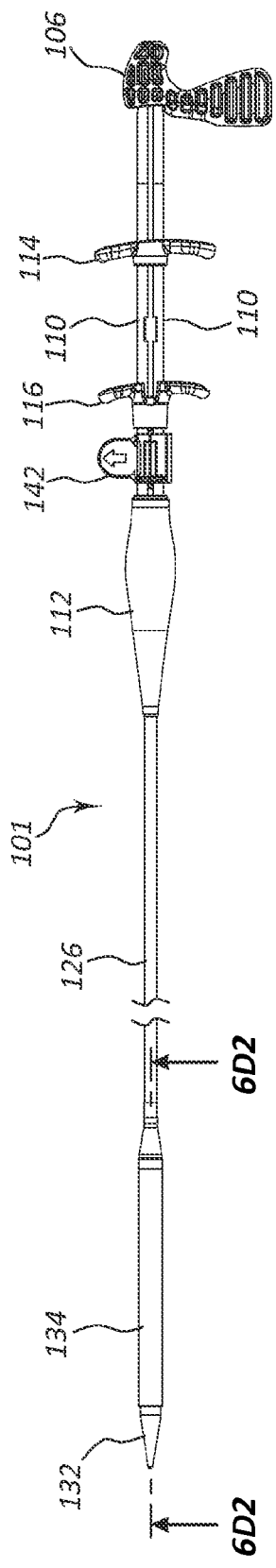
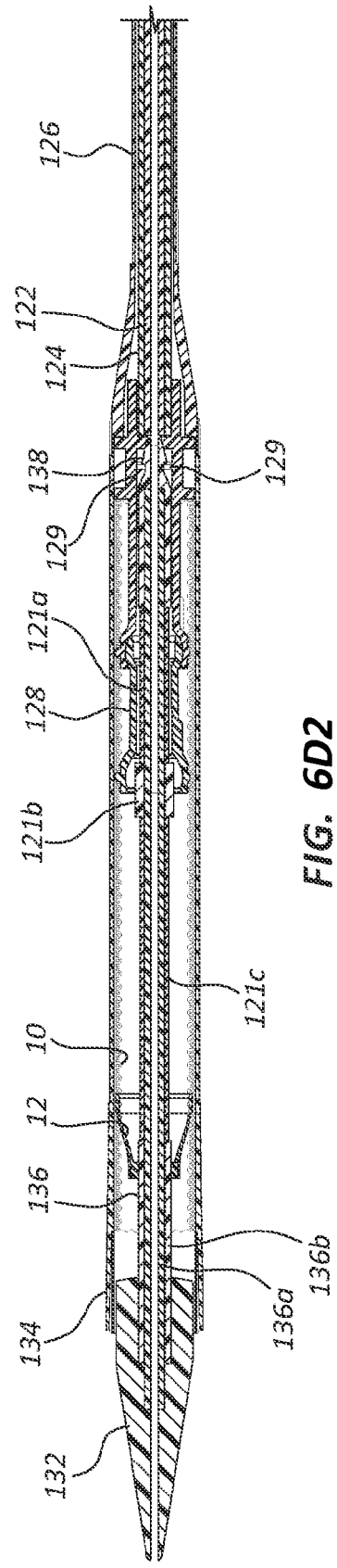
FIG. 6D1
FIG. 6D2

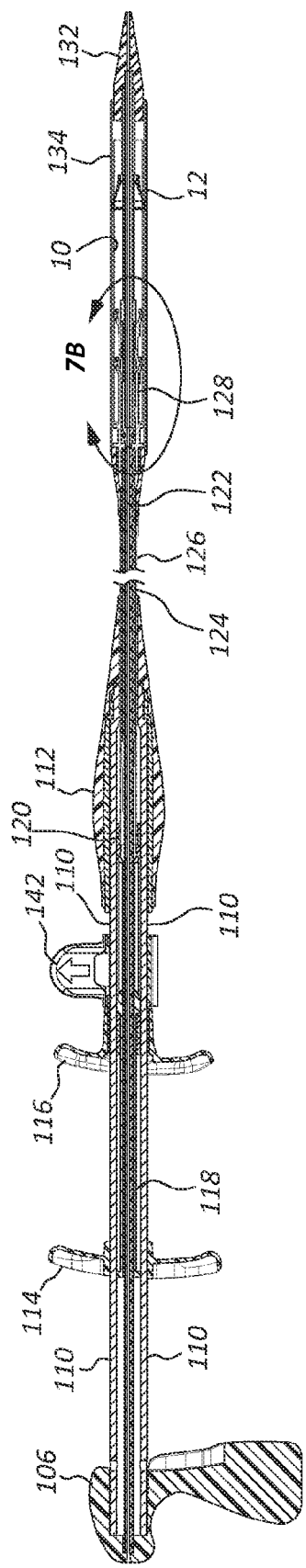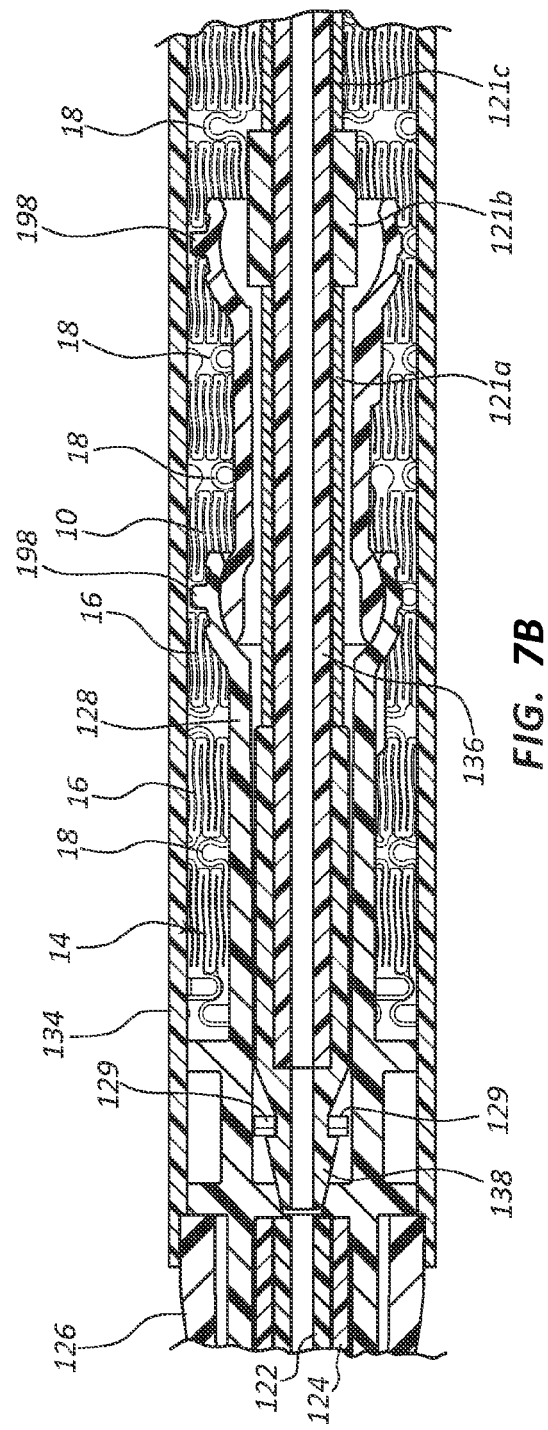
FIG. 7A
FIG. 7B

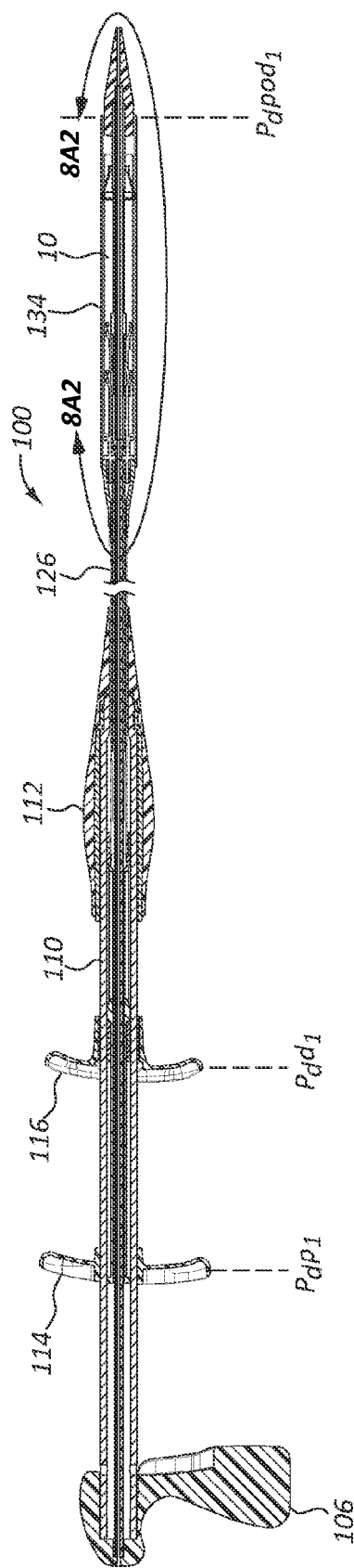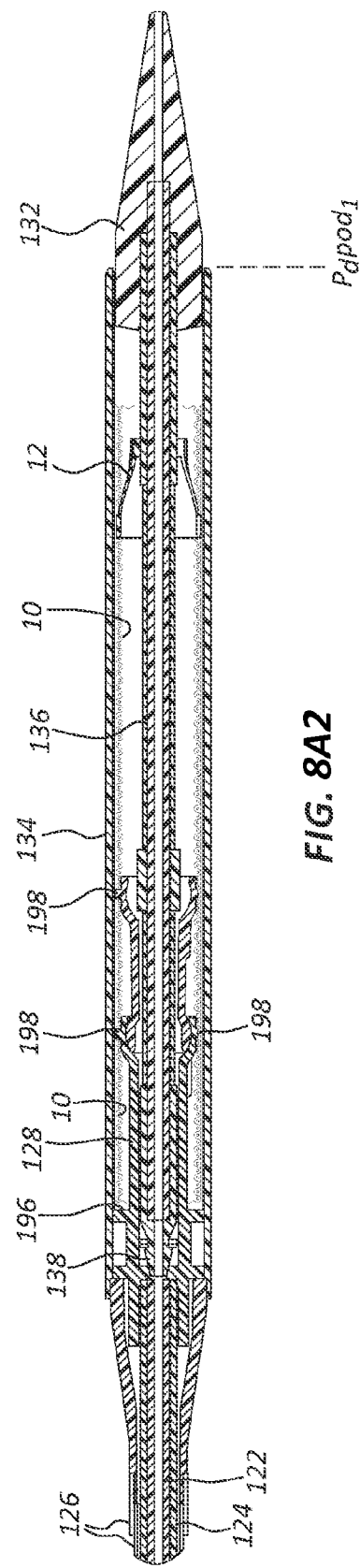
FIG. 8A1
FIG. 8A2

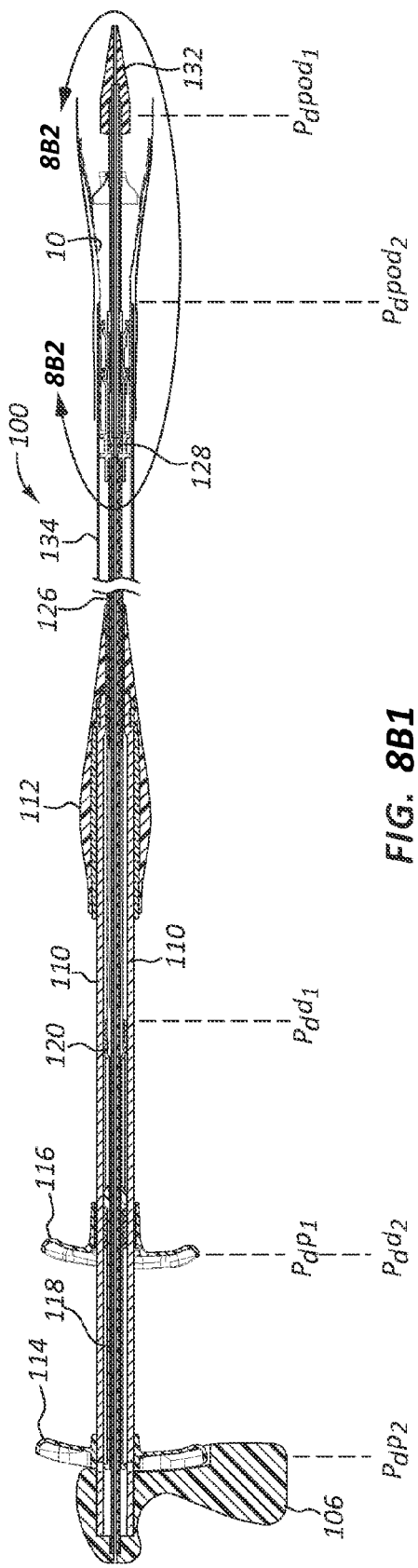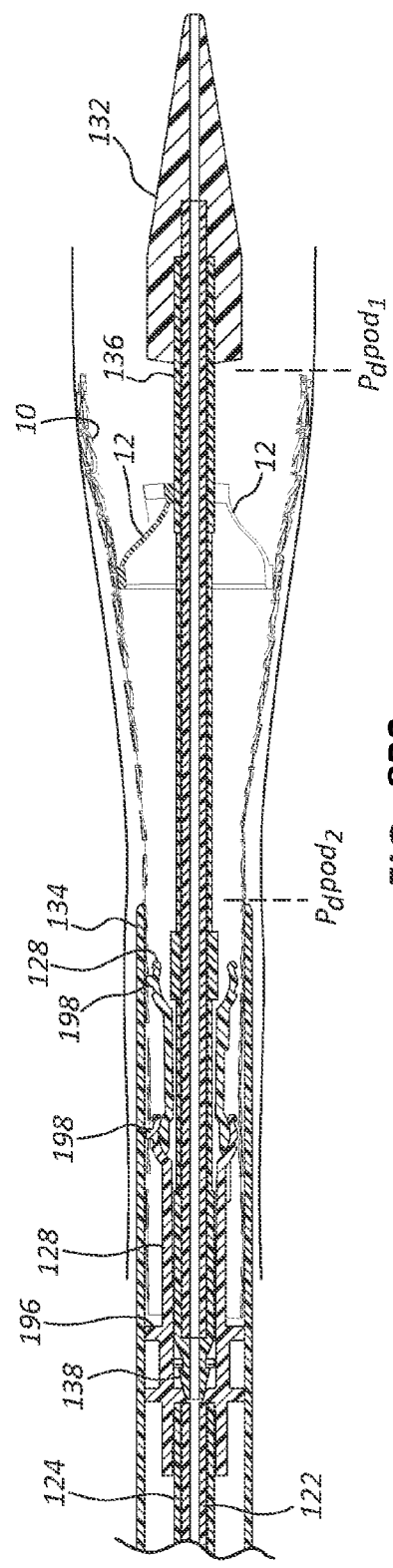
FIG. 8B1
FIG. 8B2

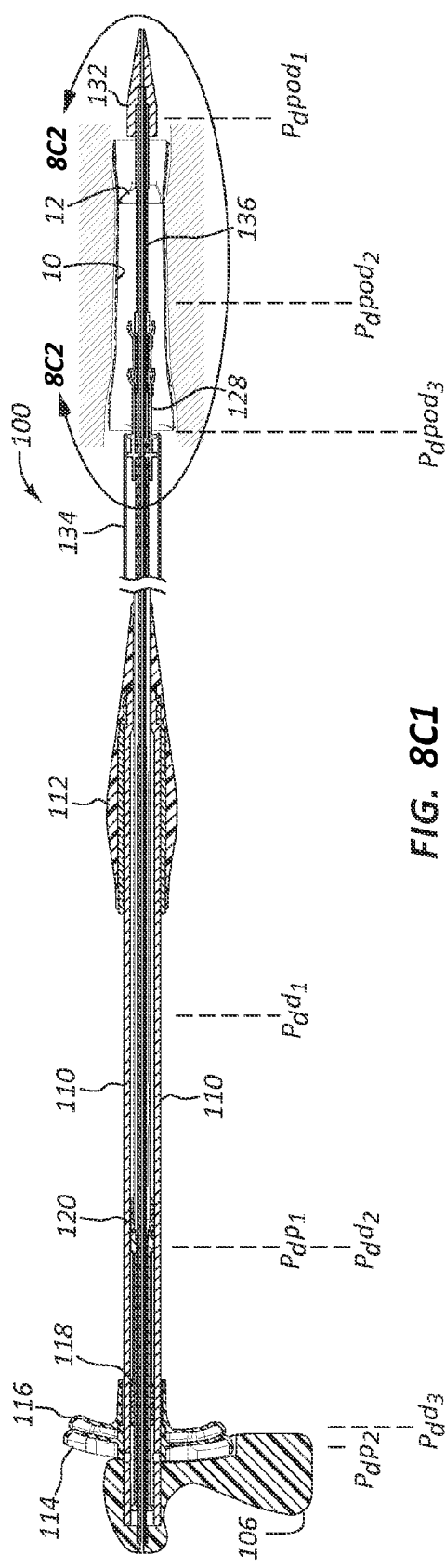
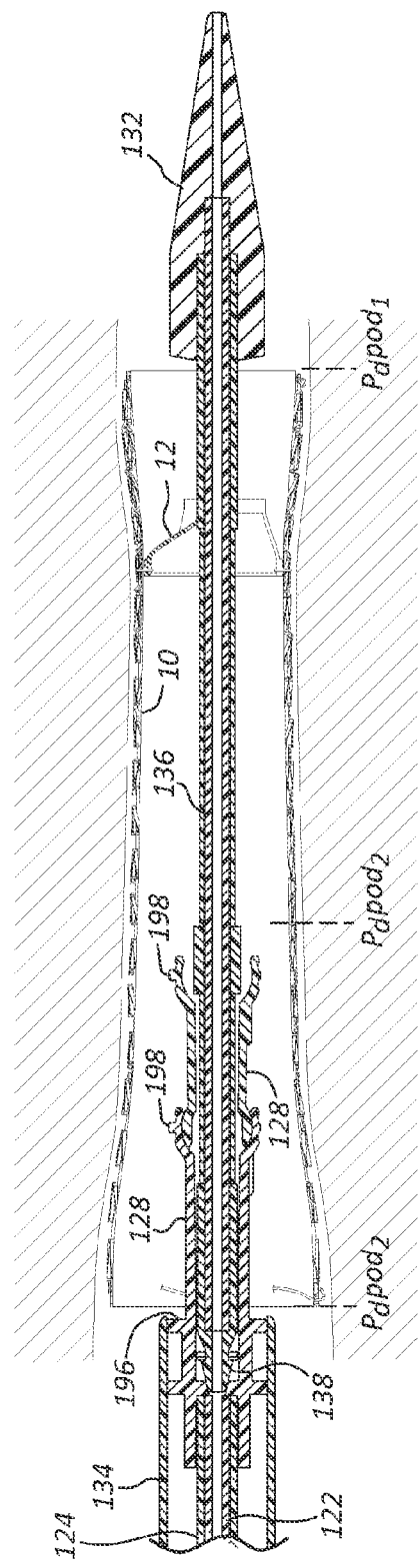
FIG. 8C1
FIG. 8C2

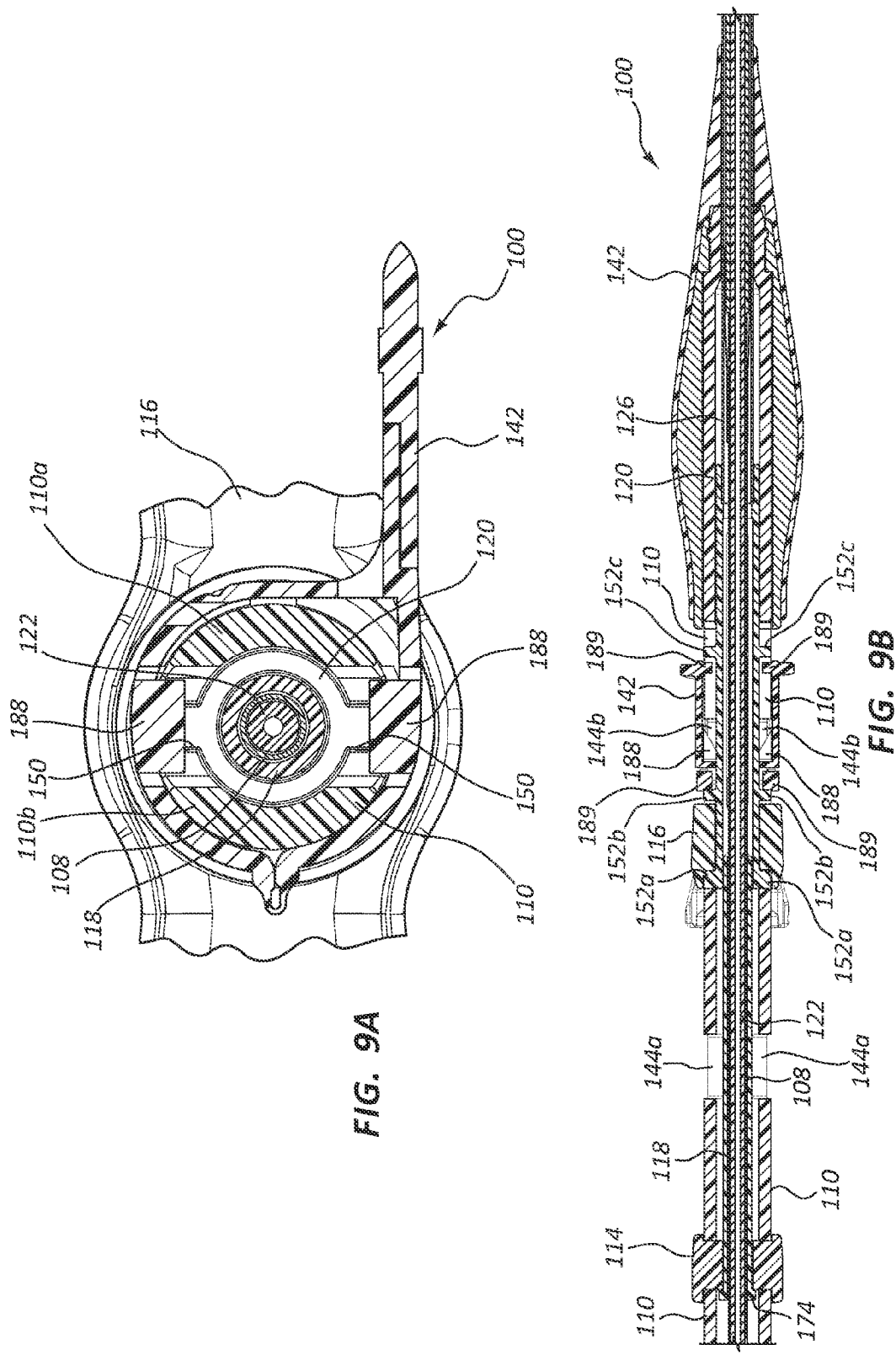

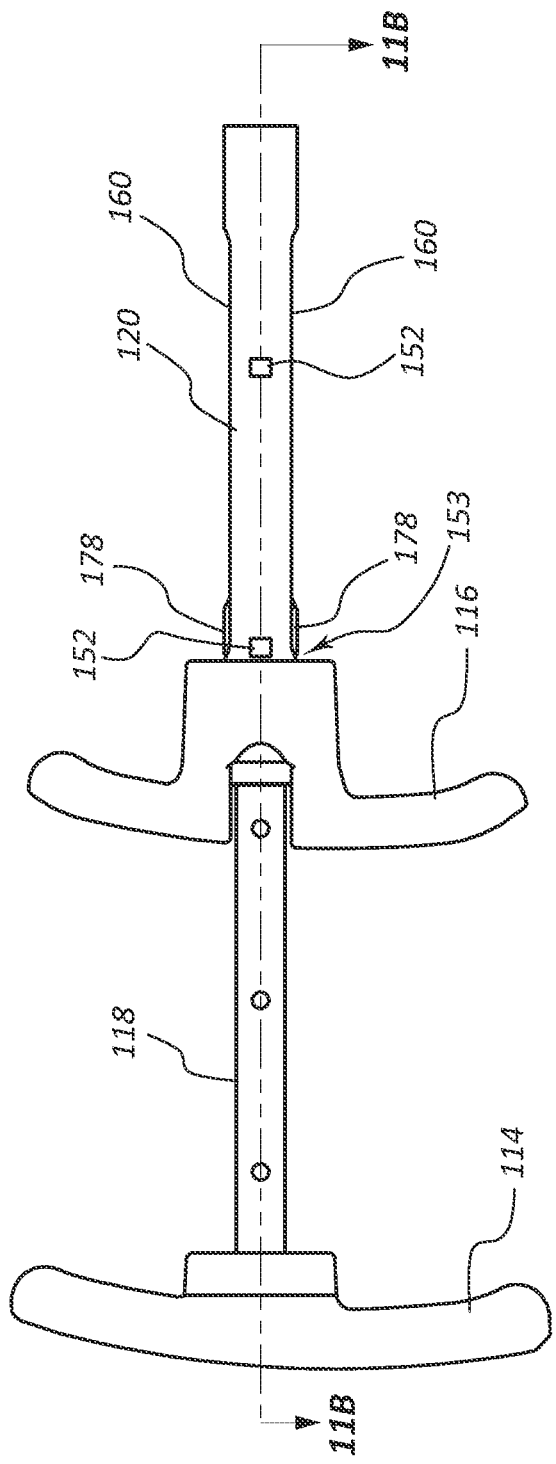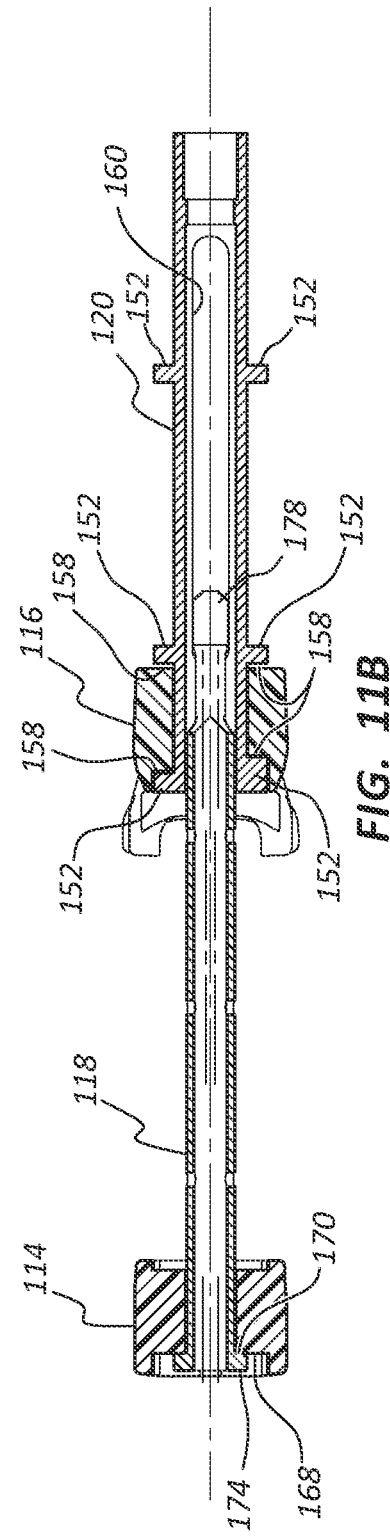
FIG. 11A
FIG. 11B

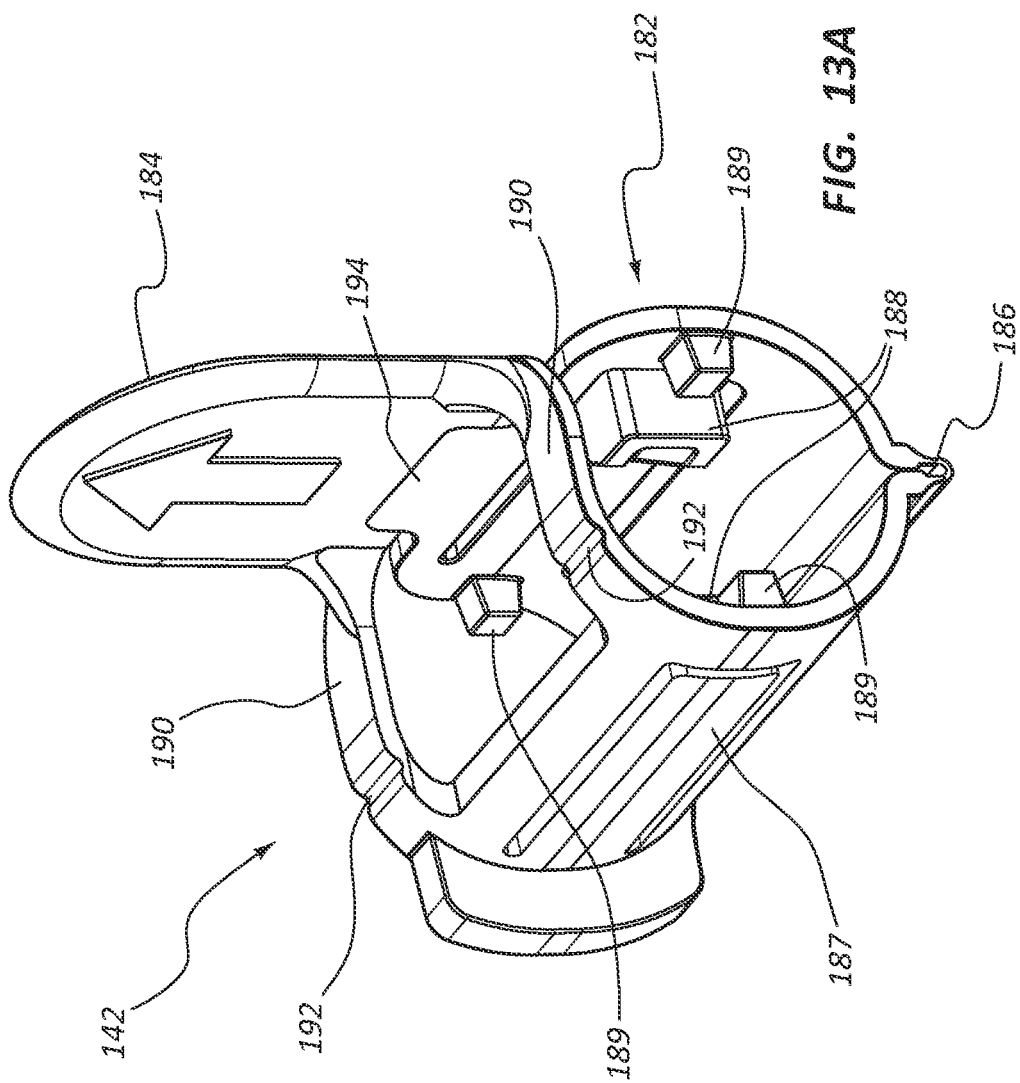

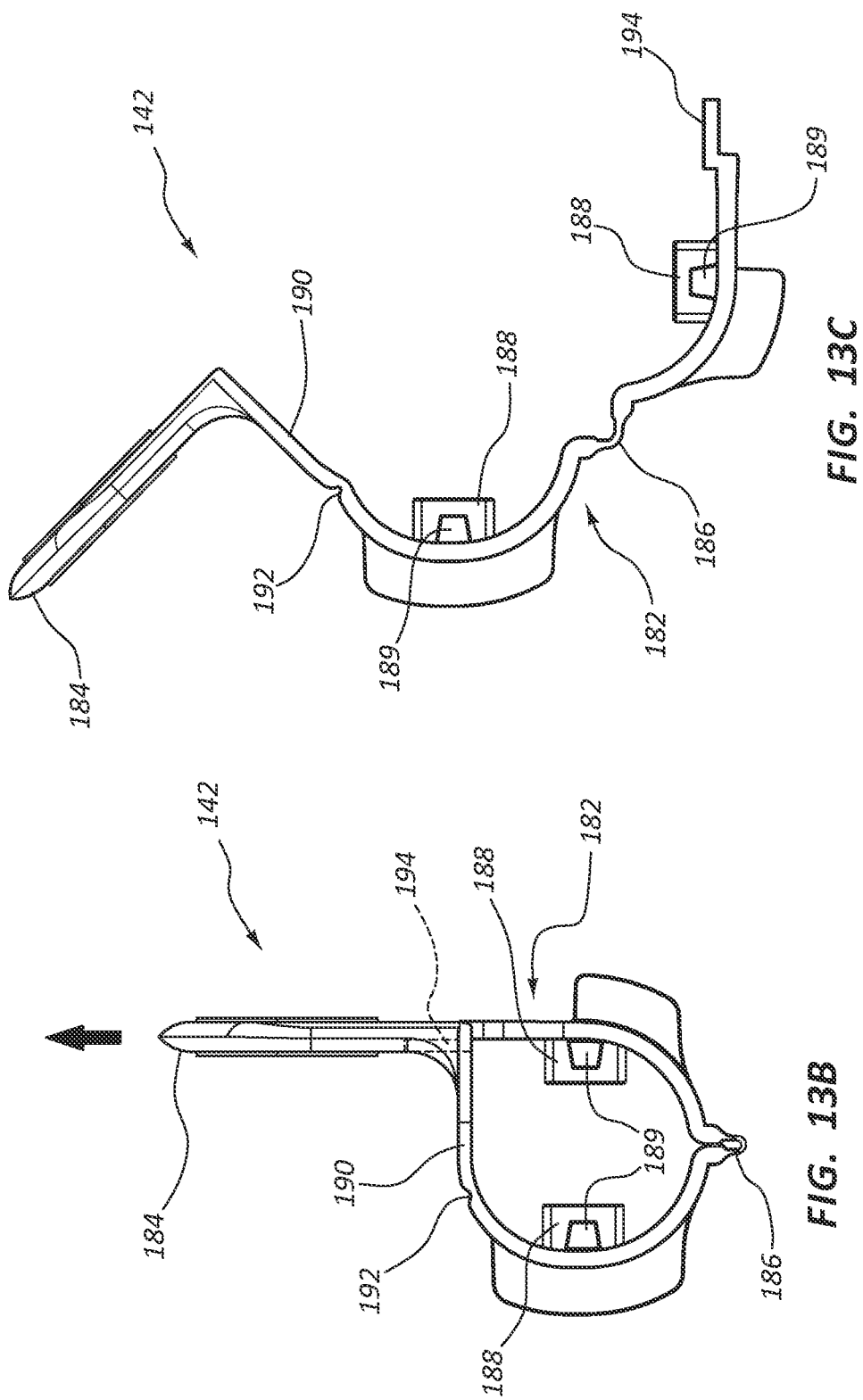

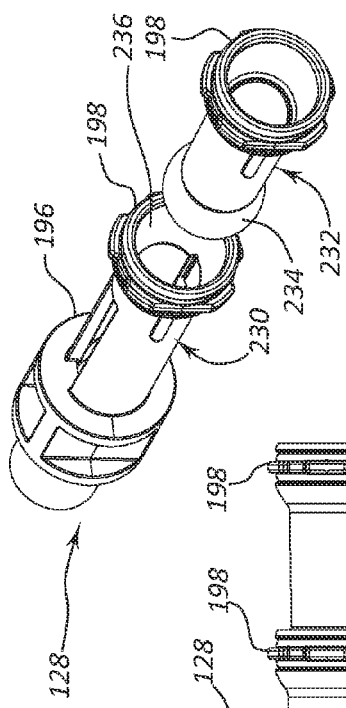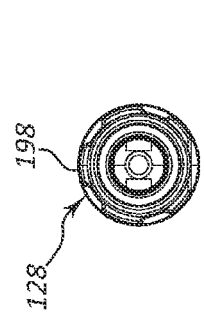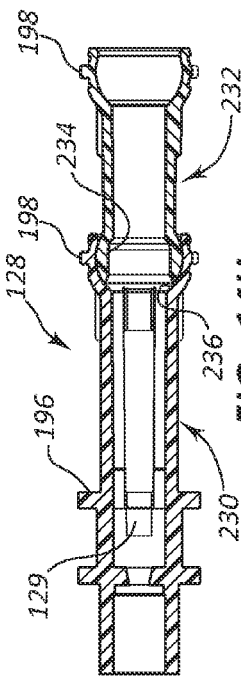
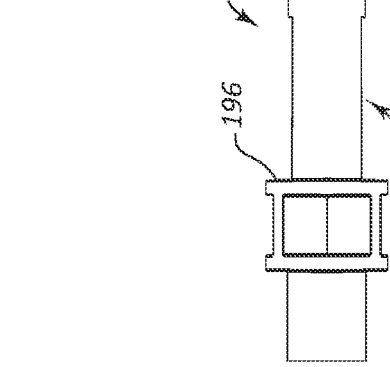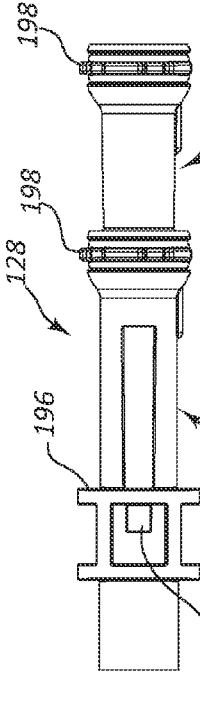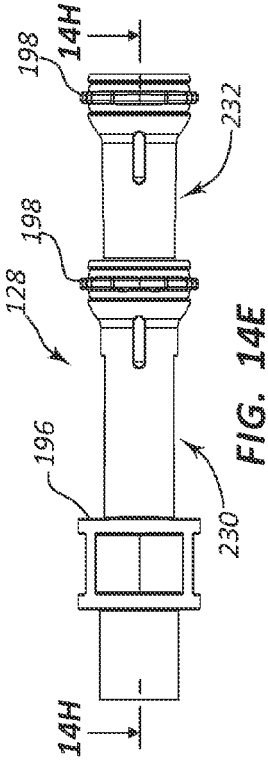
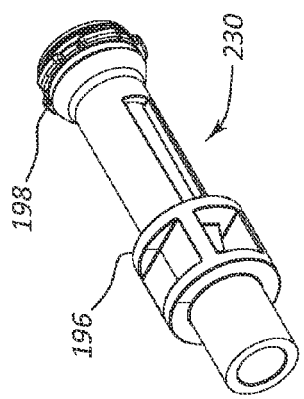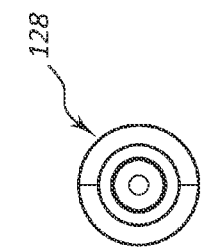

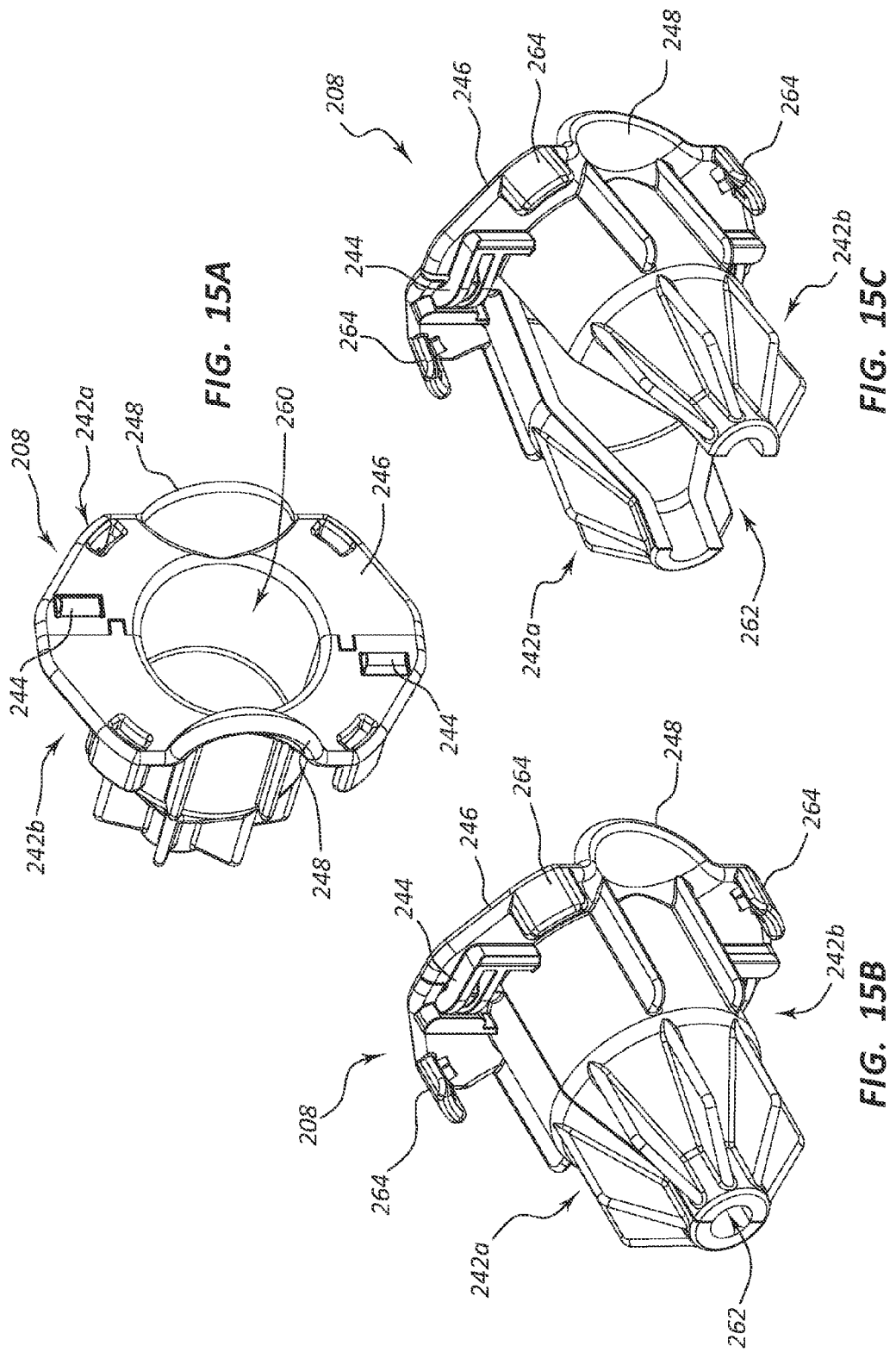

SAFETY MECHANISM FOR AN IMPLANTABLE DEVICE DEPLOYMENT APPARATUS

CROSS-REFERENCE TO RELATED APPLICATIONS

This application claims the benefit under 35 U.S.C. §119 (e) of U.S. Provisional Patent Application No. 61/553,844, entitled "STENT DELIVERY SYSTEMS AND METHODS," filed Oct. 31, 2011, and U.S. Provisional Patent Application No. 61/596,473, entitled "STENT DELIVERY SYSTEMS AND METHODS," filed Feb. 8, 2012, each of which is hereby incorporated herein by reference in its entirety.

TECHNICAL FIELD

The present disclosure is directed to systems and methods for delivering a stent to a lumen internal to a body of a patient, and more particularly to systems and methods for sheathing a stent just prior to an insertion procedure.

BRIEF DESCRIPTION OF THE DRAWINGS

The written disclosure herein describes illustrative embodiments that are non-limiting and non-exhaustive. Reference is made to certain such illustrative embodiments that are depicted in the figures, in which:

FIG. 4A is a side view of the stent delivery system of FIG. 1.

FIG. 4B is a cut-away, cross-sectional side view of the stent delivery system of FIG. 4A.

FIG. 4C is another cut-away, cross-sectional side view of the stent delivery system of FIG. 4A.

FIG. 4D1 is another cut-away, cross-sectional side view of the stent delivery system of FIG. 4A.

FIG. 4D2 is an enlargement of the cut-away, cross-sectional side view of FIG. 4D1.

FIG. 5A is a perspective view illustrating assembly of a sheathing mechanism at a distal region of the stent delivery system of FIG. 1, preparatory to performing a stent implantation procedure.

FIG. 5C is another perspective view illustrating assembly of a sheathing mechanism at a distal region of the stent delivery system of FIG. 1.

FIG. 5E1 is a perspective view illustrating the stent delivery system of FIG. 1, preparatory to sheathing.

FIG. 5E2 is an end view of a distal end of the stent delivery system of FIG. 5E1.

FIG. 5F1 is a perspective view illustrating a beginning of a sheathing action of the stent delivery system of FIG. 1, preparatory to performing a stent implantation procedure.

FIG. 5F2 is an end view of a distal end of the stent delivery system of FIG. 5F1.

FIG. 5F3 is a cross-sectional side view of a distal end of the stent delivery system of FIG. 5F1.

FIG. 5G1 is a perspective view further illustrating a sheathing action of the stent delivery system of FIG. 1.

FIG. 5G2 is an end view of a distal end of the stent delivery system of FIG. 5G1.

FIG. 5G3 is an enlarged cross-sectional side view of a distal end of the stent delivery system of FIG. 5G1.

FIG. 6A1 is a side view of the stent delivery system of FIG. 1 in a partially sheathed configuration and in a similar configuration as in FIG. 5E1.

FIG. 6A2 is an enlarged cross-sectional side view of a distal region of the stent delivery system of FIG. 6A1.

FIG. 6B1 is a side view of the stent delivery system of FIG. 1 in a partially sheathed configuration and in a similar configuration as in FIG. 5F1.

FIG. 6B2 is an enlarged, cross-sectional side view of a distal region of the stent delivery system of FIG. 6B1.

FIG. 6C1 is a side view of the stent delivery system of FIG. 1 in a partially sheathed configuration and in a similar configuration as in FIG. 5G1.

FIG. 6C2 is an enlarged, cross-sectional side view of a distal region of the stent delivery system of FIG. 6C1.

FIG. 6D1 is a side view of the stent delivery system of FIG. 1 in a fully sheathed configuration and in a similar configuration as in FIG. 5I.

FIG. 6D2 is an enlarged, cross-sectional side view of a distal region of the stent delivery system of FIG. 6D1.

FIG. 7A is a side longitudinal cross-sectional view of the stent delivery system of FIG. 1 in the fully sheathed delivery configuration.

FIG. 7B is a close-up, cross-sectional view the stent of the stent delivery system of FIG. 7A in a compressed configuration.

FIG. 8A1 is a side longitudinal cross-sectional view of the stent delivery system of FIG. 1 with the trigger safety removed.

FIG. 8A2 is a close-up, cross-sectional view of the fully sheathed stent of the stent delivery system of FIG. 8A1.

FIG. 8B1 is a side longitudinal, cross-sectional view of the stent delivery system of FIG. 1 with the proximal trigger retracted.

FIG. 8B2 is a close-up, cross-sectional view of the partially deployed stent of the stent delivery system of FIG. 8B1.

FIG. 8C1 is a side longitudinal, cross-sectional view of the stent delivery system of FIG. 1 with the distal trigger retracted.

FIG. 8C2 is a close-up, cross-sectional view of the stent of the stent delivery system of FIG. 8C1.

FIG. 9A is a transverse cross-sectional view of a portion of the stent delivery system of FIG. 1.

FIG. 9B is a longitudinal, cross-sectional view of a portion of the stent delivery system of FIG. 1.

FIG. 11A is a side view of an internal connector, a distal trigger, a floater, and a proximal trigger of the stent delivery system of FIG. 1.

FIG. 11B is a top cross-sectional view of an internal connector, a distal trigger, a floater, and a proximal trigger of the stent delivery system of FIG. 1.

FIG. 13A is a perspective view of the trigger safety of the stent delivery system of FIG. 1.

FIG. 13B is a side view of the trigger safety of the stent delivery system of FIG. 1 in a closed state.

FIG. 13C is a side view of the trigger safety of the stent delivery system of FIG. 1 in an open state.

FIG. 14A is a perspective view of a panchor of the stent delivery system of FIG. 1.

FIG. 14B is another perspective view of a panchor of the stent delivery system of FIG. 1.

FIG. 14C is a side view of a panchor of the stent delivery system of FIG. 1.

FIG. 14D is a top view of a panchor of the stent delivery system of FIG. 1.

FIG. 14E is a bottom view of a panchor of the stent delivery system of FIG. 1.

FIG. 14F is an end view of a panchor of the stent delivery system of FIG. 1.

FIG. 14G is another end view of a panchor of the stent delivery system of FIG. 1.

FIG. 14H is a cross-sectional view of a panchor of the stent delivery system of FIG. 1.

FIG. 15A is a perspective view of a tip insertion funnel of the stent delivery system of FIG. 1.

FIG. 15B is another perspective view of a tip insertion funnel of the stent delivery system of FIG. 1 in a closed state.

FIG. 15C is a perspective view of a tip insertion funnel of the stent delivery system of FIG. 1 in an open state.

DETAILED DESCRIPTION

Figure 1:
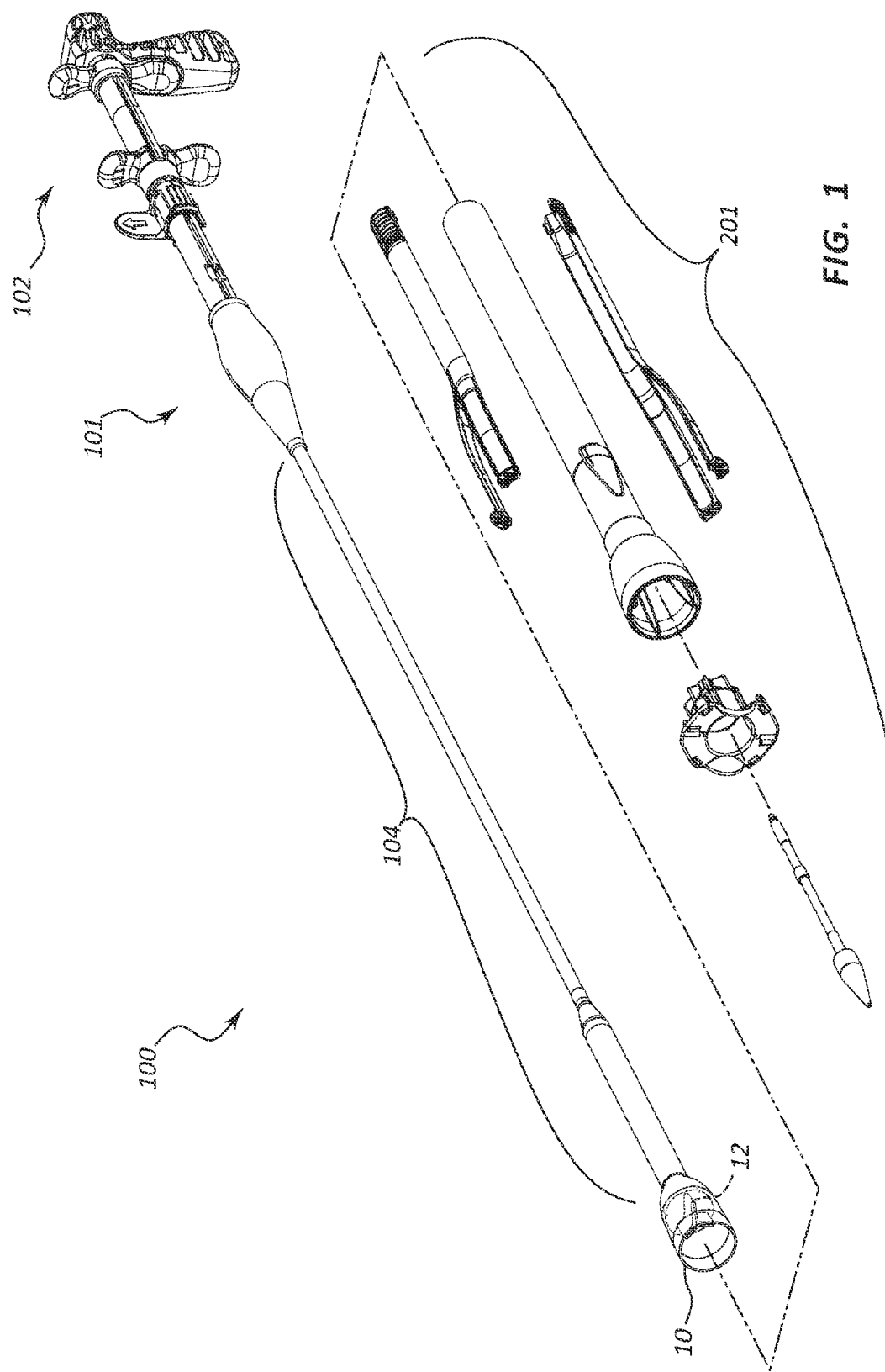
FIG. 1 is a perspective view of a stent delivery system in a partially sheathed configuration, according to one embodiment of the present disclosure.

The present disclosure relates to systems and methods for deploying a crimpable implantable device within a body of a patient. For example, the disclosed systems and methods may provide for deploying a valved stent within a lumen of a body of a patient. The disclosed embodiments may allow the implantable device to be stored and/or transported in partially sheathed (and also partially deployed) storage configuration, such that a portion of the implantable device is crimped and/or sheathed within a stent delivery device. A portion of the implantable device may also remain unsheathed and in an expanded (or uncrimped) state. In the case of a valved stent, the portion of the valved stent that includes the valve can remain unsheathed in an expanded state to prevent the valve from enduring prolonged periods of compression and deformation (e.g., during storage and/or transport) that can result in deformation of the valve.

The disclosed embodiments may further allow a practitioner to fully crimp and/or fully sheathe the implantable device and transition the delivery device into a delivery configuration just prior to delivery of the implantable device to a desired location within a target lumen. The disclosed embodiments may further allow deployment of the implantable device to an expanded fully deployed state.

Implantable medical devices are valuable tools of modern medicine. In general, an implantable device is a device or structure configured to be inserted or embedded into a patient for a variety of functions. Implantable devices include stents, filters, markers, drug delivery devices, valves, and monitors.

Stents are implantable devices that are inserted into body lumina, such as vessels or passages, to keep the lumen open and prevent closure due to a stricture, external compression, or internal obstruction. Stents are commonly used to keep blood vessels open in the coronary arteries, and they are frequently inserted into the ureters to maintain drainage from the kidneys, the bile duct for pancreatic cancer or cholangiocarcinoma, or the esophagus or airways for strictures or cancer.

In order to serve a desired function, an implantable device should be delivered precisely and oriented correctly. Improper installation can lead to several adverse complications, including tissue luminal inflammation and tissue granulation. In order to facilitate the delivery of implantable devices, delivery devices, such as endoscopes and catheters, have been utilized to deploy implantable devices more precisely.

Delivery devices vary in shape and structure. However, in general, a delivery device may include a handle and one or more movable tubular members extending from the handle. The delivery device may further include a deployment mechanism for moving or operating the tubular members between positions. The one or more moveable tubular members typically include an inner tubular member disposed within an outer tubular member or sheath. The outer tubular member is typically shorter than the inner tubular member and movable relative to the inner tubular member. A distal region of the outer tubular member generally surrounds the implantable device. In the case of a stent, the outer tubular member may maintain the stent sheathed in a crimped state in the sheathed delivery configuration, while a distal region of the inner tubular member is surrounded by the stent. Once the sheathed stent is properly positioned at a target deployment site, the outer tubular member may be retracted to deploy the stent and allow the stent to radially expand.

Many presently available delivery devices require an implantable device to be fully crimped and/or sheathed by special equipment prior to storage and/or transport and prior to deployment for use, for example in treating a lumen of a body of a patient. As used herein, the terms "crimp" and "crimping" refer to compressing or drawing a crimpable implantable device inward, radial toward a longitudinal axis of the implantable device, to bring the implantable device to approximately an original or initial size. Crimping may occur independent from and with limited compression or expansion longitudinally along a longitudinal axis of the implantable device. In other words, crimping may involve limited or no change in a longitudinal dimension of the implantable device.

Some implantable devices are designed to be sheathed (or re-sheathed) for removal from the body, yet such implantable devices may be configured such that they cannot be subsequently deployed for use without properly being crimped before being sheathed. A stent that is re-sheathed may not necessarily be crimped or otherwise returned to a crimped state. The re-sheathing process may damage, deform, or otherwise alter the structural integrity or other characteristic of the implantable device in such a way as to limit the usability of the implantable device when subsequently deployed, thereby preventing subsequent use.

Sheathing some implantable devices in a manner that avoids damage to the structural integrity of the stent, to enable subsequent use, can be particularly challenging. For example, some embodiments of stents, such as are disclosed in U.S. patent application Ser. No. 13/153,150, entitled "ESOPHOGEAL STENT," which is hereby incorporated by reference herein in its entirety, may comprise a support or scaffolding structure formed of a plurality of rows of struts or legs oriented about an outer circumference of the stent and connected by a plurality of connectors extending longitudinally with a longitudinal axis of the stent. Additionally, the stent or other implantable device may comprise a variety of components, and the parameters of these components—such as shape, length, thickness, position, etc.—may greatly vary to provide a stent with certain properties. The arrangement of these components may make sheathing of the stent quite difficult. Protruding components of the scaffolding structure may prevent the stent, or portions of the stent from being "self-sheathing" with traditional equipment. The components may need to be crimped prior to sheathing. Prior to the embodiments of the present disclosure, such embodiments of stents could not be crimped and/or sheathed outside of a factory setting in a manner that would render the stent in a useable state for subsequent deployment and use.

Traditional delivery devices, which require that the implantable device be fully crimped and sheathed prior to storage and/or transport for eventual use, can be problematic to use to deliver (or deploy) a valved stent. A valve of a valved stent may be formed of a polymer material that may be easily deformable by applying a constant force or otherwise maintaining the valve in a deformed state for a prolonged period of time.

For example, embodiments of a valved stent are disclosed in U.S. patent applicaiton Ser. No. 13/285,358, entitled "ESOPHOGEAL STENT WITH VALVE," which is hereby incorporated by reference herein in its entirety, and may include a valve formed of a polymer. Because polymers lack a well defined crystalline structure, they can easily undergo a glass transition at a given glass transition temperature $T_g$ when cooled (or heated) and, thereby, exhibit physical properties of both a solid and a liquid. Specifically, a polymer can be cooled into a desired shape and may hold that shape. However, the polymer can easily be reshaped or plastically deformed in response to pressure or stress, particularly if also exposed to temperatures approaching or above the $T_g$ of the polymer. If the $T_g$ is relatively low (e.g., 114 degrees F.), as in the case for some polymers, plastic deformation occurs easily. A polymer valve of a valved stent that is compressed and deformed in a delivery configuration of the stent for a prolonged period of time (e.g., during storage and/or transport) can permanently deform. The deformed valve may not function properly and thus remain in a defective and unusable state. Accordingly, a delivery device that can only be used by a practitioner if the stent arrives fully crimped and/or sheathed may not be an effective delivery device for a valved stent. A delivery device that can be transported with the valve in a natural operable configuration, and not subject to forces that may induce plastic deformation, may be desirable.

Also, because delivery devices are commonly designed to facilitate easy deployment, inadvertent or accidental deployment may easily occur. Safety mechanisms to secure the outer tubular member relative to the inner tubular member typically comprise a pin passing through both the outer tubular member and the inner tubular member. These "pin-type" safety mechanisms can be difficult to operate or even ineffective in some instances. For example, a "pin-type" safety mechanism does not allow distal movement of a trigger and/or an outer sheath to enable sheathing a stent, while also restricting proximal movement of the trigger to prevent inadvertent deployment.

The present disclosure is directed to stent delivery systems addressing various shortcomings of presently available stent delivery devices. In particular, the present disclosure provides a stent delivery system that may enable a practitioner to fully sheath a stent that may be merely partially sheathed or even completely unsheathed and in an expanded configuration. The stent delivery system may have a plurality of triggers and a trigger safety to prevent accidental or inadvertent deployment. A stent delivery system according to the present disclosure may also have a flexible pusher/anchor ("panchor") component configured to engage the sheathed stent to restrict movement of the sheathed stent both proximally and distally relative to the delivery device.

Although described in terms of delivering an esophageal stent with a valve, a person having ordinary skill in the art, with the aid of the present disclosure, will readily appreciate that the disclosed delivery systems can be used to deliver a variety of crimpable implantable devices, including but not limited to stents, filters, markers, drug delivery devices, valves, and monitors. In one embodiment, the present disclosure provides an esophageal valved stent delivery system. The present disclosure is also applicable to a variety of stents designed for a variety of applications, for example, biliary stents, bronchial stents, tracheal stents, colonic/duodenal stents, and so on. In another embodiment, the present disclosure may provide a heart replacement valve delivery system. In other embodiments, the present disclosure may provide a delivery system for other crimpable valves. In still other embodiments, the present disclosure may provide a delivery system for a variety of crimpable devices.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. As will also be readily understood, the components of the embodiments as generally described and illustrated in the figures herein could be arranged and designed in a wide variety of different configurations.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device. As used herein, the proximal end of a medical device is the end nearest a practitioner during use, while the distal end is the opposite end. For example, the proximal end of a stent delivery device refers to the end having the handle and disposed nearest a point of contact with the practitioner when the stent delivery device is in use by a practitioner.

FIG. 1 is a perspective view of a stent delivery system 100 in a partially sheathed configuration, according to one embodiment of the present disclosure. The stent delivery system 100 may comprise a stent delivery device 101 and a sheathing mechanism 201. The stent delivery device 101 may comprise a trigger assembly 102 and a tubular member 104. The tubular member 104 is configured to house a crimped and/or sheathed stent 10 for delivery to a target location within a patient's body, such as within a lumen. The trigger assembly 102 may enable a practitioner to deploy the stent 10. The sheathing mechanism 201 may enable a practitioner to fully sheath a partially sheathed stent 10 shortly prior to a procedure in which the stent 10 may be deployed in a lumen of a patient. In the illustrated embodiment, the stent 10 may be a valved stent having a valve 12. The stent 10 may have a length, for example, of 100 mm, such that it could be deployed with a two-stage, two-trigger deployment mechanism.

The valved stent 10 may be an esophageal stent. Some patients suffer from an obstruction of the esophagus at or near the lower esophageal sphincter, which is the valve at the opening of the esophagus into the stomach. The lower esophageal sphincter prevents stomach acid and other gastric fluids from travelling up the esophagus, particularly when a person is lying down or in a prone position. If a stent is positioned near or through the portion of the esophagus where the lower esophageal sphincter is located, the stent may prevent proper functioning of the lower esophageal sphincter. Without a prosthetic valve coupled in the stent to prevent migration of gastric fluids up the esophagus, the gastric fluids can work their way into the lungs, for example, while the person is sleeping. An individual without a properly functioning valve at the opening between the stomach and esophagus can aspirate gastric fluids while sleeping in a recumbent or lying position (e.g., supine, prone, lateral recumbent) and die from asphyxiation. The stent 10 with a valve 12 can be positioned at the opening of the esophagus into the stomach and the valve 12 can function to allow food to pass in one direction but prevent passage of gastric fluids in an opposite direction.

The partially sheathed configuration of the stent delivery system 100 may be a storage and/or transport configuration. A portion of the stent 10 may remain uncrimped and/or unsheathed. The valve 12 may be positioned in an uncrimped and/or an unsheathed portion of the stent 10 that is in a partially sheathed configuration. The unsheathed portion of the stent 10 may remain in an uncrimped (or expanded) state. Therefore, the valve can be maintained in an operational or natural (e.g., undeformed) state during, for example, storage and/or transport, until just before implantation of the stent 10 in a lumen of a patient. Also, the stent 10 may be partially sheathed to facilitate fully sheathing the stent 10 to transition to a fully sheathed delivery configuration.

Figure 2:
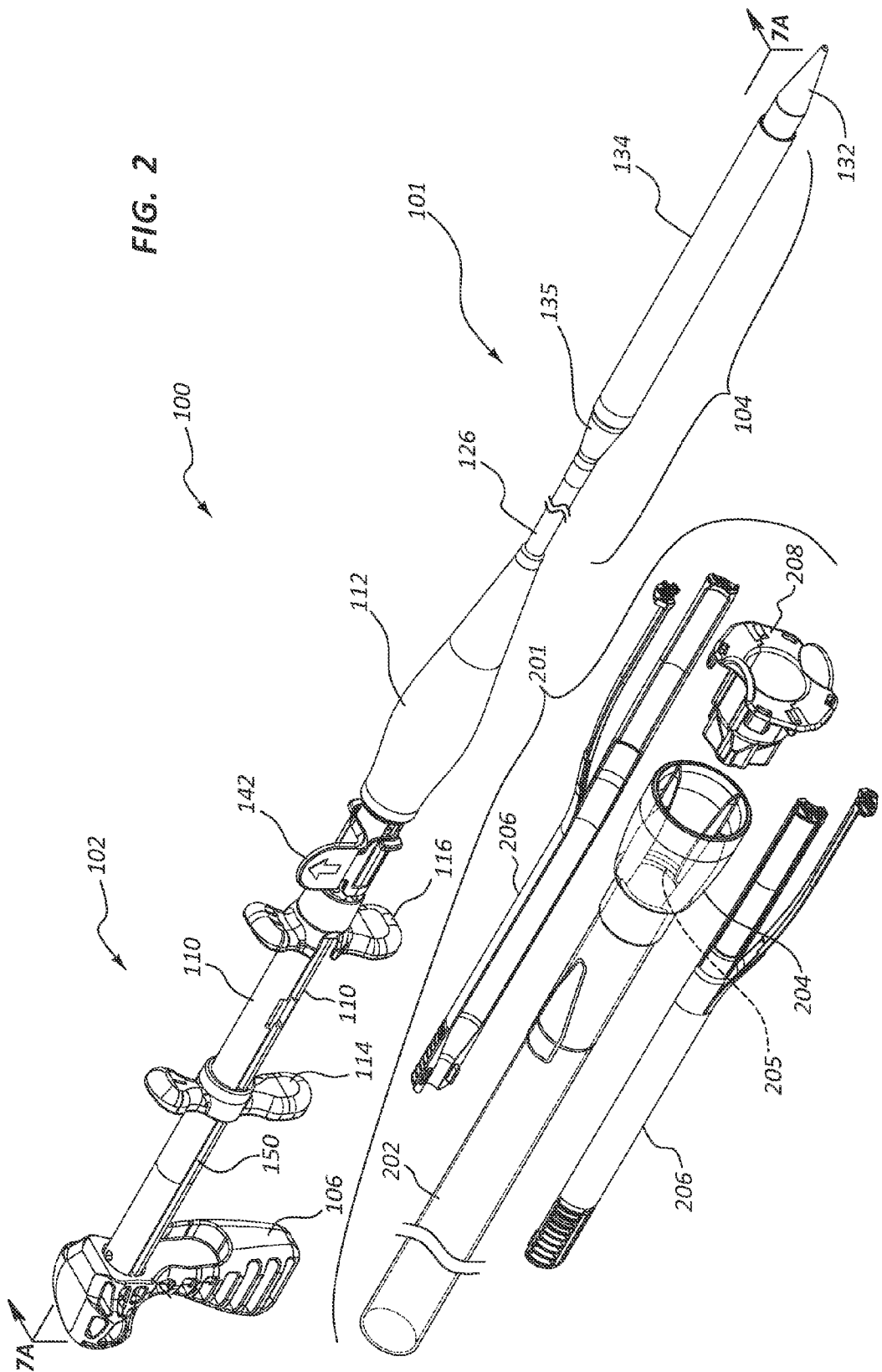
FIG. 2 is a closer perspective view of the stent delivery system of FIG. 1 in a fully sheathed delivery configuration.

FIG. 2 provides a closer perspective view of the stent delivery system 100 in the fully sheathed delivery configuration. The tubular member 104 of the stent delivery device 101 may include an outer sheath 126 coupled to the trigger assembly 102. The outer sheath 126 may include a pod 134 at the distal end to enclose or sheathe the stent 10 in a crimped state. In FIG. 2, the stent 10 is not shown because it is fully crimped and fully sheathed within the pod 134. The trigger assembly 102 may include a plurality of triggers 114, 116 that are configured to be serially retracted (e.g., pulled) toward a handle 106 to retract the outer sheath 126 and provide staged release (or deployment) of the stent 10. The triggers 114, 116 may be supported by outer supports 110. A proximal trigger 114 may be pulled proximally, toward the handle 106, to partially deploy the stent. A distal trigger 116 may then be pulled proximally, toward the handle 106 and the proximal trigger 114, to complete deployment of the stent 10.

The serial retraction of proximal trigger 114 and then the distal trigger 116 to provide a staged deployment of the stent 10 may occur in a manner such that retracting the proximal trigger 114 moves the distal trigger 116 and the outer sheath 126 proximally and longitudinally relative to an inner member, from a first position to a second position to partially unsheathe and deploy the stent 10. Subsequent retraction of the distal trigger 116 moves the outer sheath 126 proximally and longitudinally relative to the inner member from the second position to a third position to fully unsheathe and deploy the stent 10. Deployment of the stent 10 will be described in greater detail below with reference to FIGS. 8A1-8A2, 8B1-8B2, 8C1-8C2, and 8D.

One or more trigger guide slots 150 in the outer supports 110 and corresponding protrusions or trigger guides (not shown) on the triggers 114, 116 may guide longitudinal movement of the triggers 114, 116. A trigger safety 142 may inhibit operation of the trigger assembly 102 to restrict deployment of a sheathed stent 10. More specifically, the trigger safety 142 may limit proximal movement of the proximal trigger 114 and the distal trigger 116, thereby restricting deployment of the stent 10. By restricting proximal movement of the triggers 114, 116, the trigger safety 142 may guard against inadvertent or accidental deployment of the stent 10.

A sheathing grip 112 may provide a handle that can be grasped during sheathing of the stent 10. The sheathing grip 112 can be grasped with a first hand while the sheathing mechanism 201 may be grasped with a second hand. With the first hand, the sheathing grip 112 may be pulled, pushed, or otherwise forced away from the sheathing mechanism 201 during a sheathing action to crimp and fully sheathe the stent 10. Similarly, the second hand may push, pull, or otherwise force the sheathing mechanism 201 away from the sheathing grip 112 during a sheathing action.

The sheathing mechanism 201 is designed for the user to perform a sheathing action to sheathe the stent 10. The sheathing action may initiate two actions relative to the stent 10. A first action is to crimp the stent 10 to a diameter that approximates the inner diameter of the pod 134. By virtue of crimping, a second action of sliding the pod 134 over the crimped stent 10 is facilitated. As can be appreciated, a portion of the stent 10, but less than all, may be crimped (or compressed) at a given time and the pod 134 may be slid over (to sheathe) that portion before or while a next portion of the stent 10 may be crimped. The crimping action need not be completed for the entire stent 10 prior to beginning the sliding of the pod 134. The stent 10 can be gradually crimped and the sliding of the pod 134 may occur as the stent 10 is crimped, thereby gradually sheathing crimped portions of the stent 10. In other words, crimping and sheathing of the stent 10 may occur contemporaneously, or substantially contemporaneously, in a single motion and/or action.

The sheathing mechanism 201 may include a sheathing tube 202, a sheathing funnel 204, sheathing fingers 206, a tip insertion funnel 208, and a tip 132. As will be described in more detail below, the components of the sheathing mechanism 201 are assembled at a distal end of the tubular member 104, around the distal end of the outer sheath 126 or the pod 134, and facilitate sheathing of the stent 104. The sheathing funnel 204 and/or the sheathing tube interact with the sheathing fingers 206 and/or the stent 10 to crimp the stent 10. The crimping of the stent 10 compresses the stent 10 to a crimped configuration over which the pod 134 can slide.

The sheathing tube 202 and/or the sheathing funnel 204 may be a translational member that is axially displaceable relative to the tubular member 104 of the delivery device 100. The translational member may be configured to translate axial movement of the translational member in a distal direction along the tubular member 104 into radial force to compress and thereby crimp the unsheathed portion of the stent 10. For example, the sheathing funnel 204 may interact with the sheathing fingers 206 during the sheathing action. The internal taper of the sheathing funnel 204 may interact with a ramped surface of the sheathing fingers 206. The angle of the sheathing fingers 206 combined with the internal taper of the sheathing funnel 204 may translate axial movement of the sheathing tube 202 and sheathing funnel 204 into a radial force inward that may compress the stent 10 as the sheathing tube 202 is advanced distally by the user. As the sheathing funnel 204 and sheathing tube 202 advances distally, the stent 10 is compressed gradually until the stent 10 is crimped and/or until an outer diameter of the stent 10 approximates the inner diameter of the stent pod 134. A collar 205 may be disposed within the sheathing tube 202 and/or sheathing funnel 204 to engage the sheathing fingers 206 and thereby facilitate sheathing. Sheathing of the stent 10 will be described in greater detail below with reference to FIGS. 6A1-6A2, 6B1-6B2, 6C1-6C2, and 6D1-6D2.

Figure 3:
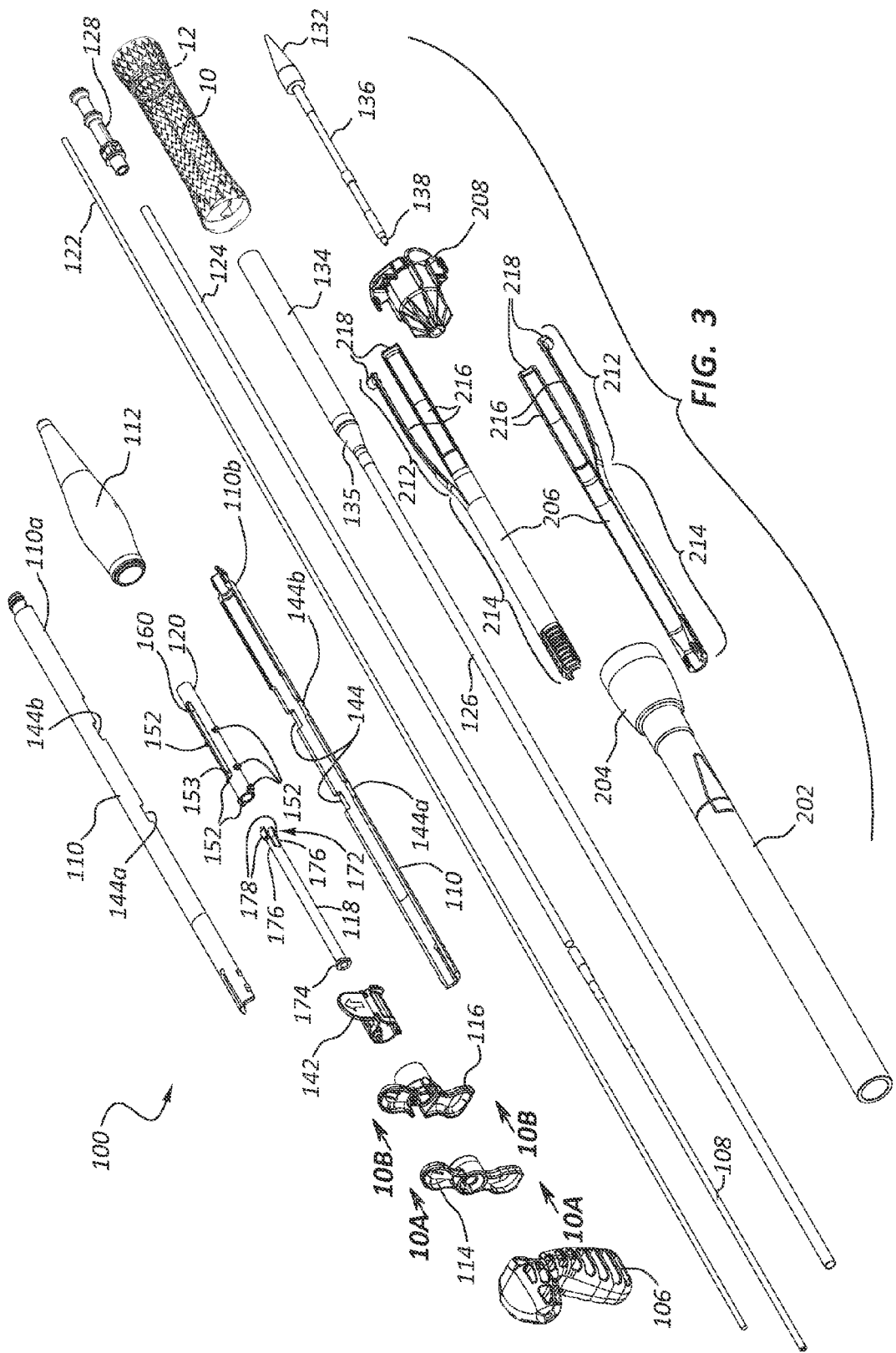
FIG. 3 is an exploded view of the stent delivery system of FIG. 1.

FIG. 3 is an exploded view of the stent delivery system 100. FIGS. 4A-4B, 4C and 4D1-4D2 are partially exploded, cut away, and/or cross-sectional side views of the stent delivery system 100. Referring collectively to FIGS. 3 and 4A-4B, 4C and 4D1-4D2, the illustrated stent delivery system 100 includes a handle 106, a rigid support tube 108, outer supports 110, a sheathing grip 112, a proximal trigger 114, a distal trigger 116, a floater 118, an internal connector 120, an inner member 122, a middle sheath 124, an outer sheath 126, a pusher/anchor (or panchor, as defined above) 128, and a tip 132. A pod 134 may be disposed at, or configured to couple to, the distal end of the outer sheath 126 to house a sheathed stent 10. A sheathing tube 202, a sheathing funnel 204, sheathing fingers 206, and a tip insertion funnel 208 facilitate sheathing of the stent 10 into the pod 134 and/or outer sheath 126.

The trigger assembly 102, including the triggers 114, 116, the internal connector 120, and the floater 118, facilitates deployment of the stent 10 from a sheathed state within the pod 134. More specifically, the trigger assembly 102 facilitates moving the outer sheath 126 proximally relative to the inner member 122, thereby retracting the pod 134 from around the stent 10 to expose and deploy the stent 10. Still more specifically, the internal connector 120 may be bonded to the outer sheath 126 and proximal movement of the internal connector 120 relative to the handle 106 (and relative to the inner member 122 and outer supports 110) may cause proximal movement of the outer sheath 126 relative to the inner member 122. Proximal movement of the outer sheath 126 relative to the inner member 122 may result in deployment of the stent 10 sheathed within the pod 134. The triggers 114, 116 allow a practitioner to retract the outer sheath 126 proximally relative to the inner member 122 to deploy the stent, as will be explained in greater detail below with reference to FIGS. 8A1-8A2, 8B1-8B2, 8C1-8C2, and 8D.

The handle 106 is configured to be easily grasped by a practitioner to secure and control the stent delivery device 101 (shown in FIG. 4A). In the illustrated embodiment, the handle 106 is shaped like the handle or butt of a handgun and configured to position the triggers 114, 116 similar to the position of a trigger of a handgun. The handle 106 may be ergonomically configured to be comfortably gripped in a practitioner's hand.

The inner member 122 extends from the handle 106, through the trigger assembly 102, through the tubular member 104, to the panchor 128. A distal inner segment 136 of the inner member 122 may be coupled to the tip 132 and configured for later coupling to the panchor 132 and/or the inner member 122 at the time of a stent implantation procedure. The distal inner segment 136 may be an elongate rigid shaft extending from the tip 132. The inner member 122 may be the inner-most component of the stent delivery device 101. The inner member 122, including the distal inner segment 136, may include a lumen and may be configured to receive a guidewire (not shown) that can guide insertion of the tubular member 104 into a body lumen where the stent 10 is to be deployed. The inner member 122 may be formed of a flexible material, such as polyethylene, which can be easily manipulated over a guidewire into a body lumen. In other embodiments, the inner member 122 may be formed of other flexible materials, including but not limited to nylon, Pebax, polypropylene, and Teflon. The distal segment may be formed of a slightly more rigid material to facilitate insertion through a valve 12 of the stent 10 and/or locking or coupling to the panchor 128 and/or the inner member 122.

An inner assembly 140 (shown in FIG. 4B), which may include the rigid support tube 108, the middle sheath 124, and the panchor 128, may be configured around the inner member 122. The rigid support tube 108 may be securely fixed to the handle 106 and may be configured to secure a proximal end of the inner member 122 relative to the handle 106. In the illustrated embodiment, the rigid support tube 108 may be formed of a metal, such as steel, and may be hollow and configured to receive the inner member 122. The steel rigid support tube 108 may then be crimped at one or more points to secure the inner member 122 inside. In another embodiment the rigid support tube 108 may be formed of a rigid material, such as plastic, and secured to the inner member 122 by bonding, gluing, or other manner of affixing or securing the inner member 122 within or to the rigid support tube 108.

The tip 132 is configured to be positioned at the distal end of the outer sheath 126 and pod 134, when the stent delivery device 101 is in a fully sheathed delivery configuration and the stent 10 is fully sheathed. In the illustrated embodiment, the distal inner segment 136 of the inner member 122 is coupled to the tip 132. The tip 132 may be bonded to or otherwise connected to the distal inner segment 136 of the inner member 122. The tip 132 may be formed of a molded plastic. The distal inner segment 136 may be an elongate shaft configured to extend through the lumen of the stent 10 to engage the panchor 128 and/or couple to the inner member 122.

In the illustrated embodiment, the tip 132 and the distal inner segment 136 are separated from the tubular member 104 of the stent delivery device 101 in the partially sheathed configuration (e.g., prior to use of the delivery system 100 by a practitioner). The distal inner segment 136 is not typically positioned through a lumen of the stent 10 and the valve 12 in the partially sheathed configuration so as to avoid plastic deformation of the valve 12. The distal inner segment 136 may include a connection member 138 configured to couple to the panchor 128. In one embodiment, the connection member 138 may be a barb configured to mate with an opening within the panchor 128. The barb may include a tapered or ramped surface that allows the barb to pass through an opening within the panchor 128 in one direction and may include orthogonal surfaces that inhibit passage of the barb through the opening within the panchor 128 in an opposite direction. The opening within the panchor 128 may include one or more deflectable tabs 129 configured to deflect (e.g., spread apart) in response to contact with the tapered or ramped surface of the barb of the connection member 138. The deflectable tabs 129 may retract to abut the orthogonal surface(s) of the barb and thereby restrict passage of the barb back out of the opening within the panchor 128.

A practitioner can insert the distal inner segment 136 through the lumen of the stent 10, including the valve 12, and engage the connection member 138 into the panchor 128 just prior to sheathing. The connection member 138 may be configured such that once the connection member 138 of the distal inner segment 136 is inserted into the panchor 128 the distal inner segment 136 cannot be removed. In this manner, the tip 132 is secured into position for sheathing and for the fully sheathed delivery configuration.

The tip 132 may include a narrow lumen 133 that connects to a lumen through the distal inner segment 136 and the lumen of the inner member 122 to allow a guidewire to be inserted into and through the inner member 122. The tip 132 may be formed in a conical shape, tapering toward the distal end, to lead and guide the tubular member 104 during insertion into a lumen of the patient's body, for example, the esophagus. The connection member 138 of the distal inner segment 136 may couple the distal segment to the panchor 128 in such a way that the lumen through the distal inner segment 136 and the tip 132 aligns with the lumen of the inner member 122.

In some embodiments, one or more spacers 121a, 121b, 121c (collectively 121) may be positioned around the distal inner segment 136 of the inner member 122 and may extend proximally from the tip 132 to the panchor 128. The spacers 121 may be free floating around (e.g., coaxially with) the distal inner segment 136. The spacers 121 may provide a surface or other support structure against which the panchor 128 (or segments of the panchor 128) may abut to restrict proximal and/or distal movement of the panchor 128 and panchor segment relative to, for example, the tip 132. During sheathing of a stent, for example, forces may be exerted on the stent in a distal direction, which in turn creates forces in a distal direction on the panchor 128 and the individual segments of the panchor 128. The distal forces on the panchor 128 may cause the panchor segments to tend to separate. The one or more spacers 121 may restrict and/or prevent separation of panchor segments due to distal forces on the panchor 128 created during sheathing.

In one embodiment, a first spacer 121a may abut with and/or engage the panchor 128. The first spacer 121a may have an outer diameter sized to allow the first spacer 121a to abut and/or engage an inner surface of the panchor 128. The second spacer 121b may abut a distal end of the first spacer 121a and have an outer diameter that is larger than the outer diameter of the first spacer 121a. The larger diameter of the second spacer 121b may enable the second spacer to engage the panchor 128 and restrict distal movement of the panchor 128. More specifically, the second spacer 121b may have an outer diameter large enough to engage an inner surface of a socket portion of the panchor 128 and thereby prevent a corresponding segment of the panchor 128 from moving distally, for example relative to the tip 132. The third spacer 121c may abut a distal end of the second spacer 121b and extend distally to abut the tip 132 and/or an outer tube portion of the distal inner segment 136. The third spacer 121c may have an outer diameter similar to the diameter of the first spacer 121a. The spacers 121 may be formed of a rigid material, such as a high yield strength polypropylene, to provide a desired longitudinal rigidity to counteract the forces in the distal direction exerted on the panchor 128 and/or panchor segments.

The pod 134 may house the stent 10 in a crimped configuration or otherwise compressed configuration. In other words, the stent 10 in a crimped configuration can be sheathed within the pod 134. The pod 134 may be formed of a plurality of sheath layers (collectively 131) that may be reflowed to form a solid wall of material. Forming the pod 134 from a plurality of sheath layers that are reflowed allows a way to bond the pod 134 to a transition 135 and maintain constant an outside diameter at a junction between the pod 134 and the transition 135. FIG. 4D1 provides a side cross-sectional view of a portion of the pod 134, the transition 135, and the outer sheath 126. FIG. 4D2 provides an enlarged cross-sectional view of the same. In the embodiment shown in FIGS. 4D1 and 4D2, the pod 134 may comprise three sheath layers 131a, 131b, 131c, an outer sheath layer 131a, a mid jacket sheath layer 131b, and a liner sheath layer 131c. These sheath layers 131 may form a wall of the pod 134. The liner sheath layer 131c may be a 0.005" polytetrafluoroethylene (PTFE) liner, configured to limit frictional forces between a sheathed stent and an inner surface of the pod 134. The mid jacket sheath layer 131b may be 0.005" 55D Pebax and may provide structural reinforcement to the wall of the pod 134. The outer sheath layer may be 0.010" 55D Pebax. The three layers can be reflowed with heat to fuse or meld them together and make them one solid wall of material.

The transition 135 may be molded, for example of Pebax, to taper from an outer diameter approximately equal to the outer diameter of the pod 134 to an outer diameter approximately equal to the outer diameter of the outer sheath 126. The outer sheath layer 131a may slide over a larger, distal end of the transition 135 while the mid jacket layer 131b may abut against the distal end of the transition 135. When reflowed, the outer sheath layer 131a, a mid jacket sheath layer 131b, and a liner sheath layer 131c may fuse or meld together and also fuse or meld to the transition 135 and may form a single integral wall of the pod 134.

The panchor 128 is configured to secure the stent 10 within the pod 134. The panchor 128 may function as both a pusher and an anchor to restrict movement of the stent both proximally and distally relative to the panchor 128. More specifically, the panchor is configured to push against the stent 10 as a force in a proximal direction is exerted on the stent and configured to anchor the stent 10 as a force in a distal direction is exerted on the stent 10. The panchor 128 may include one or more annular flanges about an outer circumference of the panchor 128. The one or more annular flanges may engage the inner surface of the stent at one or more positions longitudinally along the stent 10. In one embodiment, the one or more annular flanges may have five sides, such that an apex between each of the sides is configured to engage an inner surface of the stent 10 between connectors of the scaffolding structure of the stent 10. The panchor 128 is shown in FIGS. 14A-14H, and will be described in greater detail below with reference to the same.

The middle sheath 124 is positioned around the inner member 122 in abutment with the rigid support tube 108 and the panchor 128. The middle sheath 124 may function as a space-filler between the inner member 122 and the outer sheath 126. By filling the space between the inner member 122 and the outer sheath 126, the middle sheath 124 can provide additional structural support for the inner member 122 against buckling, crimping, and other undesired bending and/or collapse of the inner member 122 and/or the outer sheath 126. In particular, pressure on the inner member 122 created by forces in the longitudinal direction of the inner member 122 during deployment of a stent can cause the inner member 122 to buckle, crimp, or otherwise bend in an undesirable fashion. The middle sheath 124 and the outer sheath 126 (in abutment with the middle sheath 124) provide additional structural support against buckling, crimping or other undesired bending of the inner member 122.

The inner assembly 140 (shown in FIG. 4B) may remain substantially fixed (in the proximal and distal directions) relative to the handle 106. The outer sheath 126 is retracted proximally over the inner assembly 140 to expose the distal region of the inner assembly 140. The trigger assembly 102 may facilitate proximal retraction of the outer sheath 126.

The outer sheath 126 may substantially encase the inner assembly 140, or at least a distal region of the inner assembly 140. In the illustrated embodiment, when the stent delivery device 101 is in the fully sheathed delivery configuration, the outer sheath 126 may abut a distal portion of the tip 132 and extend proximally toward a proximal end of the middle sheath 124, where the outer sheath 126 may couple to the internal connector 120. As can be appreciated, in other embodiments the outer sheath 126 may extend proximally to a greater or lesser degree as a function of the positioning of, and/or coupling to, the internal connector 120 and/or the distal trigger 116. The outer sheath 126 may be formed of a flexible material, such as nylon, which can be manipulated into a body lumen of a patient. In other embodiments, the outer sheath 126 may be formed of other flexible materials, including but not limited to polyethylene, Pebax, polypropylene, and Teflon.

The outer sheath 126 may couple to the smaller, proximal end of the transition 135, as shown in FIGS. 4D1 and 4D2. The outer sheath 126 may be formed of, for example, two layers 127a, 127b of Pebax and may be configured to couple to the proximal end of the transition 135 similar to the coupling of the pod 134 to the distal end of the transition 135. An outer layer 127a may fit over the outer diameter of the proximal end of the transition 135 while an inner layer 127b may abut against the proximal end of the transition 135. The two layers may be reflowed and fused or melded together and to the transition 135.

The outer supports 110 may support and/or provide a housing for the trigger assembly 102. The outer supports 110 may include a plurality of elongate shafts secured to and/or extending from the handle 106. The outer supports 110 may be configured to provide a guide for a plurality of triggers 114, 116, a housing for the trigger assembly 102, and a structure against which the trigger safety 142 can secure the triggers 114, 116. In the illustrated embodiment, the outer supports 110 include an upper outer support 110a and a lower outer support 110b (collectively 110), each configured in a half cylindrical shape. The outer supports 110 may mate together to form a housing around a portion of the proximal end of the outer sheath 126, the internal connector 120, the floater 118, and a proximal portion of the inner assembly 140.

The outer supports 110 also provide a support structure for the triggers 114, 116. The triggers 114, 116 may be mounted on and/or positioned around the outside of the outer supports 110 and are slidably movable, proximally and/or distally relative to the outer supports 110. The outer supports 110 also may be configured to form or otherwise provide one or more trigger guide slots 150 (shown in FIG. 4A) to restrict rotational movement of the triggers about a longitudinal axis of the outer supports 110. The trigger guide slots 150 also provide a track or guide for the triggers 114, 116 as they move proximally and/or distally relative to the outer supports 110. A proximal end of the outer supports 110 may couple to the handle 106 and a distal end of the outer supports may couple to the sheathing grip 112. The outer supports 110 may also provide one or more trigger safety notches 144 configured to be engaged by the trigger safety 142 to limit proximal movement of the distal trigger 116. In the illustrated embodiment, the trigger safety notches 144 are adjacent to the trigger guide slots 150. In another embodiment, one or more trigger safety notches may be positioned separate from the trigger guide slots 150.

The sheathing grip 112 may couple to the outer supports 110 and may slidably abut against the outer sheath 126. The sheathing grip 112 may be molded of soft Pebax to provide flexibility. The sheathing grip 112 may be configured to relieve strain on the outer sheath 126 as the tubular member 104 is manipulated during insertion into a patient's body. Specifically, the sheathing grip 112 may be configured to allow the outer sheath 126 to be displaced at an angle to the outer supports 110 without kinking the outer sheath 126. This translates to allowing the user to position, for example, a distal portion of the outer sheath 126 at an angle to a main axis of the handle 106 and triggers 114, 116 without kinking the outer sheath 126. If the outer sheath 126 is kinked, then the stent may not deploy. The strain relief component guards against kinking of the outer sheath. The sheathing grip 112 may also allow the outer sheath 126 to slidably move longitudinally for sheathing and deployment of the stent.

The internal connector 120 may couple the outer sheath 126 and the distal trigger 116. The internal connector 120 may be a rigid elongate tubular structure. In the illustrated embodiment, one or more protrusions 152 on the internal connector 120 near the proximal end extend radially outward to engage the distal trigger 116. The internal connector 120 may be positioned within the housing formed by the outer supports 110. A distal portion of the internal connector 120 may be bonded to or otherwise coupled to the outer sheath 126. Accordingly, proximal movement of the internal connector 120 causes proximal movement of the outer sheath 126 relative to the inner member 122. Proximal movement of the outer sheath 126 relative to the inner member 122 results in deployment of a stent 10 sheathed within the pod 134. Similarly, distal movement of the outer sheath 126 relative to the inner member 122 causes distal movement of the internal connector 120. In one embodiment the internal connector 120 may be partially inserted into a lumen of the outer sheath 126, such that an outer surface of the internal connector 120 is bonded to an interior surface of the outer sheath 126. In another embodiment, the outer sheath 126 may be received into the lumen of the internal connector 120, such that an interior surface of the internal connector 120 is bonded to an outer surface of the outer sheath 126. In still another embodiment, a distal edge of the internal connector 120 may be bonded to a proximal edge of the outer sheath 126. In still other embodiments, a coupling mechanism, such as barbs, a pin, or the like may couple the internal connector 120 to the outer sheath 126.

The internal connector 120 may further include a floater engagement surface 153 configured to be engaged by the floater 118 as it moves proximally relative to the internal connector 120. In the illustrated embodiment, the floater engagement surface may be at a proximal end of a floater engagement channel 160 in the internal connector 120. The internal connector 120 may include a pair of floater engagement channels 160 configured to receive and guide a pair of barbed prongs 176 of the floater 118. As the barbed prongs 176 move proximally within the floater engagement channels 160, the barbs 178 may engage the floater engagement surface 153. Accordingly, proximal movement of the floater 118 past a given distance may result in proximal movement of the internal connector 120. The given distance past which proximal movement of the floater 118 results in proximal movement of the internal connector 120 may be the length of the floater engagement channel 160. As can be appreciated, in another embodiment the floater engagement surface 153 may also be positioned on the distal trigger 116.

Figure 10B:
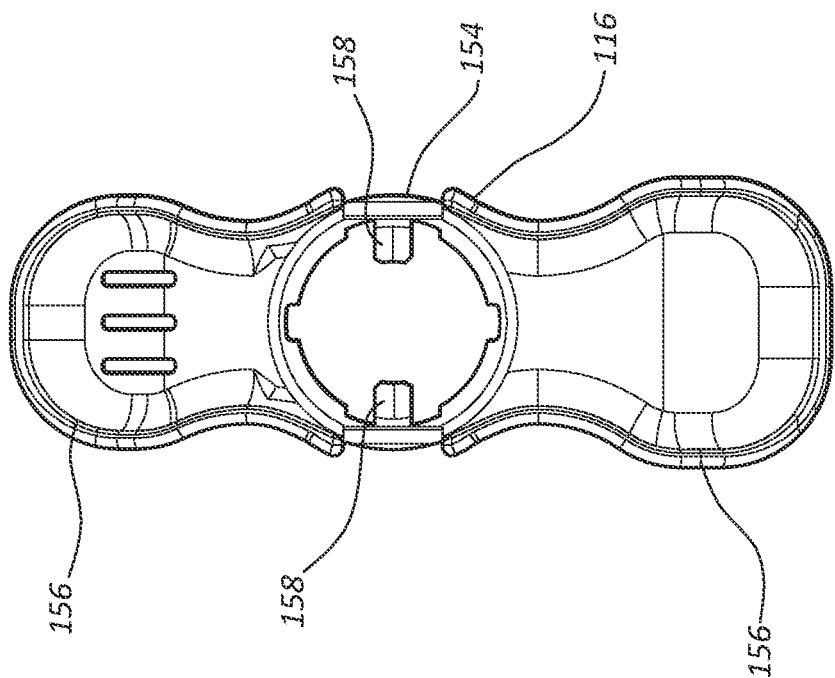
FIG. 10B is an end view of a distal trigger of the stent delivery system of FIG. 1.
Figure 10A:
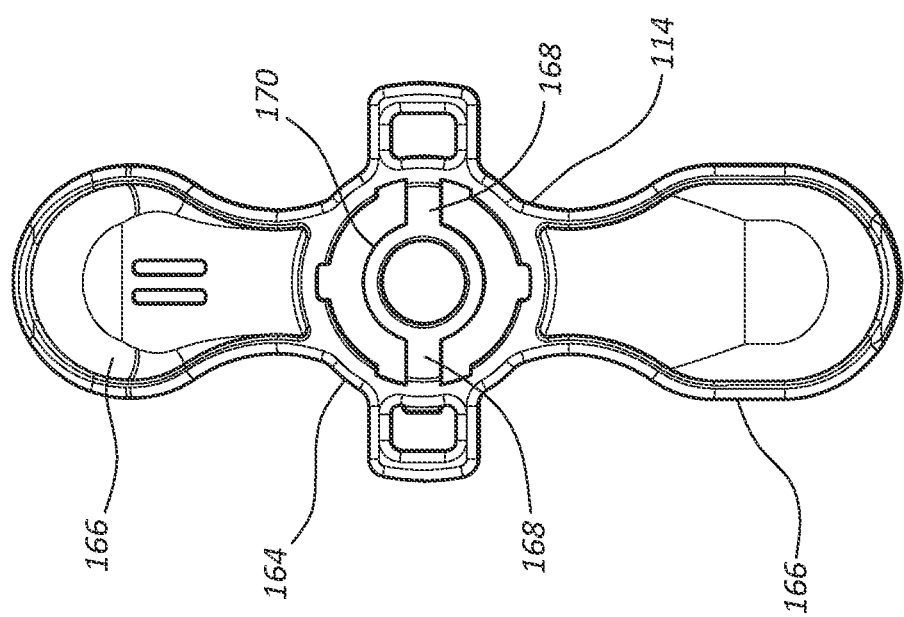
FIG. 10A is end view of a proximal trigger of the stent delivery system of FIG. 1.

The distal trigger 116 may include a ring-shaped base with a pair of finger holds extending radially outward from the outer surface of the base directly opposite one another. The distal trigger 116 is configured to engage or otherwise couple to the internal connector 120. The proximal trigger 114 may be configured similar to the distal trigger 116, having a ring-shaped base and a pair of finger holds extending radially outward from the outer surface of the base directly opposite one another. The proximal trigger 114 is configured to engage or otherwise couple to the floater 118. The proximal trigger 114 and distal trigger 116 are shown in FIGS. 10A and 10B, respectively, and described in greater detail below with reference to the same.

The floater 118 may comprise a tubular shaft having a distal engagement mechanism 172 and a proximal engagement mechanism 174. In the illustrated embodiment, the distal engagement mechanism 172 may be one or more barbed prongs 176 at the distal end of the floater 118. The barbed prongs 176 may include outwardly protruding barbs 178. The barbs 178 may be configured to engage the distal trigger 116 and/or the proximal end of the internal connector 120 as the floater 118 is retracted proximally. For example, proximal movement of the floater 118 past a given distance may result in the barbs 178 engaging the floater engagement surface 153 of the internal connector 120 and in turn may result in proximal movement of the internal connector 120. The given distance may be approximately the length of the floater engagement channel 160 of the internal connector 120.

The barbs 178 may also be configured to allow the floater 118 to move distally and to telescope into the internal connector 120. For example, the barbs 178 may be configured to slide distally for the length of the floater engagement channel 160. The given distance may also be approximately equivalent to the length of the floater 118, such that the distal trigger 116 and internal connector 120 can be moved proximally relative to the floater 118 and proximal trigger 114 a length of the floater 118 until the distal trigger 116 is drawn into abutment with the proximal trigger 114. This enables serial retraction of the distal trigger 116 following retraction of the proximal trigger 114.

Stated differently, the distal engagement mechanism 172 may allow the floater to move distally relative to the distal trigger 116 and the internal connector 120 (and telescope into the internal connector 120). The distal engagement mechanism 172 may also limit proximal movement of the floater relative to the distal trigger 116 and the internal connector 120 because the barbs 178 of the distal engagement mechanism 172 engage the internal connector 120 (at the proximal end) and/or engage the distal trigger 116. Described still another way, the distal engagement mechanism 172 may allow the distal trigger 116 and the internal connector 120 to move proximally relative to the floater 118 (and proximal trigger), such that the distal trigger 116 can be retracted proximally toward the proximal trigger 114 to enable serial retraction of the proximal trigger 114 and distal trigger 116. Serial retraction of the triggers 114, 116 will be described in greater detail below with reference to FIGS. 8A1-8A2, 8B1-8B2, and 8C1-8C2.

In the illustrated embodiment, the proximal engagement mechanism 174 may include a flange or lip around the circumference of the floater 118 at the proximal end. The proximal engagement mechanism 174 may be configured to engage a floater engagement ring 170 (shown in FIG. 10A) of the proximal trigger 114, such that proximal movement of the proximal trigger 114 results in proximal movement of the floater 118. Accordingly, proximal movement of the proximal trigger 114 relative to the handle 106 and inner member 122 may result in proximal movement of the floater 118, the distal trigger 116, the internal connector 120, and the outer sheath 126, thereby at least partially deploying the stent 10. Deployment of the stent 10 is described in greater detail below with reference to FIGS. 8A1-8A2, 8B1-8B2, 8C1-8C2, and 8D.

FIGS. 5A-5I are perspective views illustrating assembly of a sheathing mechanism 201 at a distal region of the stent delivery system 100 of FIG. 1, sheathing of a stent 10, and disassembly of the sheathing mechanism 201, preparatory to performing a stent implantation procedure. The delivery device 100 begins in a partially sheathed configuration in FIG. 5A and ends in a fully sheathed delivery configuration in FIG. 5I. The components of the sheathing mechanism 201 are described referring collectively to FIGS. 3 and 5A-5D.

FIG. 5A is a perspective view of the stent delivery system 100 illustrating the sheathing tube 202 and sheathing funnel 204 disposed over the outer sheath 126 of the tubular member 104. The sheathing tube 202 may have a tube-like cylindrical shape. The inner diameter of a lumen of the sheathing tube 202 may be sized and shaped to be positioned over an outer diameter of a distal region of the outer sheath 126 and/or the pod 134 of the delivery device 101. Furthermore, the sheathing tube 202 lumen may have an inner diameter configured to allow the sheathing tube 202 to be slidably moveable relative to the outer sheath 126 and/or the pod 134. In the illustrated embodiment, the sheathing tube 202 may slide relative to the outer sheath 126 and relative to the pod 134 without interference.

The sheathing funnel 204 may be disposed at a distal end of the sheathing tube 202. A proximal end of the sheathing funnel 204 may be coupled to the sheathing tube 202 in a manner that the inner diameter of the sheathing funnel 204 at the proximal end is approximately equivalent to the inner diameter of the sheathing tube 202 at the distal end. The sheathing funnel 204 may have an internal taper configured to guide an expanded portion of a stent 10 and the sheathing fingers 206 into the sheathing tube 202. Accordingly, the distal end of the sheathing funnel 204 may have an inner diameter that is larger than the inner diameter of the proximal end of the sheathing funnel 204 and the inner diameter tapers from the distal end to the proximal end.

The sheathing funnel 204 may include ribs 222 disposed on an internal surface of the sheathing funnel 204 and extending in a direction generally from the distal end to the proximal end of the sheathing funnel 204. The ribs of the sheathing funnel 204 are shown in greater detail in FIGS. 12A-12C and described in greater detail below with reference to the same. The ribs 222 may interact with the sheathing fingers 206 to cause the sheathing fingers 206 to align with the ribs 222, such that a flared region 212 of the sheathing fingers is positioned on either side of each rib 222 and the ribs are positioned in the gaps between the flared regions 212. The ribs also interact with the stent 10 during sheathing. The sheathing funnel 204, and particularly the ribs 222, guides the stent 10 and the sheathing fingers 206 into the sheathing tube 202 to crimp the stent 10 during (or substantially contemporaneous with) sheathing. The crimped stent 10 can then be drawn into and sheathed within the pod 134.

Figure 5B:
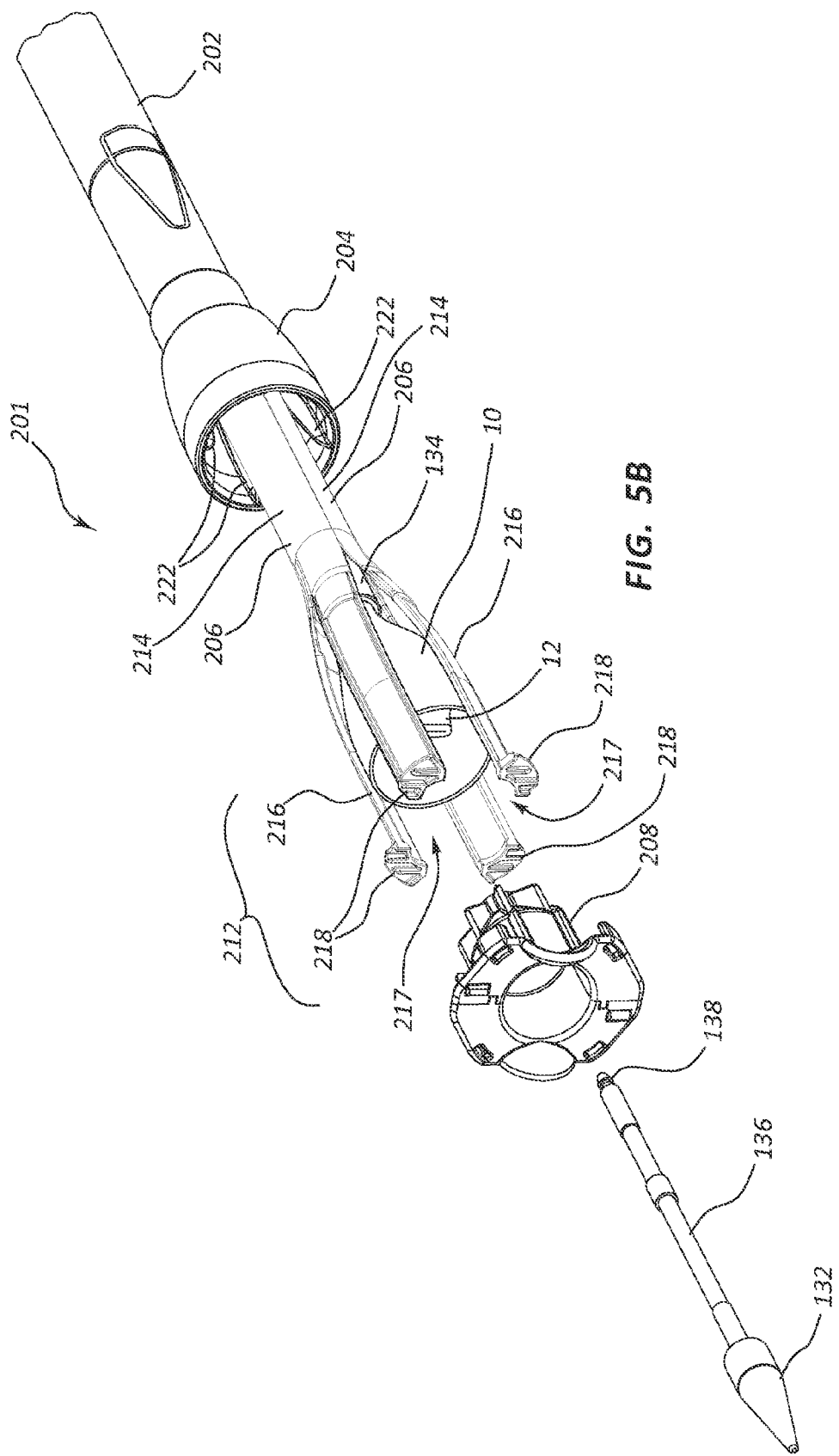
FIG. 5B is a perspective view illustrating assembly of a sheathing mechanism at a distal region of the stent delivery system of FIG. 1.

FIG. 5B illustrates the sheathing fingers 206 assembled and arranged around and/or in engagement with a distal region of the outer sheath 126 (see e.g., FIG. 5A) and/or the pod 134. The flared portions 212 of the sheathing fingers 206 are disposed around the outer diameter of an unsheathed portion of the stent 10. The sheathing fingers 206, as mentioned, interact with the sheathing funnel 204 to aid in drawing the stent 10 into the sheathing tube 202 to crimp and sheath the stent in the pod 134. In the illustrated embodiment, the sheathing mechanism 201 includes a plurality of sheathing fingers 206 (e.g., two halves). The sheathing fingers 206 may each include a base portion 214 and a flared portion 212. The base portions 214 of the plurality of sheathing fingers 206 may be configured to couple together to at least partially surround a distal region of the outer sheath 126 and/or the pod 134. The base portions 214, when coupled together around the outer sheath 126 may also be configured to be received into the sheathing tube 202, such that the base portions 214 can be disposed between the outer sheath 126 (and/or the pod 134) and the sheathing tube 202. FIG. 5B illustrates the sheathing tube 202 drawn up around a portion of the base portions 214 of the sheathing fingers 206.

In the illustrated embodiment, a proximal end of the base portions 214 forms an inner taper configured to abut against a corresponding tapered region at the transition between the outer sheath 126 and the pod 134. The inner taper of the base portions 214 may limit distal movement of the sheathing fingers 206 relative to the tubular member 104 of the stent delivery device 101, particularly during sheathing, which may result in pulling the pod 134 over the compressed stent 10.

The flared portions 212 (FIGS. 3 and 5A) may be configured to extend distally beyond the distal end of the outer sheath 126 and extend along a length of an unsheathed portion of the stent 10 beyond a distal end of the stent 10. The flared portions 214 may be arranged circumferentially about an outer diameter of the unsheathed portion of the stent 10. The flared portions 212 may be configured to collapse axially inward, toward a longitudinal axis of the stent 10 extending through the center of the lumen of the stent 10, as the flared portions 212 of the sheathing fingers 206 are drawn into the sheathing funnel 204 and/or sheathing tube 202 during a sheathing action. As the flared portions 212 collapse inwardly, they compress the stent 10 to an outer diameter less than the inner diameter of the pod 134. The pod 134 can then be drawn over the compressed stent 10 to a fully sheathed delivery configuration.

In the illustrated embodiment, the flared portions 212 are divided into two elongate projections 216 forming a gap 217 in between the projections 216. As described, ribs 222 on an inner surface of the sheathing funnel 204 may align with the gaps 217 between the projections 216 to guide the flared portions 212 as they are drawn into the sheathing funnel 204. The gaps 217 may allow the flared portions 212 to collapse and narrow (e.g., reduce the outer diameter) as the projections 216 are drawn into and received into the sheathing funnel 204 and sheathing tube 202. The distal end of each projection 216 may include a flange 218 configured to couple to or otherwise receive the tip insertion funnel 208.

FIG. 5C illustrates the tip insertion funnel 208 coupled to the distal ends of the sheathing fingers 206. In particular, the tip insertion funnel 208 may be configured to couple to the flanges 218 (see e.g., FIG. 5B) at the distal ends of the elongate projections 216 of the flared portions 212 of the sheathing fingers 206. The tip insertion funnel 208 tapers from a large distal opening 260 to a relatively small proximal opening. The tapered shape of the tip insertion funnel 208 aids to guide insertion of the distal inner segment 136 of the inner member 122 as the distal inner segment 136 is inserted through the valve 12 of the stent 10 and into the panchor 128. As described above, the valve 12 may be formed of an easily deformed polymer. The tip insertion funnel 208 precisely guides the proximal end of the distal inner segment 136 retrograde through the valve 12 to avert undesired contact and/or damage, for example, to leaflets of the valve 12 or other portion of the valve 12, as a result of imprecise insertion of the distal inner segment 136. The connection member 138 at the proximal end of the distal inner segment 136 may be relatively sharp and/or pointed. As can be appreciated, even a relatively small force focused on the relatively narrow point of the connection member 138 can multiply the force and cause damage to the valve 12 and/or plastically deform the valve 12. The tip insertion funnel 208 provides a precise guide to properly insert the distal inner segment 136 through the valve 12 without causing damage or deformation. The stent delivery system 100 is in a partially sheathed configuration for storage and/or transport. With the aid of the tip insertion funnel 208, the tip 132 and distal inner segment 136 can readily be inserted by a practitioner. The tip insertion funnel 208 is shown in greater detail in FIGS. 15A-15C and is described below with reference to the same.

Figure 5D:
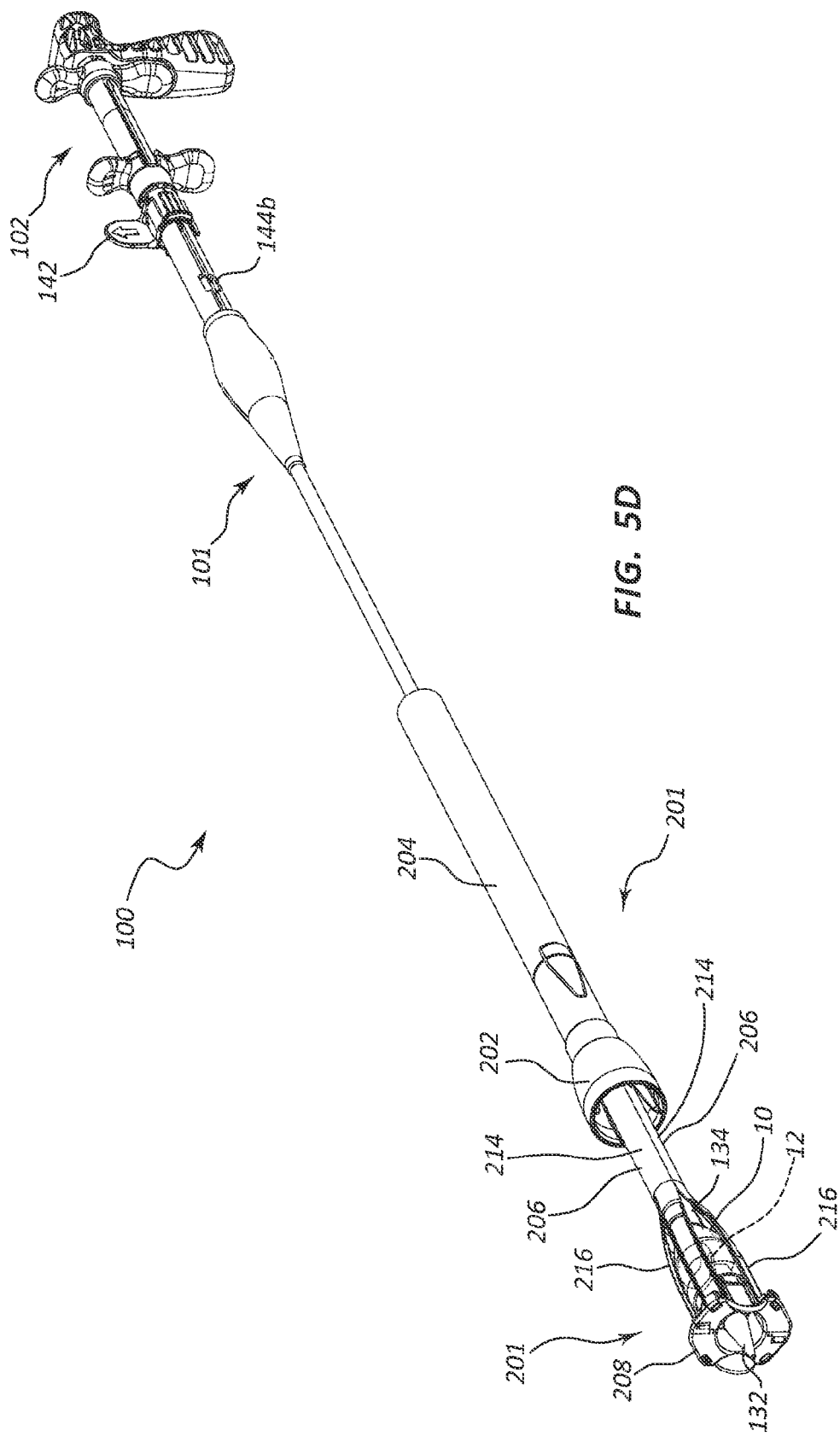
FIG. 5D is a perspective view illustrating the stent delivery system of FIG. 1 in a partially sheathed configuration with a fully assembled sheathing mechanism.

FIG. 5D illustrates the stent delivery system 100 in a partially sheathed configuration with the tip 132 and distal inner segment 136 inserted. The connection member 138 at the proximal end of the distal inner segment 136 is inserted through the tip insertion funnel 208, through the stent 10, including the valve 12, and into the panchor 128 (not visible in FIG. 5D, but see FIG. 3). The sheathing mechanism 201 of the stent delivery system 100 is fully assembled at a distal region of the stent delivery device 101. The trigger safety 142 is positioned to prevent premature full deployment of the partially sheathed stent 10 before the sheathing process that will fully sheathe the stent. The trigger safety 142 is positioned in engagement with the first trigger safety notch 144a (hidden from view in FIG. 5D, but viewable in FIG. 3 and FIG. 4A). During sheathing of the stent, the trigger safety 142 will transition to the second trigger safety notch 144b. The tip insertion funnel 208 can be detached from the sheathing fingers 206 prior to sheathing.

FIG. 5E1 illustrates the tip insertion funnel 208 removed from the distal ends of the sheathing fingers 206, preparatory to sheathing. The tip insertion funnel 208 may be detached from the flanges 218 and/or the sheathing fingers 206 and opened to slide over the inserted tip 132.

FIG. 5E2 illustrates an end view of the distal end of the stent delivery system 100 with the sheathing mechanism 201 positioned as in FIG. 5E1. The flared portions 212 of the sheathing fingers 206 are in a flared state and the flanges 218 at a distal end of the elongate projections 216 are extended outward beyond an outer perimeter of the sheathing funnel 204. Other components are shown on the drawing for reference.

FIG. 5F1 illustrates the beginning of a sheathing action. A user, such as a medical practitioner, may grasp in one hand the sheathing tube 202 and/or sheathing funnel 204 of the assembled sheathing mechanism 201 and grasp in the other hand the sheathing grip 112 of the stent delivery device 101. The user may push the sheathing tube 202 of the sheathing mechanism 201 forward toward the distal end of the stent delivery system 100. In other words, the user may push or otherwise move (displace) the sheathing tube 202 and sheathing funnel 204 in a distal direction with the first hand and away from the second hand and the sheathing grip 112, while restraining distal movement of the sheathing grip 112.

Alternatively and/or in addition, the practitioner can pull the sheathing grip 112 back in a proximal direction toward the handle 106 at the proximal end of the stent delivery system 100. The sheathing funnel 204 and/or the sheathing tube 202 and/or the sheathing fingers 206 pull the pod 134 over the crimped stent 10. The pod 134 in turn pulls and moves the outer sheath 126, the internal connector 120 (not visible in FIG. 5F1), the trigger safety 142, the distal trigger 116, the floater 118 (not visible in FIG. 5F1), and the proximal trigger 114, all in a distal direction relative to the handle 106 and the tip 132. The displacement also occurs relative to the components of the internal assembly, although the components of the internal assembly are not viewable, including the middle sheath 124, the panchor 128, the inner member 122, and the distal inner segment 136. Arrows indicate the direction of the resulting movement relative to the handle 106. FIG. 5F1 illustrates the sheathing tube 202 and sheathing funnel 204 moved slightly relative to FIG. 5E1. The sheathing funnel 204 is drawn over the flared portions of the sheathing fingers, including the flanges 218.

FIG. 5F1 also illustrates a displacement of the trigger safety 142, the distal trigger 116 and the proximal trigger 114.

FIG. 5F2 illustrates an end view of the distal end of the stent delivery system 100 with the sheathing mechanism 201 positioned as in FIG. 5F1. The flanges 218 at a distal end of the elongate projections of the flared portions of the sheathing finger are drawn into and within an outer perimeter of the sheathing funnel 204. Other components are shown on the drawing of FIG. 5F2 for reference.

FIG. 5F3 is an enlarged sectional view of the sheathing funnel 204 and/or the sheathing tube 202 with the flanges 218 disposed within the sheathing funnel 204. Further distal movement of the sheathing tube 202 and/or sheathing funnel 204 cause the flanges 218 to engage against the collar 205 disposed within the sheathing funnel 204 and/or the sheathing tube 202.

FIG. 5G1 illustrates another phase of the sheathing action. The sheathing tube 202 and/or sheathing funnel 204 are moved distally over the pod 134, the stent 10, the tip 132, and the flared portions 216 of the sheathing fingers 206 (not shown in FIG. 5G1 for clarity). Relative displacement of the sheathing tube 202 and/or sheathing funnel 204 can be seen in comparison to FIG. 5F1. Pushing the sheathing tube 202 and/or sheathing funnel 204 may cause movement of the sheathing tube 202 and/or sheathing funnel 204 over the stent 10 and sheathing fingers 206 to crimp the stent 10 and/or collapse the sheathing fingers 206 inwardly. In addition, movement of the sheathing tube 202 and/or sheathing funnel 204 over the stent 10 and sheathing fingers 206 may pull the outer sheath 126 over the crimped stent 10. The flanges 218 of the sheathing fingers 206 may engage the collar 205 within the inner surface of the tapered sheathing funnel 204 and/or the sheathing tube 202. The engagement of the flanges 218 with the collar 205 may cause the distal movement of the sheathing funnel 204 and/or the sheathing tube 202 to move the sheathing fingers 206, which in turn move the outer sheath 126 distally to sheath the crimped stent 10.

Again, movement of the outer sheath 126 relative to the handle may in turn result in displacement of the internal connector 120 (not visible in FIG. 5G1), the trigger safety 142, the distal trigger 116, the floater 118 (not visible in FIG. 5G1), and the proximal trigger 114, all in a distal direction relative to the handle 106 and the tip 132. Arrows indicate the direction of the resulting movement relative to the handle 106.

The distal movement of the sheathing tube 202 and sheathing funnel 204 collapses the sheathing fingers 206, which crimps or compresses the stent 10 to a diameter smaller than the inner diameter of the pod 134. The distal movement of the sheathing tube 202 and sheathing funnel 204 also pulls the pod 134 over the compressed stent 10 to fully sheathe the stent 10. When the trigger safety 142 reaches a second trigger safety notch 144b (FIGS. 5E1 and 5F1), it may make an audible click to indicate that the stent 10 is fully sheathed and the stent delivery system 100 is in the fully sheathed delivery configuration. In FIG. 5G1, the outer sheath 126, the trigger safety 142, the distal trigger 116, and the proximal trigger 114 are all shifted distally relative to the handle 106. The trigger safety 142 is positioned to engage the second trigger safety notch 144b. Although not visible in the view of FIG. 5G1, the internal connector 120 and the floater 118 are also shifted distally.

FIG. 5G2 illustrates an end view of the distal end of the stent delivery system 100 with the sheathing mechanism 201 positioned as in FIG. 5G1. The flanges 218 at a distal end of the elongate projections of the flared portions of the sheathing finger are more fully drawn into the sheathing funnel 204 and are entirely collapsed inward and abutting each other. The flanges 218 may be engaging the collar 205 disposed within the sheathing funnel 204 and/or the sheathing tube 202.

FIG. 5G3 is an enlarged sectional view of the sheathing funnel 204 and/or the sheathing tube 202 with the flanges 218 engaged against the collar 205 disposed within the sheathing funnel 204 and/or the sheathing tube 202. The collar 205 causes distal movement of the sheathing funnel 204 and/or the sheathing tube 202 to distally displace the sheathing fingers 206, thereby distally moving the outer sheath 126 to sheathe the crimped stent 10.

Figure 5H:
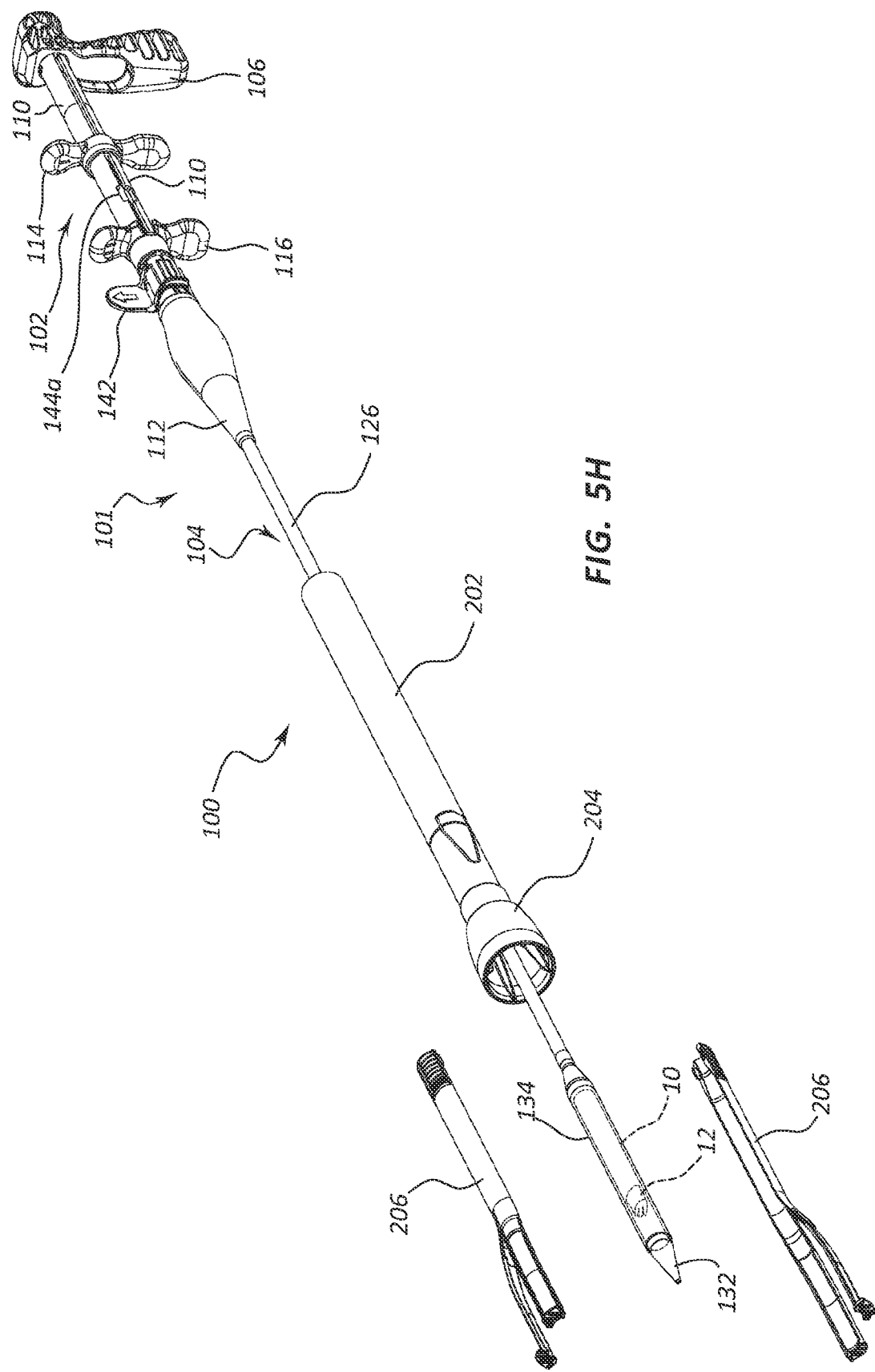
FIG. 5H is a perspective view illustrating disassembly of the sheathing mechanism of the stent delivery system of FIG. 1, preparatory to performing a stent implantation procedure.
Figure 5I:
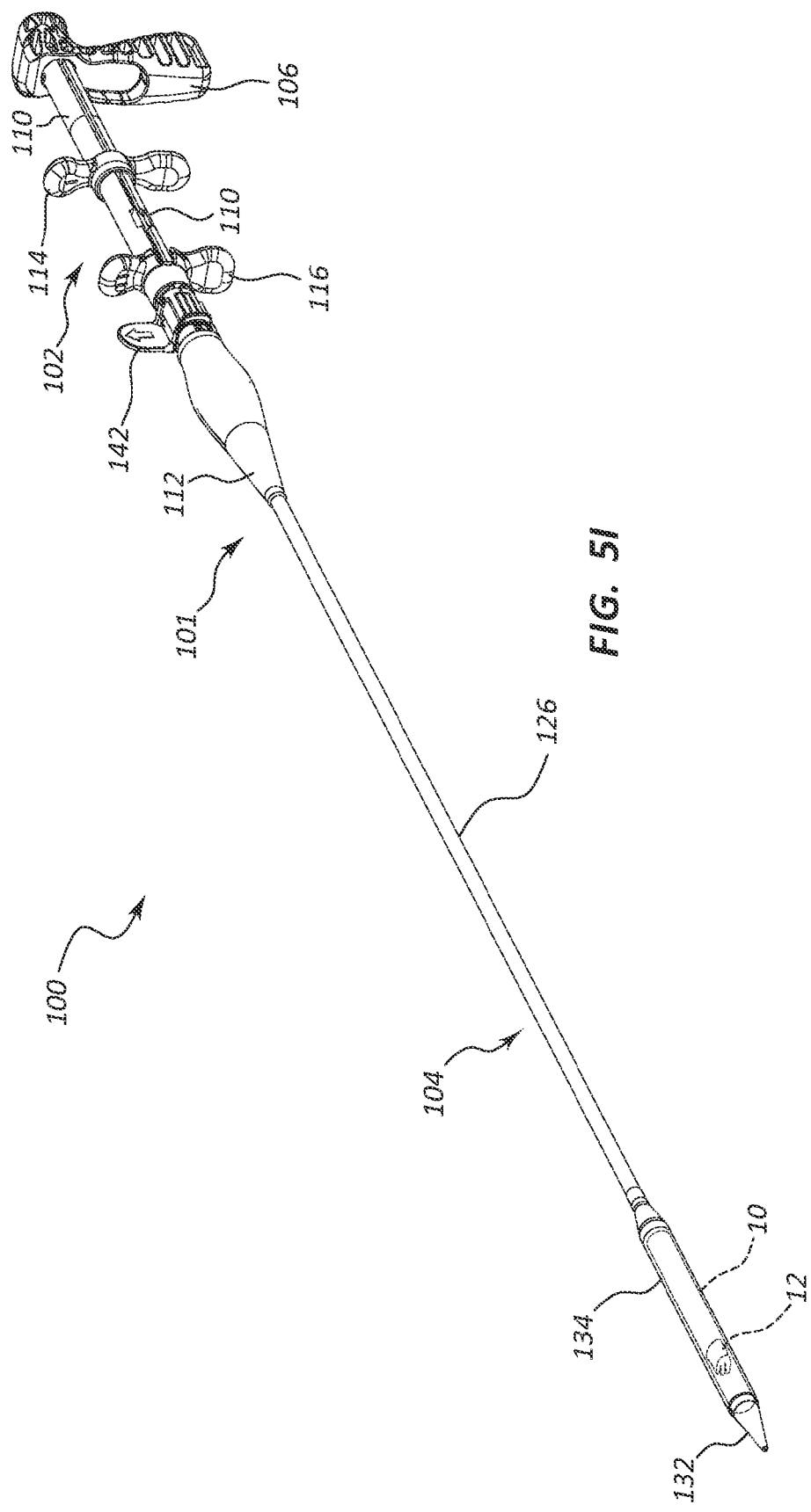
FIG. 5I is another perspective view of the sheathing mechanism of the stent delivery system of FIG. 1 in a fully sheathed delivery configuration, preparatory to performing a stent implantation procedure.

FIGS. 5H and 5I illustrate disassembly of the components of the sheathing mechanism 201 (see FIG. 2), preparatory to an implantation procedure to implant the stent 10. In FIG. 5H, the sheathing tube 202 and/or sheathing funnel 204 are shown retracted proximally to expose the sheathing fingers 206 and/or the pod 134, such that the sheathing fingers 206 can be removed. The sheathing fingers 206 are shown separated and detached from around the pod 134. The pod 134 is slid over an entire length of the stent 10, thereby sheathing the stent.

FIG. 5I illustrates the sheathing tube 202 and sheathing funnel 204 pulled over the pod 134 and tip 132 and removed from the tubular member 104 of the stent delivery device 101. The stent delivery device 101 is now in a fully sheathed delivery configuration and ready for use in a procedure to deploy the stent 10 in a target lumen of a patient needing treatment.

FIGS. 6A1-6A2, 6B1-6B2, 6C1-6C2, and 6D1-6D2 are cross-sectional views of the stent delivery system of FIG. 1, at various positions during sheathing of a partially sheathed stent 10 to transition the stent delivery system 100 from a partially sheathed configuration to a fully sheathed delivery configuration.

FIG. 6A1 is a side view of the stent delivery system 100 in a partially sheathed configuration and a similar configuration as in FIG. 5E1. FIG. 6A2 is an enlarged cross-sectional side view of a distal region of the stent delivery system 100. Referring generally and collectively to FIGS. 6A1 and 6A2, the stent delivery system 100 is prepared for the sheathing process. The tip 132 and distal inner segment 136 are inserted into the panchor 128 and the stent 10 is partially sheathed within the pod 134. The pod 134 is at position $P_s pod_1$ and partially enclosing a crimped or compressed portion of the stent 10. In other words, the stent 10 is partially sheathed. The valve 12 is in an uncompressed, uncrimped, and unsheathed portion of the stent 10, such that the valve is in a natural (e.g., undeformed) operable configuration and not subject to forces that may induce plastic deformation. The trigger safety 142 is engaged around the outer supports 110 at a first trigger safety notch 144a (not visible in FIG. 6A1, but see FIG. 6B1) at position $P_s t_1$. A second trigger safety notch 144b is visible. The distal trigger 116 is positioned adjacent the trigger safety 142 at position $P_s d_1$. The proximal trigger 114 is positioned at position $P_s p_1$ substantially in abutment with the handle 106 and at or toward a proximal end of the one or more trigger guide slots 150 of the outer supports 110.

FIG. 6B1 is a side view of the stent delivery system 100 partially through the sheathing process and in a similar position as in FIG. 5F1. FIG. 6B2 is an enlarged cross-sectional side view of the distal region of the stent delivery system 100 showing the stent 10 being drawn into and sheathed within the pod 134. Referring generally and collectively to FIGS. 6B1 and 6B2, as the sheathing tube 202 and the sheathing funnel 204 are moved distally relative to the handle 106, the outer sheath 126, the trigger safety 142, the distal trigger 116, and the proximal trigger 114 also move distally relative to the handle 106. The pod 134 may be slightly displaced from position $P_s pod_1$ and is now at position $P_s pod_2$. The displacement may be due to frictional forces (as depicted) or may be due to the flanges 218 engaging and being moved by the sheathing funnel 204 and/or the sheathing tube 202. Also, the trigger safety 142 is displaced from position $P_s t_1$ to position $P_s t_2$, distally toward the second trigger safety notch 144b. Similarly, the distal trigger 116 is displaced distally from position $P_s d_1$ to position $P_s d_2$ and the proximal trigger 114 is displaced from position $P_s p_1$ to position $P_s p_2$. Although not visible in FIG. 6B1, the internal connector 120 and the floater 118 also move distally. More particularly, the sheathing tube 202 and sheathing funnel 204 are pushed distally, in turn pulling the pod 134 from position $P_s pod_1$ to position $P_s pod_2$, the outer sheath 126 the internal connector 120, the trigger safety 142 from position $P_s t_1$ to position $P_s t_2$, the distal trigger 116 from position $P_s d_1$ to position $P4_2$, the floater 118 and the proximal trigger 114 from position $P_s p_1$ to position $P_s p_2$. The movement of these components may continue until the trigger safety 142 engages the second trigger safety notch 144b. An audible click may be made by the trigger safety 142 as it engages the second trigger safety notch 144b. The first trigger safety notch 144a is now visible.

FIG. 6C1 is a side view of the stent delivery system 100 at a completion of distal movement of the sheathing tube 202 and the sheathing funnel 204 during the sheathing process and in a similar position as in FIG. 5G1. FIG. 6C2 is an enlarged cross-sectional side view of the pod 134 and the stent 10 sheathed within the pod 134. Referring generally and collectively to FIGS. 6C1 and 6C2, the stent 10 is fully sheathed. The pod 134 is now displaced from position $P_s pod_2$ to position $P_s pod_3$. Additional distal displacement of the sheathing tube 202 and/or sheathing funnel 204 resulted in abutment of the flanges 218 with the collar 205 disposed within the sheathing tube 202 and/or sheathing funnel 204. The collar 205 in turn transfers force in the longitudinal direction to the flanges 218, resulting in longitudinal movement of the sheathing fingers 206 and movement of the pod 134 over the crimped stent 10 from position $P_s pod_2$ to position $P_s pod_3$ The distal trigger 116 and proximal trigger 114 are also shifted distally in preparation for retraction to deploy the stent 10. Specifically, the distal trigger 116 is now shown displaced distally from position $P_s d_2$ to position $P_s d_3$ and the proximal trigger 114 is displaced from position $P_s p_2$ to position $P_s p_3$. Although not visible in FIG. 6C1, the internal connector 120 and the floater 118 are also displaced distally. The trigger safety 142 is displaced from position $P_s t_2$ to position $P_s t_3$ in engagement with the second trigger safety notch 144b to limit (e.g., prevent) inadvertent deployment of the stent 10. The flanges 218 of the sheathing fingers 206 are also engaged with the collar 205 that may be disposed within the sheathing funnel 204 and/or the sheathing tube 202. Accordingly, further distal movement of the sheathing funnel 204 and/or the sheathing tube 202 may result in distal movement of the sheathing fingers 206, which in turn results in distal movement of the pod 134 and outer sheath 126.

FIG. 6D1 is a side view of the stent delivery system 100 in a fully sheathed delivery configuration similar to the configuration in FIG. 5I. FIG. 6D1 illustrates the sheathing tube 202, sheathing funnel 204 and the sheathing fingers 206 removed after the sheathing process. FIG. 6D2 is an enlarged cross-sectional side view of the distal region of the stent delivery system 100 with the stent 10 fully sheathed within the pod 134. Referring generally and collectively to FIGS. 6D1 and 6D2, the one or more spacers 121a, 121b, 121c (collectively 121) can be seen positioned around a portion of the distal inner segment 136. The spacers 121 may be free floating around (e.g., coaxially with) a portion of the distal inner segment 136. The spacers 121 may provide a surface or other support structure against which the panchor 128 (or segments of the panchor 128) may abut to restrict proximal and/or distal movement of the panchor 128, or segment thereof, relative to, for example, the tip 132. During sheathing of a stent, for example, forces may be exerted on the stent in a distal direction, which in turn may create forces in a distal direction on the panchor 128, including individual segments of the panchor 128. The distal forces on the panchor 128 may cause the segments of the panchor 128, for example, to tend to separate. The one or more spacers 121 may restrict and/or prevent separation of panchor segments due to distal forces on the panchor 128 created during sheathing. The segments of a panchor 128 are shown in FIGS. 14B-14E and described below with reference to the same.

In one embodiment, a first spacer 121a may abut with and/or engage the panchor 128. The first spacer 121a may have an outer diameter sized to allow the first spacer 121a to abut and/or engage an inner surface of the panchor 128. The second spacer 121b may abut a distal end of the first spacer 121a and have an outer diameter that is larger than the outer diameter of the first spacer 121a. The larger diameter of the second spacer 121b may enable the second spacer to engage the panchor 128 and restrict distal movement of the panchor 128, including individual segments of the panchor 128. More specifically, the second spacer 121b may have an outer diameter large enough to engage an inner surface of a socket portion of the panchor 128 and thereby limit distal movement of a corresponding segment of the panchor 128, for example relative to the tip 132. The third spacer 121c may abut a distal end of the second spacer 121b and extend distally to abut the tip 132 and/or an outer tube portion 136b of the distal inner segment 136. The distal inner segment 136 may comprise an outer tube portion 136b and an inner tube portion 136a positioned coaxially within the outer tube portion 136b. The outer tube portion 136b may extend a portion of the length of the distal inner segment 136 and provide a protruding surface (e.g., protruding relative to the inner tube portion) against which the third spacer 121a can abut. The inner tube portion 136a may extend the length of the distal inner segment 136 from the tip to the connection member 138. The outer tube portion 136b may be bonded to the inner tube portion 136a.

FIG. 7A is a cross-sectional view of the stent delivery system 100 in the fully sheathed delivery configuration preparatory to use in a medical procedure, prior to the trigger safety 142 being removed. The trigger safety 142 is engaged around the outer supports 110 at the second trigger safety notch 144b. FIG. 7A portrays an interrelation of various components of the stent delivery system 100, including but not limited to the handle 106, the outer supports 110, the floater 118, the triggers 114, 116, the trigger safety 142, the internal connector 120, the sheathing grip 112, the outer sheath 126, the middle sheath 124, the inner member 122, the panchor 128, the pod 134 and the tip 132. FIG. 7B is a close-up cross-sectional view of the stent 10 in a compressed configuration within the pod 134. The panchor 128 may include an anchor 198 configured to be positioned between connectors 18 of the stent 10 that interconnect annular segments 14 (or rows of struts 16 or strut arms) in a scaffolding structure of the stent 10. The anchors 198 may engage the distal ends of the struts 16 and thereby engage the stent 10 to limit distal movement of the stent 10 relative to the panchor 128. For example, the anchors 198 may be arranged radially to be positioned circumferentially between the connectors 18. The stent 10 is compressed around the panchor 128 and/or the distal inner segment 136. The spacers 121a, 121b, 121c, may be disposed between the distal inner segment 136 and the panchor 128 and/or the stent 10.

FIGS. 8A1-8A2, 8B1-8B2, 8C1-8C2, and 8D are side longitudinal cross-sectional views of the trigger assembly of the stent delivery system 100, at various positions during deployment of the stent 10. FIGS. 8A1-8A2, 8B1-8B2, 8C1-8C2, and 8D illustrate operation of the proximal trigger 114, the floater 118, the distal trigger 116, the internal connector 120, and the outer sheath 126 to deploy a stent 10.

Figure 8D:
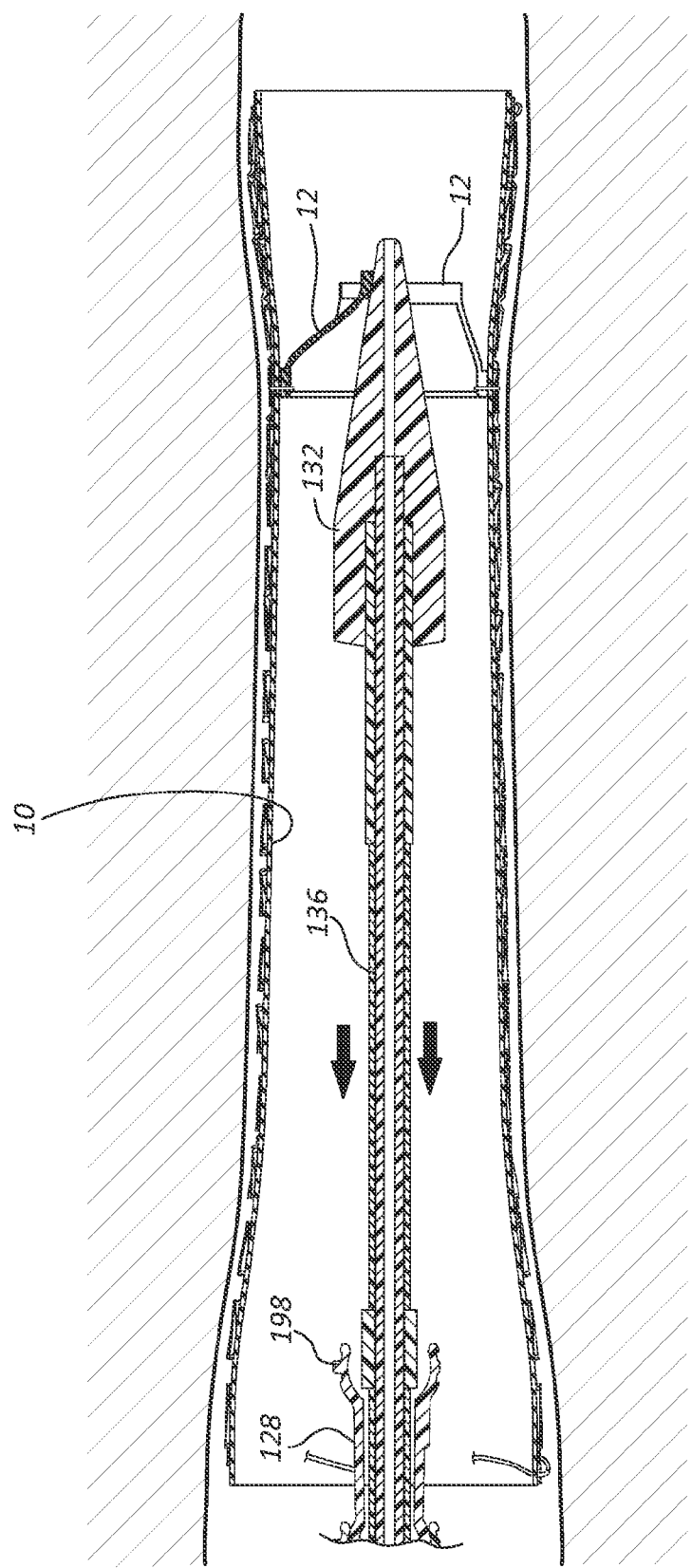
FIG. 8D is a close-up, side longitudinal, cross-sectional view of the stent delivery system of FIG. 1 with the stent in a fully expanded, deployed state.

FIG. 8A1 shows the stent delivery system 100 with the trigger safety 142 removed. The stent delivery system 100 may be ready to deploy the stent 10. The pod 134 is abutting the tip 132 at position $P_dpod_1$, completely over and fully enclosing the collapsed stent 10. The distal trigger 116 is positioned substantially at or toward the distal end of the one or more trigger guide slots 150 (see e.g., FIG. 2) of the outer supports 110 at position $P_dd_1$. The proximal trigger 114 is positioned at position $P_dp_1$. The trigger safety 142 is removed (and therefore is not shown in FIGS. 8A1-8A2, 8B1-8B2, 8C1-8C2, and 8D), thereby allowing retraction of the triggers 114, 116 and deployment of the stent 10 to occur. FIG. 8A2 is a close up view of the panchor 128 engaging the compressed and fully sheathed stent 10 within the pod 134.

FIG. 8B1 is a side longitudinal cross-sectional view of the stent delivery system 100 with the proximal trigger 114 retracted from position $P_dp_1$ to position $P_dp_2$. and the stent 10 partially deployed. Proximal retraction of the proximal trigger 114 results in proximal retraction of the floater 118, which in turn displaces the distal trigger 116 from $P_dd_1$ to position $P_dd_2$. As shown, position $P_dd_2$ may be substantially proximate to position $P_dp_1$. Proximal retraction of the distal trigger 116 may result in proximal retraction of the internal connector 120 and the outer sheath 126. Proximal retraction of the outer sheath 126 results in at least partial deployment of the stent 10. The pod 134 is shown displaced proximally from position $P_dpod_1$ to position $P_dpod_2$, away from the tip 132, exposing a portion of the stent 10. The stent 10, which is expanded in the area exposed outside the pod 134, is partially deployed. When the proximal trigger 114 is fully retracted, a practitioner can more easily reach the distal trigger 116. FIG. 8B2 is a close up view of the partially deployed stent 10 partially compressed within the pod 134.

FIGS. 8C1 and 8C2 are side longitudinal cross-sectional views of the stent delivery system 100 with the distal trigger 116 fully retracted from position $P_dd_1$ to position $P_dd_3$. The floater 118 is telescoped into the internal connector 120. The pod 134 is completely retracted, from position $P_dpod_1$ to position $P_dpod_3$, fully withdrawn from the stent 10 allowing the stent 10 to fully expand and deploy.

As described above, the design and coupling of the floater 118 to the internal connector 120 (and/or distal trigger 116) allow the internal connector 120 and distal trigger 116 to move proximally relative to the floater 118 and the proximal trigger 114, thus enabling the two-trigger mechanism of the stent delivery system 100. The two-trigger mechanism enables serial retraction of the triggers 114, 116. A two-trigger design allows an elegant, ergonomic mechanism to enable a practitioner to deploy a longer stent (e.g., a stent with a length longer than the finger span of the practitioner).

The two-trigger design also allows a two-stage stent deployment process, enabling repositioning of the stent after partial deployment and before complete deployment. A three-trigger design enables deployment of still longer stents, as described below with reference to FIGS. 16A, 16B, 17A, 17B, and 18A-18C. Typically, a maximum trigger reach of a hand of a woman over sixty years of age in the fifth percentile is approximately 3.4 inches. Accordingly, the distance between the triggers and/or handle may be no greater than approximately 3.4 inches. Accordingly, the distance between the triggers and/or handle may be less than approximately 3.4 inches.

FIG. 8D is a close-up view of the stent 10 in the fully expanded, deployed state within a lumen of the body. The tip 132 and distal inner segment 136 are shown as being partially withdrawn proximally (in the direction of the arrows) through the valve 12 of the stent 10.

FIGS. 9A and 9B are a transverse cross-sectional view and a longitudinal cross-sectional view, respectively, of a portion of the stent delivery system 100. FIG. 9A provides a transverse cross-sectional view of the stent delivery system 100 through the trigger safety 142. FIG. 9A illustrates the nested positioning of the trigger safety 142, the outer supports 110, the floater 118, the rigid support tube 108, and the inner member 122.

FIG. 9B provides a top longitudinal cross-sectional view of the stent delivery system 100. FIG. 9B illustrates a number of component relationships, according to one embodiment. Looking from right to left on the figure, the outer sheath 126 is received into and bonded to an interior surface of the internal connector 120. The internal connector 120 passes through and engages the distal trigger 116. Specifically, one or more protrusions 152 (see e.g., FIG. 3) extending radially outward from the internal connector 120 engage the distal trigger 116. As shown in FIG. 9B, a first pair of protrusions 152a are configured to engage and/or abut a proximal end of the distal trigger 116 and a second pair of protrusions 152b are configured to engage and/or abut a distal end of the distal trigger 116. The floater 118 couples together the proximal trigger 114 and the internal connector 120 and distal trigger 116. In the illustrated embodiment, the distal engagement mechanism 172 (FIG. 3) of the floater 118 engages the internal connector 120 and the proximal engagement connector 174 engages the floater engagement ring 170 (FIG. 10A) of the proximal trigger 114. The rigid support tube 108 extends within the floater 118 and the internal connector 120 and around the inner member 122.

The trigger safety 142 is wrapped around or otherwise engages the outer supports 110. Inward protrusions 188 of the trigger safety 142 engage a trigger safety notch 144b formed by the outer supports 110 to limit proximal movement of the trigger safety 142 relative to the outer supports 110. Alignment ribs 189 protruding inward from an inner surface of the trigger safety 142 are received into the trigger guide slots 150 (see e.g., FIG. 9A) and align the trigger safety 142. The alignment ribs 189 may also engage a third pair of protrusions 152c on the internal connector 120 radiating outward. The engagement of the alignment ribs 189 with the protrusions 152c of the internal connector 120 limits proximal movement of the internal connector 120 relative to the trigger safety 142 and the outer supports, thereby restricting deployment of the stent 10. The second pair of protrusions 152b may also be configured to engage alignment ribs 189 of the trigger safety, such that distal movement of the internal connector 120 may result in distal movement of the trigger safety 142, for example during sheathing of a stent.

FIGS. 10A and 10B are end views of the triggers 114, 116 of the stent delivery system 100 of FIG. 1. FIG. 10A is an end view of the proximal trigger 114 and FIG. 10B is an end view of the distal trigger 116.

Referring to FIG. 10A, the proximal trigger 114 may have a ring-shaped base 164 and a pair of finger holds 166 extending radially outward from the outer surface of the base 164 directly opposite one another. One or more trigger guides 168 may protrude radially inward from the base 164 to engage the trigger guide slot 150 formed by the outer supports 110 (FIGS. 2, 9A). The trigger guides 168 may restrict rotation of the proximal trigger 114 about the outer supports 110 while allowing proximal and distal movement of the proximal trigger 114. The proximal trigger 114 may also include a floater engagement ring 170 to engage the proximal engagement mechanism 174 (FIG. 3) of the floater 118, such that proximal movement of the proximal trigger 114 results in proximal movement of the floater 118.

Referring to FIG. 10B, the distal trigger 116 may be configured similarly to the proximal trigger 114, having a ring-shaped base 154 with a pair of finger holds 156 extending radially outward from the outer surface of the base 154 directly opposite one another. One or more trigger guides 158 may protrude radially inward from the base 154 to engage the trigger guide slot 150 formed by the outer supports 110 (FIGS. 2, 9A, 9B). The trigger guides 158 may restrict rotation of the distal trigger 116 about the outer supports 110 while allowing proximal and distal movement of the distal trigger 116. The distal trigger 116 is configured to engage or otherwise couple to the internal connector 120 (FIGS. 3, 9A, 9B).

FIGS. 11A and 11B are a side view and a top cross-sectional view, respectively, of an internal connector 120, a distal trigger 116, a floater 118, and a proximal trigger 114 of the stent delivery system 100. FIGS. 11A and 11B illustrate the coupling relationship of the internal connector 120, the distal trigger 116, the floater 118, and the proximal trigger 114. Referring collectively to FIGS. 11A and 11B, the distal trigger 116 couples to the internal connector 120. In the illustrated embodiment, the one or more outwardly extending protrusions 152 on the internal connector 120 mate with the trigger guides 158. As the distal trigger 116 is retracted proximally, toward the handle 106, the distal trigger 116 retracts the internal connector 120 proximally. Thus, retraction of the distal trigger 116 results in retraction of the outer sheath 126 and pod 134 (FIGS. 2 and 3), which results in at least partial deployment of the stent 10.

The proximal trigger 114 is mechanically coupled to the distal trigger 116 by the floater 118. In the illustrated embodiment, the proximal trigger 114 further includes a floater engagement ring 170 coupled to the inwardly protruding trigger guides 168 (see also FIG. 10A). The floater engagement ring 170 may engage the proximal engagement mechanism 174 at the proximal end of the floater 118, such that proximal movement of the proximal trigger 114 in turn retracts the floater 118. The distal end of the floater in turn engages the distal trigger 116 and/or the internal connector 120. Accordingly, retraction of the proximal trigger 114 results in retraction of the distal trigger 116 and/or the internal connector 120, which results in at least partial deployment of the stent 10.

Figure 12B:
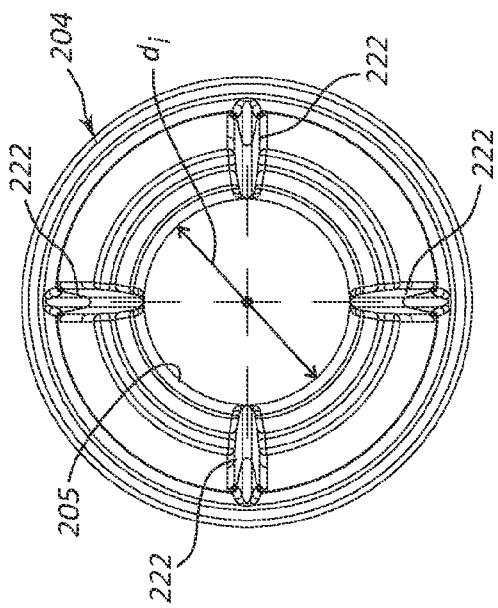
FIG. 12B is an end view of the sheathing funnel of the stent delivery system of FIG. 1.
Figure 12C:
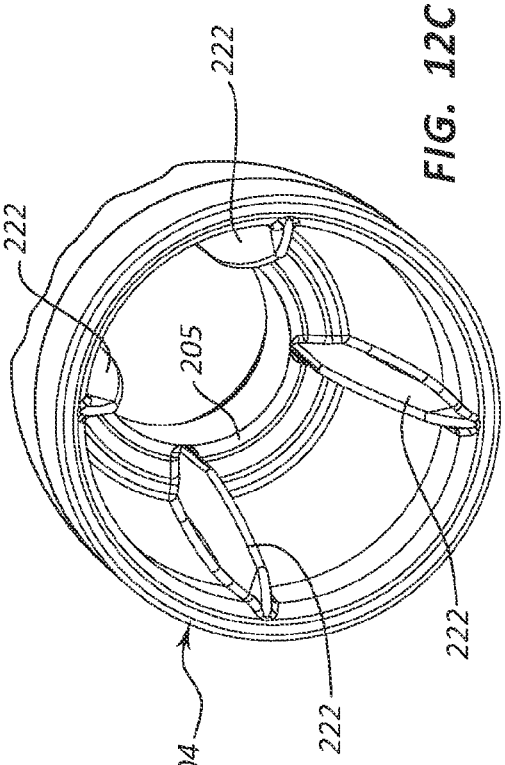
FIG. 12C is a perspective view of the sheathing funnel of the stent delivery system of FIG. 1.
Figure 12A:
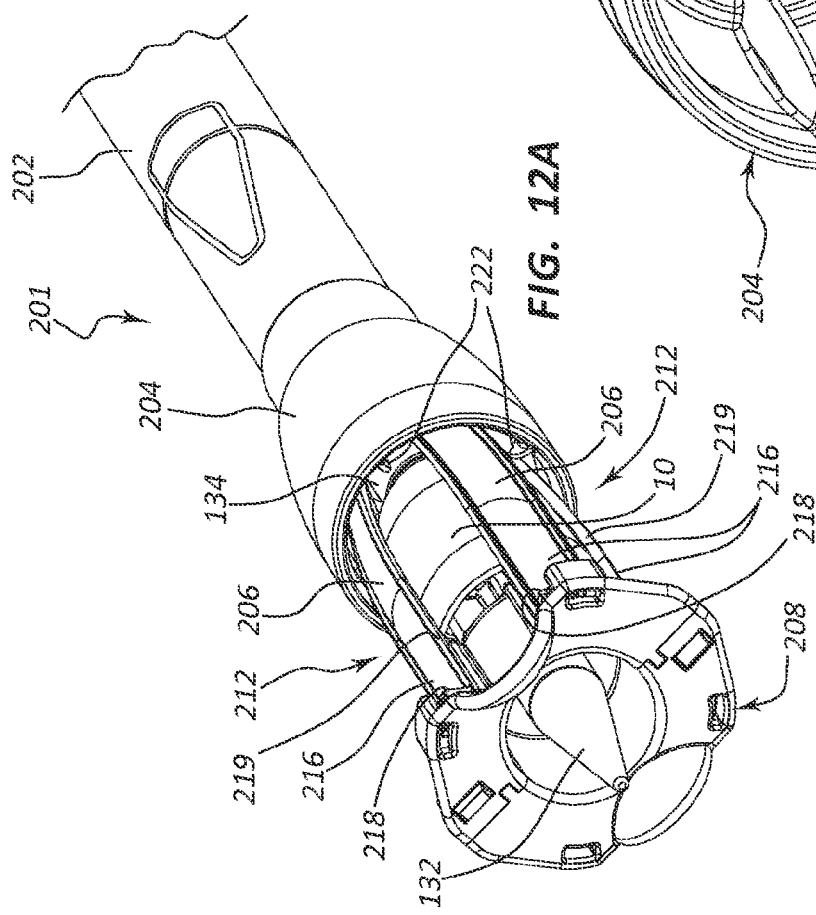
FIG. 12A is a perspective view of the sheathing funnel and sheathing tube of the stent delivery system of FIG. 1.

FIGS. 12A-12C are various views of the sheathing funnel 204 and sheathing tube 202 of the stent delivery system 100. FIG. 12A is a perspective view of the sheathing mechanism 201 disposed at the distal end of a stent delivery device 101 and showing positioning of the sheathing funnel 204 and sheathing tube 202 in the assembled sheathing mechanism 201. FIG. 12B is an end view of the sheathing funnel 204 and FIG. 12C is a perspective end view of the sheathing funnel 204.

Referring collectively to FIGS. 12A-12C, the sheathing tube 202 may have a tube-like cylindrical shape. The inner diameter $d_i$ of a lumen of the sheathing tube 202 may be sized and shaped to be positioned over an outer diameter of a distal region of the outer sheath 126 and/or the pod 134 of the delivery device 101. Furthermore, a lumen of the sheathing tube 202 may have an inner diameter configured to allow the sheathing tube 202 to be slidably moveable relative to the outer sheath 126 and/or the pod 134. The sheathing tube 202 may slide relative to the outer sheath 126 and relative to the pod 134 without interference. The sheathing tube 202 may also slide relative to the sheathing fingers 206.

The sheathing funnel 204 may be disposed at a distal end of the sheathing tube 202. A proximal end of the sheathing funnel 204 may be coupled to the sheathing tube 202 in a manner that the inner diameter of the sheathing funnel 204 at the proximal end is approximately equivalent to the inner diameter $d_i$ of the sheathing tube 202 at the distal end. The sheathing funnel 204 has an internal taper configured to guide an expanded portion of a stent 10 and the sheathing fingers 206 into the sheathing tube 202. Accordingly, the distal end of the sheathing funnel 204 may have an inner diameter that is larger than the inner diameter $d_i$ of the proximal end of the sheathing funnel 204 and the inner diameter of the sheathing funnel 204 may taper from the distal end to the proximal end.

The sheathing funnel 204 may include ribs 222 disposed on an internal surface of the sheathing funnel 204 and extending in a direction generally from the distal end to the proximal end of the sheathing funnel 204. The ribs 222 may be configured to interact with the sheathing fingers 206 to cause the sheathing fingers 206 to align with the ribs 222 such that an elongate projection 216 of a flared region 212 of the sheathing fingers 206 is positioned on either side of each rib 222 and the ribs 222 are positioned in the gaps between the flared regions 212. The ribs 222 also interact with the stent 10 during sheathing. The sheathing funnel 204, and particularly the ribs 222, guides the stent 10 and the sheathing fingers 206 into the sheathing tube 202 to crimp the stent 10 during sheathing. The crimped stent 10 can then be sheathed or drawn into the pod 134.

The elongate projections 216 of the sheathing finger 206 may include one or more rails 219 or similar thicker portion disposed on an outer surface and configured to contact the inner surface of the sheathing funnel 204 and/or sheathing tube 202 during a sheathing process. The rails 219 may function to reduce frictional forces between the projections 216 and the sheathing funnel 204 and/or sheathing tube 202 during sheathing of a stent 10.

The sheathing funnel 204 and/or sheathing tube 202 may include and/or define an annular collar 205 on an interior surface of the sheathing funnel 204 and/or sheathing tube 202. The collar 205 may be configured to engage and cause distal movement of the flanges 218 (at a distal end of the elongate projections 216 of the flared portion 212 of the sheathing fingers 206) as the sheathing funnel 204 and/or sheathing tube 202 is advanced distally over the sheathing fingers 206. Engagement of the collar 205 with the flanges 218 during distal movement of the collar 205 may result in distal movement of the sheathing fingers 206, resulting in distal movement of the pod 134 to sheathe the crimped portion of the stent 10.

FIGS. 13A-13C are a trigger safety 142 of the stent delivery system 100, according to one embodiment. FIG. 13A is a perspective view of the trigger safety 142. FIG. 13B is a side view of the trigger safety 142 in a closed state. FIG. 13C is a side view of the trigger safety 142 in an open state.

Referring collectively to FIGS. 13A-13C, the trigger safety 142 may include an annular body 182 and a release tab 184. The annular body 182 may be configured to, in a closed configuration, encircle and engage the outer supports 110 (shown in FIG. 9A). The release tab 184 releases the annular body 182 to open the annular body 182 to allow the annular body 182 to transition to an open configuration and disengage from the outer supports 110 and thereby release the trigger safety 142. The annular body 182 may further include various protrusions 188 and ribs 189 on an inner surface to engage or otherwise interact with the outer supports 110.

The body 182 may have an annular shape configured to wrap around the outer supports 110 of the stent delivery device 101. The body 182 may comprise a hinge 186 to allow the body 182 to open and disengage from the outer supports 110. One or more inward protrusions 188 may be configured to engage a trigger safety notch 144a, 144b (shown in FIGS. 3, 5F1, 6B1, and 9B) of the outer supports 110.

The protrusions 188 may each extend inwardly from a deflectable tab 187 formed in the body 182 and be designed and configured to allow distal movement of the trigger safety 142 (for sheathing) while restricting proximal movement of the trigger safety 142. Specifically, the trigger safety 142, when in an operable state and engaged with the first trigger safety notch 144a (see e.g., FIG. 3), may be moved distally from the first trigger safety notch 144a to the second trigger safety notch 144b (see e.g., FIG. 3). The deflectable tabs 187 may enable the protrusions 188 to withdraw from engagement with the trigger safety notches 144.

The protrusions 188 may have a ramped distal side configured to interact with a distal edge of the first trigger safety notch 144a as the trigger safety 142 is moved distally. The proximal side of the protrusions may be straight, or unramped, and configured to engage the proximal edge of the trigger safety notches 144 (see e.g., FIG. 3) and thereby restrict proximal movement of the trigger safety 142 relative to the outer supports 110. The ramped distal side may act as a ramp to cause the protrusions 188 to be raised out of engagement with the first trigger safety notch 144a in response to distal movement of the trigger safety 142 relative to the outer supports 110. The ramped distal side may interact with a distal edge of the trigger safety notches 144, which urges the protrusion out of the trigger safety notch. As the protrusions 188 rise out of engagement with first trigger safety notch 144a, the deflectable tabs 187 bend or deflect to a deflected state to accommodate the outward shift of the protrusions 188.

The deflectable tabs 187 may be biased toward an undeflected state. When the proximal side of the protrusions 188 reach the second trigger safety notch 144b, the deflectable tabs spring back to the undeflected state causing the protrusions 188 to engage the second trigger safety notch 144b and restrict proximal movement of the trigger safety 142. The springing back of the deflectable tabs 187 and the protrusions 188 may cause an audible click to signal that the stent delivery system 100 has reached the fully sheathed delivery configuration.

One or more alignment ribs 189 (or similar protrusions) disposed on the inner surface of the body 182 are configured to be received in the trigger guide slot 150 (see e.g., FIG. 2) to appropriately align the trigger safety 142. The ribs 189 are also configured to engage the protrusions 152 on the internal connector 120 (FIGS. 3, 9A, 9B) and restrict proximal movement of the internal connector 120 and distal trigger 116 (see e.g., FIG. 2). When the internal connector 120 is unable to move proximally, the floater 118 (see e.g., FIGS. 3, 9B), the proximal trigger 114 (FIGS. 3, 9B) and the outer sheath 126 also cannot move proximally. In this manner, the trigger safety 142 may guard against inadvertent or accidental deployment of a sheathed stent.

Described differently, the ribs 189 may be configured to restrict movement of the internal connector 120 (and thus the outer sheath 126) relative to the trigger safety 142 when the annular body 182 is in the closed configuration around the outer supports 110 of the stent delivery device 101. The protrusions 188 may be configured to engage the trigger safety notches 144 of the outer supports 110 of the stent delivery device 101 when the annular body is in the closed configuration and restrict proximal movement of the trigger safety 142 relative to the outer supports 110 of the delivery device 101. The protrusions 188 in combination with the deflectable tabs 187 permit distal movement of the trigger safety 142 relative to the outer supports 110 of the stent delivery device 101 to allow distal movement of the outer sheath 126 relative to the inner member 122 (and, among other things, the panchor 128 and the stent 10) of the tubular member of the stent delivery device 101. The distal movement of the trigger safety 142 relative to the housing allows the transition of the stent delivery device 101 from the partially sheathed configuration to the fully sheathed delivery configuration during a sheathing process.

The release tab 184 of the trigger safety 142 allows for simple and convenient release of the trigger safety 142 from engagement around the outer supports 110. In the illustrated embodiment, the release tab 184 is a tongue-like projection extending away from the body 182 and oriented substantially at a tangent to the ring-like body 182. The release tab 184 may be coupled to the body 182 by one or more hinged extensions 190. The hinged extensions 190 may include a hinge 192 to allow the hinged extensions 190 and the release tab 184 to rotate away from the body 182. The release tab 184 may engage a projection 194 on the body 182 so as to maintain the body 182 in a closed position. As shown in FIG. 13C, lifting or pulling the release tab 184 away from the body 182 may cause the hinged extensions 190 and the release tab 184 to rotate away from the body 182. As the release tab 184 rotates away from the body 182, the release tab 184 disengages from the projection 194 and allows the body 182 to open. Once the trigger safety 142 is open, it can be removed from the outer supports 110 to allow operation of the trigger assembly 102.

FIGS. 14A-14H are views of the panchor 128 of the stent delivery system 100, according to one embodiment of the present disclosure. The panchor includes a base segment 230 and one or more extension segments 232. FIG. 14A is a perspective view of a base segment 230. The base segment 230 alone can function as a panchor, by itself, according to one embodiment. FIG. 14B is a perspective view of the panchor 128 of the stent delivery system 100 and illustrates an extension segment 232 coupled to the base segment 230. FIG. 14C is a side view of the panchor 128. FIG. 14D is a top view and FIG. 14E is a bottom exploded view of the panchor 128. FIGS. 14F and 14G are end views of the panchor 128. FIG. 14H is a cross-sectional view of the panchor 128.

Referring to FIGS. 14A-14H, collectively, the panchor 128 may include a push surface 196 and one or more anchors 198. The push surface 196 may be oriented orthogonal to an outer surface of the base segment 230. For example, the push surface 198 may be disposed on a flange positioned annularly around the base segment 230. The push surface 196 is configured to restrict proximal movement of the stent 10 as the outer sheath 126 is pulled proximally over the stent 10 during deployment. The anchors 198 may include a flange at a distal end of the base segment 230 and/or the distal end of the one or more extension segments 232 of the panchor 128. In the illustrated embodiment, the anchors 198 may include a plurality (e.g., five) of protrusions or apices about the circumference of a distal end of the base segment 230 and/or one or more extension segments 232. For example, the anchors 198 may be a pentagon shaped annular flange having five apices. The protrusions of each anchor 198 may be configured to be positioned between connectors of the stent 10 that interconnect annular segments (or rows of struts or strut arms) in the scaffolding of structure of the stent 10. For example, the anchors 198 may be arranged radially to be positioned circumferentially between the connectors of a stent 10. The anchors 198 may engage the distal ends of the struts and thereby engage the stent to limit distal movement of the stent relative to the panchor 128.

Engagement of the struts by the anchors 198 of the panchor 128 may restrict distal movement of the stent 10, so long as the proximal end of the stent 10 remains sheathed within the pod 134 and compressed around the panchor 128. One or more deflectable tabs 129 may be positioned at an opening within the panchor 128. The deflectable tabs 129 may be configured to deflect (e.g., spread apart) in response to contact with a tapered or ramped surface of a barb of a connection member that couples the distal inner segment to the distal end of the inner member 122 (see e.g., FIG. 3). The deflectable tabs 129 may retract to abut the orthogonal surface(s) of the barb and thereby restrict passage of the barb back out of the opening within the panchor 128, thereby securing the barb in place.

The plurality of segments 128, namely the base segment 230 and one or more extension segments 232, may be rotatably and/or flexibly coupled to enable the panchor 128 to be flexible. In the illustrated embodiment, the segments 230, 232 may comprise ball 234 and socket 236 connections. A ball 234 at a proximal end of the extension segments 232 fits into and is received by a socket 236 at the distal end of the base segment 230 or another extension segment 232. The ball 234 and socket 236 connection allows the segments 230, 232 to bend and rotate relative to each other. An embodiment of a panchor 128 having a plurality of extension segments 232 in a curved configuration is shown in FIG. 18C.

FIGS. 15A-15C are views of a tip insertion funnel 208 of the stent delivery system of FIG. 1. FIGS. 15A and 15B illustrate the tip insertion funnel 208 in a closed state and FIG. 15C illustrates the tip insertion funnel 208 in an open state. The tip insertion funnel 208 may form a large opening 260 at a distal end that tapers to a small opening 262 configured to guide the distal inner segment 136 into the panchor 128. Specifically, the tip insertion funnel 208 may precisely guide the proximal end of the distal inner segment 136 retrograde through a valve of a stent to avert undesired contact and/or damage, for example, to leaflets of the valve or other portion of the valve, as a result of imprecise insertion of the distal inner segment 136.

In the illustrated embodiment, the tip insertion funnel 208 may comprise two halves 242a, 242b and hinges 244 at a distal end of the tip insertion funnel 208, near the larger distal opening 260. The hinges 244 hingedly couple the halves 242a, 242b together. The hinges 242 may be disposed in a rim 246 around the outer circumference of the distal opening of the tip insertion funnel 208. The hinges 242 may allow the tip insertion funnel 208 to open as shown in FIG. 15C and to be withdrawn over the tip 132 (see e.g., FIG. 3) for removal after insertion of the distal inner segment 136 into the panchor 128. The tip insertion funnel 208 may include removal features 248 (e.g. finger grips) to aid in removing the tip insertion funnel 208. In the illustrated embodiment, a removal feature 248 is disposed on each of the halves 242a, 242b on the distal side of the rim 246. The removal features are configured to be squeezed together to rotate the halves 242a, 242b relative to each other about the hinges 244 to open the tip insertion funnel 208.

Figure 16A:
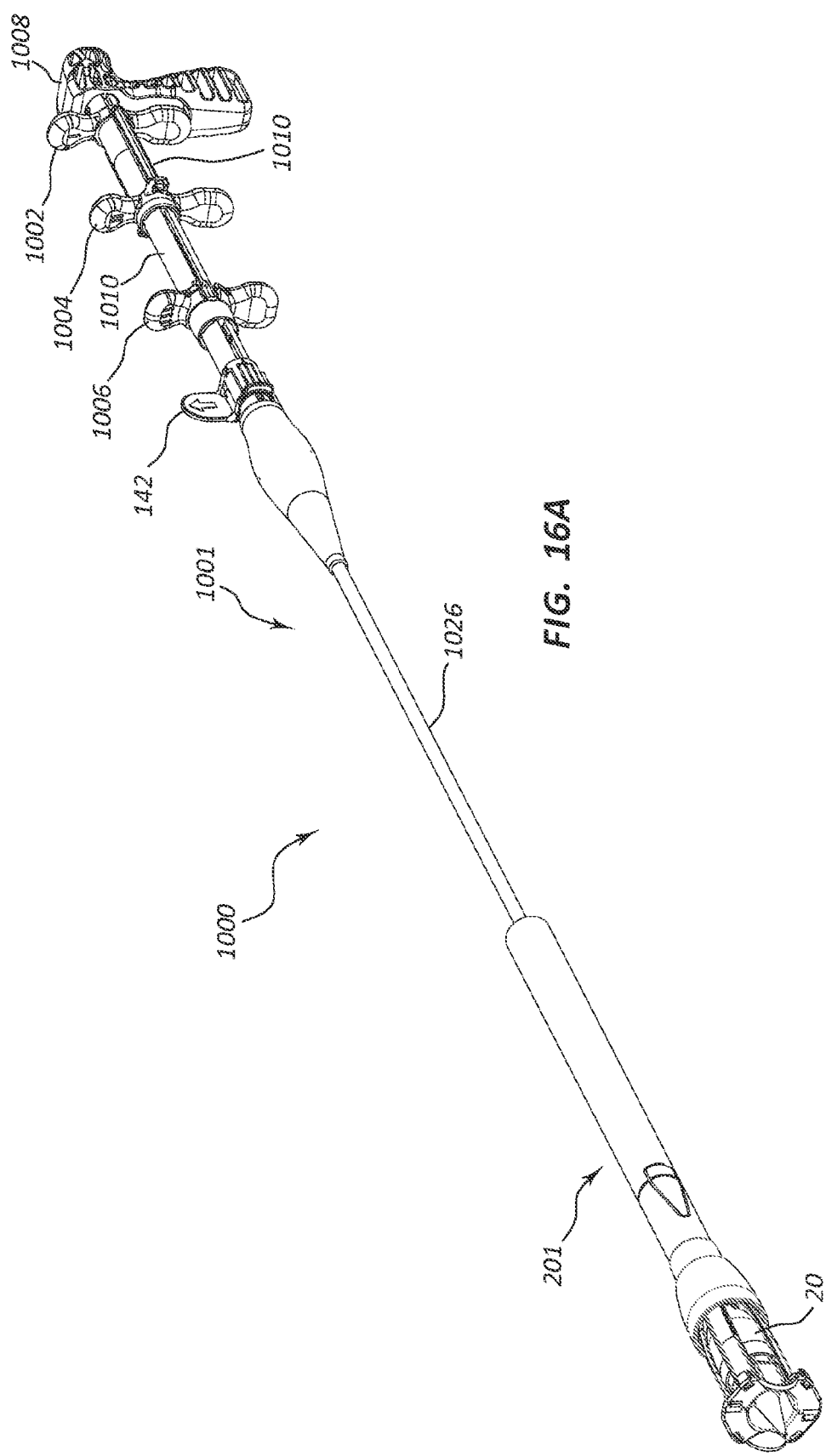
FIG. 16A is a perspective view of a stent delivery system having three triggers in a partially sheathed configuration, according to another embodiment of the present disclosure.
Figure 16B:
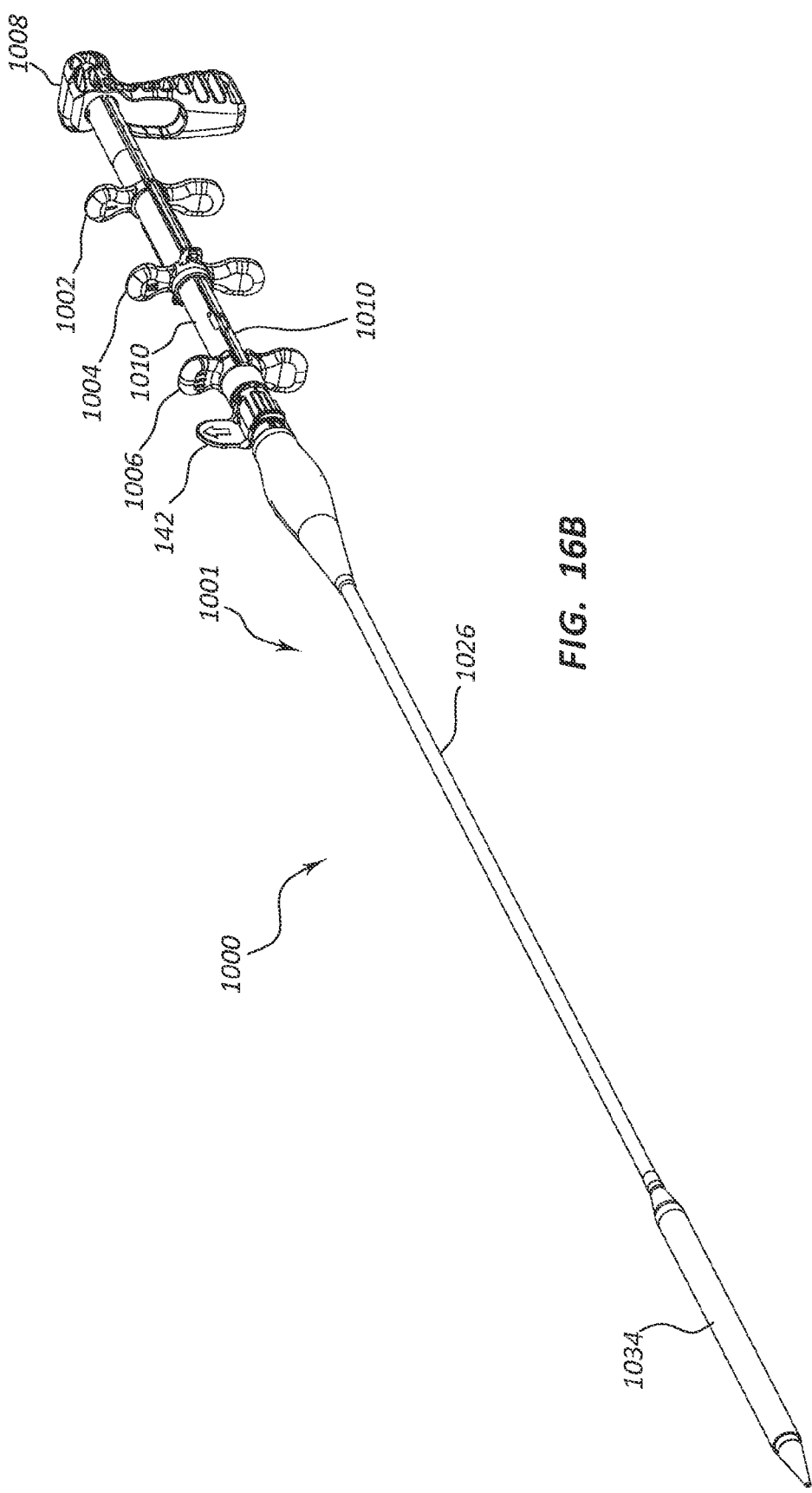
FIG. 16B is a perspective view of the stent delivery system of FIG. 16A in a fully sheathed delivery configuration.

FIGS. 16A-16B are perspective views of a stent delivery system 1000 having three triggers, according to another embodiment of the present disclosure. FIG. 16A is a perspective view of the stent delivery system 1000 in a partially sheathed configuration. FIG. 16B is a perspective view of the stent delivery device 1001 in a fully sheathed delivery configuration. Referring generally and collectively to FIGS. 16A-16B, the stent delivery system 1000 has three triggers 1002, 1004, 1006 that a practitioner can manipulate to retract an outer sheath 1026 and pod 1034 to deploy a stent 20. The stent 20 may have a longer length, for example 150 mm, that may be more easily deployed with a three-stage, three-trigger deployment mechanism.

Other components of the stent delivery system 1000 may be substantially similar to the components of stent delivery system 100 described in detail above. The three triggers 1002, 1004, and 1006 may be operated sequentially, each to partially deploy the stent 20. The first trigger 1002 may be pulled proximally, toward a handle 1008, to partially deploy the stent 20. A second trigger 1004 may then be pulled proximally, toward the handle 1008 and the first trigger 1002, to further deploy the stent 20. Finally, a third trigger 1006 may be pulled proximally, toward the handle 1008, the first trigger 1002, and the second trigger 1004, to complete deployment of the stent 20. A trigger safety 142 may limit proximal movement of the third trigger 1006 (and also limit proximal movement of the first trigger 1002 and second trigger 1004), thereby restricting deployment of the stent 20. The trigger safety 142 may operate by engaging outer supports 1010 and an internal connector (not shown) similar to the manner previously described.

The first trigger 1002 may include an annular base configured to encircle the outer supports 1010 and one or more finger holds. The first trigger 1002 couples to the second trigger 1004, such that proximal movement of the first trigger 1002 results in proximal movement of the second trigger 1004. The second trigger 1004 may be substantially similar in structure, function, and/or operation to the proximal trigger 114 of the stent delivery system 100 described above. The third trigger 1006 may be substantially similar in structure, function, and/or operation to the distal trigger 116 described above. Moreover, the coupling and operation of the second trigger 1004 and the third trigger 1006 may be substantially similar to the proximal trigger 114 and distal trigger 116 of the stent delivery system 100, as described above.

The sheathing mechanism 201 may be used to sheath the stent 20. Sheathing of the stent 20, by a sheathing action to transition the stent delivery system 1000 from the partially sheathed configuration to the fully sheathed delivery configuration, may be accomplished in much the same way as described above. As can be appreciated, the sheathing fingers of the sheathing mechanism 201 may have a longer length to accommodate a longer stent. Similarly, the sheathing mechanism 201 may be longer.

Figure 17A:
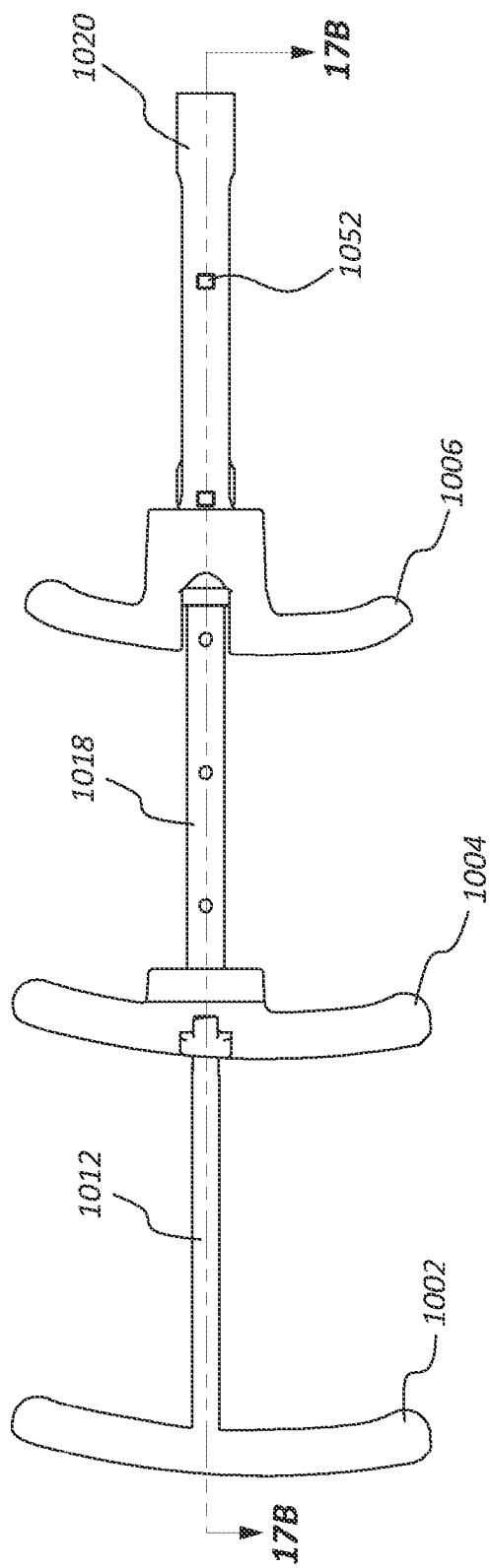
FIG. 17A is a side view of an internal connector, a third trigger, a floater, a second trigger, external floater arms, and a first trigger of the stent delivery system of FIGS. 16A and 16B.
Figure 17B:
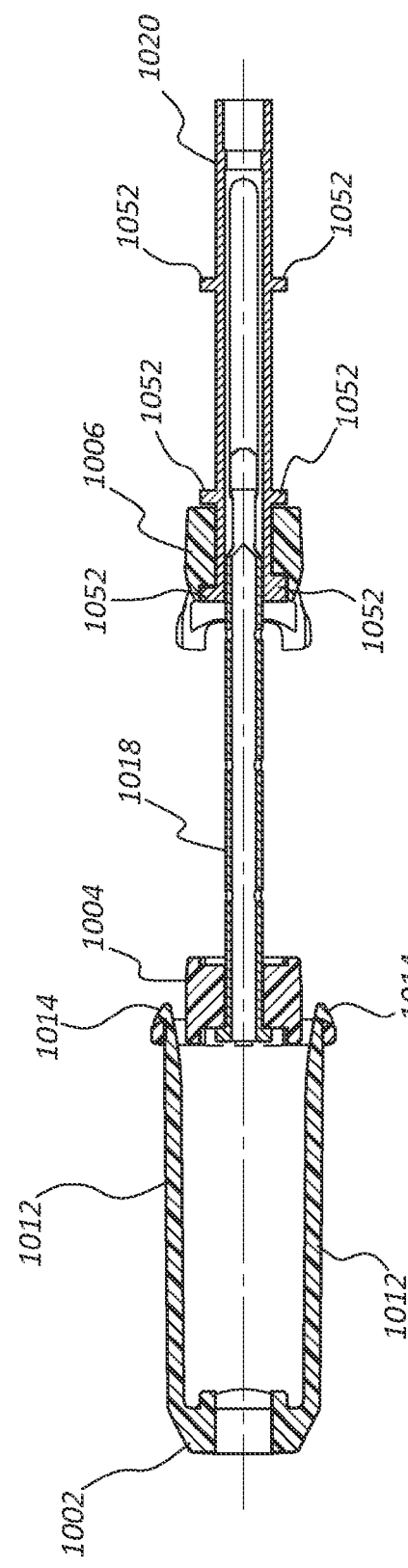
FIG. 17B is a top cross-sectional view of an internal connector, a third trigger, a floater, a second trigger, external floater arms, and a first trigger of the stent delivery system of FIGS. 16A and 16B.

FIGS. 17A and 17B are side and top cross-sectional views, respectively, of an internal connector 1020, a third trigger 1006, a floater 1018, a second trigger 1004, floater arms 1012, and a first trigger 1002 of the stent delivery system of FIGS. 16A and 16B. FIG. 17A is a side view and FIG. 17B is a top sectional view illustrating the coupling relationship of the first trigger 1002, the second trigger 1004, a floater 1018, an internal connector 1020, and the third trigger 1006. The floater 1018 and internal connector 1020 may be substantially similar in structure, function, and/or operation to the floater 118 and internal connector 120 of stent delivery system 100 of FIG. 1, described above. The coupling and operation of the second trigger 1004, the floater 1018, the internal connector 1020, and the third trigger 1006 may be substantially similar to the corresponding components of the stent delivery system 100, as described above with reference to FIGS. 11A and 11B.

Referring collectively to FIGS. 17A and 17B, the third trigger 1006 couples to the internal connector 1020. In the illustrated embodiment, one or more outwardly extending protrusions 1052 on the internal connector 1020 mate with trigger guides on the third trigger 1006. As the third trigger 1006 is retracted proximally, toward the handle 1008 (FIG. 16A), the third trigger 1006 retracts the internal connector 1020 proximally. Thus, retraction of the third trigger 1006 results in retraction of the outer sheath 1026 and pod 1034 (FIG. 16A), which results in at least partial deployment of a stent 20 sheathed within the pod 1034.

The second trigger 1004 is mechanically coupled to the third trigger 1006 by the floater 1018. In the illustrated embodiment, the floater 1018 engages a floater engagement ring (coupled to inwardly protruding trigger guides) of the second trigger 1004. The floater engagement ring engages the proximal end of the floater 1018 such that proximal movement of the second trigger 1004 retracts the floater 1018. The distal end of the floater engages the third trigger 1006 and/or the internal connector 1020. Accordingly, retraction of the second trigger 1004 results in retraction of the third trigger 1006 and/or the internal connector 1020, which retracts the outer sheath 1026 and pod 1034 and at least partially deploys a sheathed stent 20.

The first trigger 1002 includes one or more barbed external floater arms 1012 that may extend distally from the base of the first trigger 1002 to engage the second trigger 1004. Barbs 1014 at the distal end of the external floater arms 1012 may engage a base of the second trigger 1004 as the first trigger 1002 moves proximally, while allowing distal movement of the first trigger 1002 relative to the second trigger 1004. Stated differently, the barbed engagement arms 1002 allow the second trigger 1004 to move proximally relative to the first trigger 1002, such that the second trigger 1004 can be operated and retracted toward the first trigger 1002, even after the first trigger 1002 has been retracted.

Figure 18A:
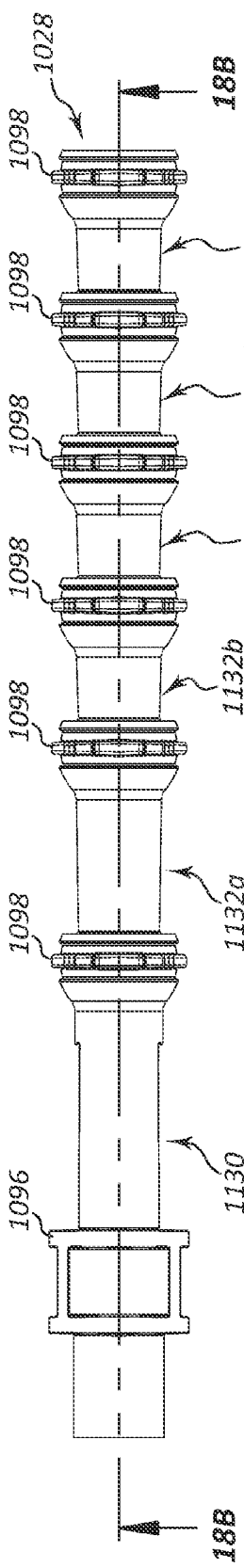
FIG. 18A is a side view of a panchor of the stent delivery system of FIGS. 16A and 16B.
Figure 18B:
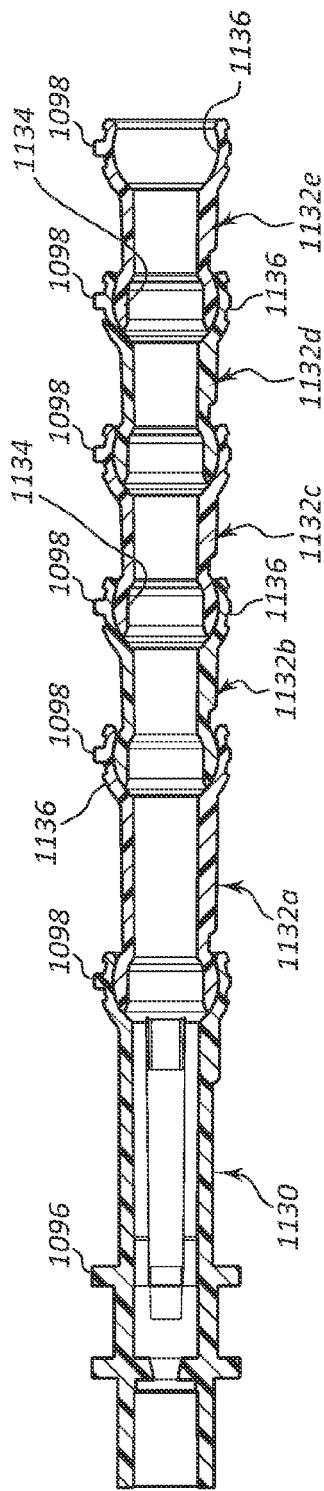
FIG. 18B is a side cross-sectional view of the panchor of the stent delivery system of FIGS. 16A and 16B.
Figure 18C:
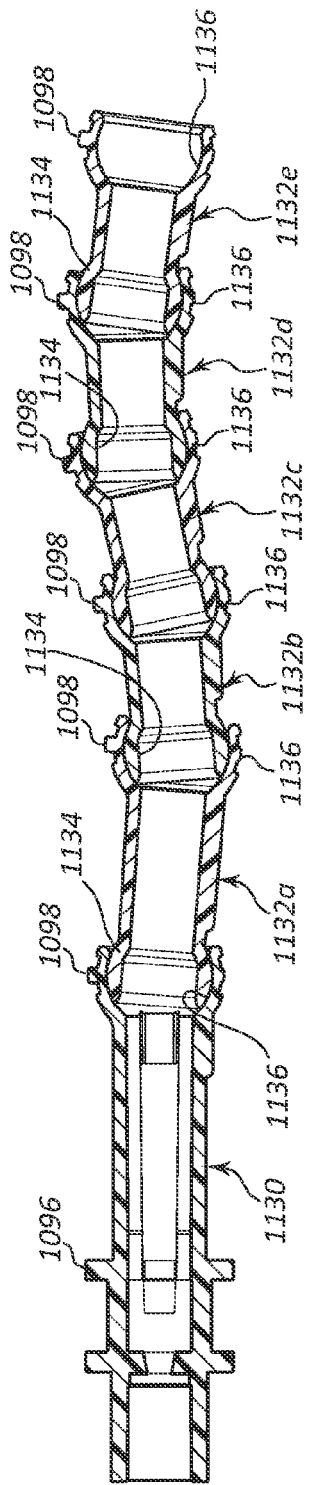
FIG. 18C is a side cross-sectional view illustrating flexibility of the panchor of the stent delivery system of FIGS. 16A and 16B.

FIGS. 18A-18C are views of the panchor 1028 of the stent delivery system 1000. The panchor includes a base segment 1130 and a plurality of extension segments 1132a, 1132b, 1132c, 1132d, 1132e (collectively 1132). FIG. 18A is a side view of the panchor 1028. FIG. 18B is a side cross-sectional view of the panchor 1028. FIG. 18C is a side cross-sectional view illustrating flexibility of the panchor 1028.

Referring to FIGS. 18A-18C, collectively, the panchor 1028 may include a push surface 1096 and one or more anchors 1098. The push surface 1096 is configured to restrict proximal movement of the stent 20 as the outer sheath 1026 is pulled proximally over the stent 20 during deployment. The anchors 1098 may include a flange at a distal end of the base segment 1130 and/or the distal end of the one or more extension segments 1132 of the panchor 1028. In the illustrated embodiment, the anchors 1098 may include a plurality (e.g., five) of protrusions or apices about the circumference of a distal end of the base segment 1130 and/or one or more extension segments 1132. The protrusions of each anchor 1098 are configured to be positioned between connectors of the stent 20 that interconnect annular segments (or rows) of struts in the scaffolding of structure of the stent 20 to engage the distal ends of the struts. Engagement of the struts by the anchors 1098 of the panchor 1028 restricts distal movement of the stent 20, so long as the engaged portion of the stent 20 remains sheathed within the pod 1034 and compressed around the panchor 1028.

The plurality of segments of the panchor 1028, namely the base segment 1130 and the extension segments 1132, may be rotatably and/or flexibly coupled to enable the panchor 1028 to be flexible. In the illustrated embodiment, the segments 1130, 1132 comprise ball 1134 and socket 1136 connections. A ball 1134 at a proximal end of the extension segments 1132 fits into and is received by a socket 1136 at the distal end of the base segment 1130 or another extension segment 1132. The ball 1134 and socket 1136 connection allows the segments 1130, 1132 to bend and rotate relative to each other. FIG. 18C illustrates the panchor 1028 having a plurality of extension segments 1132 in a curved configuration.

In the illustrated embodiment, the first extension segment 1132*a* may be slightly longer than the other extension segments 1132*b*, 1132*c*, 1132*d*, 1132*e*. The length of any of the extension segments 1132 and/or the base member 1130 may be adjusted according to the design and/or configuration of a stent to be deployed. Moreover, the number of protrusions on the plurality of anchors 1098 may vary according to the design and/or configuration of a stent to be deployed.

Figure 19:
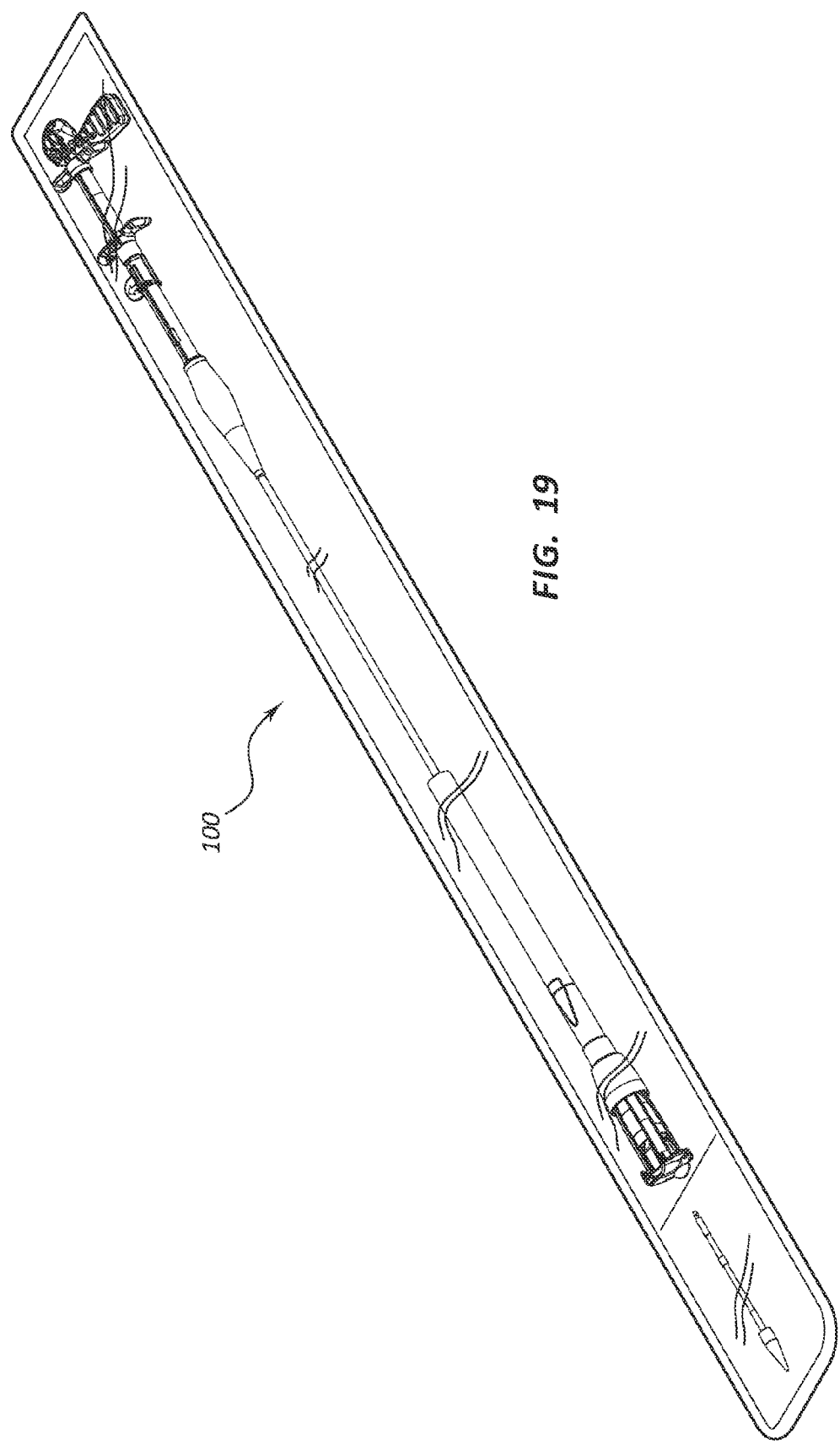
FIG. 19 is a perspective view of a packaged stent delivery system in a storage configuration, according to one embodiment.

FIG. 19 is a perspective view of the stent delivery system 100 of FIG. 1 packaged in a storage configuration, according to one embodiment.

As can be appreciated, other embodiments are possible in which additional triggers, beyond three, are coupled together in a similar manner as described herein.

The present disclosure may be embodied in other specific forms without departing from its spirit or essential characteristics. The described embodiments are to be considered in all respects only as illustrative and not restrictive. As can be appreciated by those having skill in the art, many changes may be made to the details of the above-described embodiments without departing from the underlying principles of the invention. The scope of the invention is, therefore, indicated by the appended claims rather than by the foregoing description. All changes which come within the meaning and range of equivalency of the claims are to be embraced within their scope.

What is claimed is:

1. A delivery system for sheathing a crimpable implantable device and deploying the implantable device within a body of a patient, the delivery system comprising:
   a delivery device to position and deploy the implantable device, the delivery device having a tubular member configured to receive and house the implantable device in a crimped state for delivery to a target location within the body of the patient, the delivery device having a partially sheathed configuration, a fully sheathed delivery configuration, and a deployed configuration, the tubular member comprising a first trigger safety notch and a second trigger safety notch; and
   a safety mechanism removably engaged to the delivery device to limit operation of the delivery device and inhibit unintended deployment of the implantable device, the safety mechanism comprising an annular body with a deflectable tab including a first protrusion, the first protrusion extending inward relative to an inner surface of the annular body, wherein the safety mechanism, while engaged around the delivery device, is slidably moveable relative to the delivery device in a single direction from a first trigger safety position with the first protrusion engaging the first trigger safety notch to a second trigger safety position with the first protrusion causing a locking engagement at the second trigger safety notch to permit transition of the delivery device from the partially sheathed configuration at the first trigger safety position to the fully sheathed delivery configuration at the second trigger safety position during a sheathing process, wherein the locking engagement at the second trigger safety notch restricts slidable movement of the safety mechanism relative to the delivery device such that transition of the delivery device from the fully sheathed delivery configuration to the partially sheathed configuration and the deployed configuration at the second trigger safety position is restricted, and wherein the safety mechanism is removable from the delivery device to allow transition of the delivery device from the fully sheathed delivery configuration to the deployed configuration.

2. The delivery system of claim 1, wherein the annular body of the safety mechanism is further configured to restrict transition of the delivery device from the partially sheathed configuration to the deployed configuration to prevent premature full deployment of the implantable device in a partially sheathed state and before a sheathing process to fully sheathe the implantable device.

3. The delivery system of claim 1, wherein the safety mechanism is configured to provide an audible click to indicate that the delivery device has been transitioned to the fully sheathed delivery configuration and that the implantable device is fully sheathed.

4. The delivery system of claim 1, wherein the delivery device further comprises a trigger assembly coupled to the tubular member to facilitate deployment of the implantable device, wherein the safety mechanism is a trigger safety and the annular body comprises one or more radial protrusions configured to engage and limit operation of the trigger assembly of the delivery device.

5. The delivery system of claim 4, wherein the trigger assembly comprises a plurality of triggers, wherein the one or more radial protrusions of the annular body of the trigger safety limit proximal movement of the plurality of triggers, thereby inhibiting unintended deployment of the implantable device, while permitting distal movement of the plurality of triggers.

6. The delivery system of claim 5, wherein the tubular member of the delivery device comprises:
   an inner member to couple to the implantable device in the partially sheathed configuration and the fully sheathed delivery configuration; and
   an outer sheath coaxially surrounding at least a distal portion of the inner member, and having a distal portion configured to enclose the implantable device in the fully sheathed delivery configuration, wherein the outer sheath is slidably moveable relative to the inner member, and wherein proximal movement of the outer sheath relative to the inner member deploys the implantable device, wherein the trigger assembly is configured to move the outer sheath proximally relative to the inner member to withdraw the implantable device from the tubular member.

7. The delivery system of claim 6, wherein the trigger assembly further comprises an internal connector bonded to the outer sheath,
   wherein the plurality of triggers couple to the internal connector,
   wherein the trigger safety engages the internal connector to limit operation of the trigger assembly.

8. The delivery system of claim 6,
   wherein the delivery device further comprises one or more elongate outer supports configured to support the trigger assembly, including the plurality of triggers,
   wherein the trigger safety engages the one or more outer supports to limit operation of the trigger assembly.

9. The delivery system of claim 8, wherein the one or more outer supports define one or more trigger safety notches configured to be engaged by the trigger safety to limit proximal movement of the plurality of triggers.

10. The delivery system of claim 1, wherein the annular body is configured to, in a closed configuration, encircle and engage the delivery device and configured to transition to an open configuration to disengage from the delivery device.

11. The delivery system of claim 10, wherein the safety mechanism further comprises a release tab for opening the annular body to transition the annular body from the closed configuration to the open configuration and to disengage the annular body from the delivery device and thereby release the safety mechanism.

12. The delivery system of claim 10, wherein the annular body comprises a hinge configured to allow the annular body to open to the open configuration and to disengage from the delivery device.

13. The delivery system of claim 10, wherein the annular body further comprises a second protrusion disposed on an inner surface of the annular body, wherein the second protrusion
   is configured to restrict movement of an outer sheath of the tubular member of the delivery device relative to the safety mechanism when the annular body is in the closed configuration around the delivery device.

* * * * *